(12) United States Patent
Plowman et al.

(10) Patent No.: US 6,495,353 B1
(45) Date of Patent: *Dec. 17, 2002

(54) HUMAN ORTHOLOGUES OF WART

(75) Inventors: Gregory Plowman, San Carlos; Peter Flanagan, San Francisco, both of CA (US)

(73) Assignee: Sugen, Inc., South San Francisco, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/233,857

(22) Filed: Jan. 20, 1999

Related U.S. Application Data

(60) Provisional application No. 60/072,023, filed on Jan. 21, 1998.

(51) Int. Cl.$^7$ .................................................. C12N 9/00
(52) U.S. Cl. ........................ 435/183; 435/183; 435/194
(58) Field of Search ........................... 435/194, 15, 41, 435/252.3, 320.1, 325; 536/23.2, 23.5, 23.4

(56) References Cited

U.S. PATENT DOCUMENTS

| | | | |
|---|---|---|---|
| 4,343,940 A | 8/1982 | Kreighbaum et al. | 544/283 |
| 4,376,110 A | 3/1983 | David et al. | 436/513 |
| 4,447,608 A | 5/1984 | Jones et al. | 544/287 |
| 4,757,072 A | 7/1988 | Kabbe et al. | 514/257 |
| 4,945,050 A | 7/1990 | Sanford et al. | 435/172.1 |
| 5,217,999 A | 6/1993 | Levitzki et al. | 514/613 |
| 5,283,173 A | 2/1994 | Fields et al. | 435/6 |
| 5,302,606 A | 4/1994 | Spada et al. | 514/357 |
| 5,316,553 A | 5/1994 | Kaul et al. | 8/639 |
| 5,330,992 A | 7/1994 | Eissenstat et al. | 514/312 |
| 5,602,171 A | 2/1997 | Tang et al. | 514/455 |
| 5,610,173 A | 3/1997 | Schwartz et al. | 514/378 |

FOREIGN PATENT DOCUMENTS

| | | |
|---|---|---|
| EP | 0 520 722 A2 | 12/1992 |
| EP | 0 562 734 A1 | 9/1993 |
| EP | 0 566 226 A1 | 10/1993 |
| WO | 91/15495 | 10/1991 |
| WO | 92/20642 | 11/1992 |
| WO | 92/21660 | 12/1992 |
| WO | 93/09236 | 5/1993 |
| WO | 94/03427 | 2/1994 |
| WO | 94/14808 | 7/1994 |
| WO | 94/23039 | 10/1994 |
| WO | 96/18738 | 6/1996 |
| WO | 96/22976 | 8/1996 |
| WO | WO 96/30402 | * 10/1996 |

OTHER PUBLICATIONS

Abe et al., "Molecular Characterization of a Novel Metabotropic Glutamate Receptor mGluR5 Coupled to Inositol Phosphate/Ca$^{2+}$ Signal," *J. Biol. Chem.* 267(19):13361–13368 (1992).

Allen et al., "Modulation of CD4 by suramin," *Clin. Exp. Immunol.* 91:141–146 (1991).

Altschul et al., "Basic Local Alignment Search Tool," *J. Mol. Biol.* 215:403–410 (1990).

Anafi et al., "Tyrphostin–Induced Inhibition of p210$^{bcr-abl}$ Tyrosine Kinase Activity Induces K562 to Differentiate," *Blood* 82:3524–3529 (1993).

Ausubel et al.(editor), *Current Protocols in Molecular Biology*, John Wiley & Sons (1994) (Table of Contents for vols. 1 & 2).

Baker et al., "Induction of acetylcholine receptor clustering by native polystyrene beads," *Journal of Cell Science* 102:543–555 (1992).

Barker et al., "In vitro activity of non–glutamate containing quinazoline–based thymidylate synthase inhibitors," *Proceedings of the American Association for Cancer Research* 32:327 at abstract No. 1939 (1991).

Bayer et al., "The Avidin–Biotin Complex in Affinity Cytochemistry," *Methods in Enzymology* 62:308–319 (1979).

Benoist and Chambon, "In vivo sequence requirements of the SV40 early promoter region," *Nature* 290:304–310 (1981).

Bertino, "Toward Improved Selectivity in Cancer Chemotherapy: The Richard and Hinda Rosenthal Foundation Award Lecture," *Cancer Research* 39:293–304 (1979).

Bilder et al., "Tyrphostins inhibit PDGF–induced DNA synthesis and associated early events in smooth muscle cells," *Am. J. Physiol.* 260(Cell Physiol.29):C721–C730 (1991).

Bishop, "Molecular Themes in Oncogenesis," *Cell* 64:235–248 (1991).

Bollon and Stauver, "DNA Transformation Efficieny of Various Bacterial and Yeast Host–Vector Systems," *Journal of Clinical Hematology and Oncology* 10(2&3):39–48 (1980).

Botstein et al., "Making Mutations in vitro and Putting Them Back into Yeast," *Miami Winter Symposia—From Gene to Protein: Translation into Biotechnology*, edited by Ahmad et al., Academic Press, 19:265–274 (1982).

Brinster et al., "Factors Affecting the Efficiency of Introducing Foreign DNA into Mice by Microinjecting Eggs," *Proc. Natl. Acad. Sci. USA* 82:4438–4442 (1985).

(List continued on next page.)

Primary Examiner—Elizabeth Slobodyansky
(74) *Attorney, Agent, or Firm*—Foley & Lardner

(57) ABSTRACT

The present invention relates in part to hWART nucleic acid molecules. The invention also relates in part to nucleic acid molecules encoding portions of hWART full-length proteins, nucleic acid vectors containing hWART nucleic acid molecules, recombinant cells containing such nucleic acid vectors, polypeptides purified from such recombinant cells, antibodies to such polypeptides, and methods of identifying compounds that modulate the function of an hWART polypeptide. Also disclosed are methods for diagnosing abnormal cell proliferative conditions in an organism using hWART-related molecules or compounds.

24 Claims, 4 Drawing Sheets

OTHER PUBLICATIONS

Broach, "The Yeast Plasmid 2β Circle," *Cell* 28:203–204 (1982).

Broach, "The Yeast Plasmid 2β Circle," in *The Molecular Biology of the Yeast Saccharomyces: Life Cycle and Inheritance*, Cold Spring Harbor Laboratory, Cold Spring Harbor, NY, pp. 445–470 (1981).

Brunton et al., "Anti–tumour activity of novel tryphostins in breast cancer cells," Proceedings of the American Association for Cancer Research 33:558 at abstract No. 3335 (1992).

Bryant et al., "Tumor suppressor genes encoding proteins required for cell interactions and signal transduction in drosophila," *Development 1993 Supplement* 239–249 (1993).

Bryckaert et al., "Inhibition of Platelet–Derived Growth Factor–Induced Mitogenesis and Tyrosine Kinase Activity in Cultured Bone Marrow Fibroblasts by Tyrphostins," *Exp. Cell Research* 199:255–261 (1992).

Bullock et al., *Techniques in Immunocytochemistry*, Academic Press, Orlando, FL: vol. 1 (1982), vol. 2 (1983), vol. 3 (1985) (Table of Contents Only).

Burke et al., "Arylamides of Hydroxylated Isoquinolines as Protein–Tyrosine Kinase Inhibitors," *Bioorganic & Medical Chemistry Letters* 2(12):1771–1774 (1992).

Burke et al., "Bicyclic Compounds as Ring–Constrained Inhibitors of Protein–Tyrosine Kinase p56$^{ick\ 1}$," *Journal of Medicinal Chemistry* 36(4):425–432 (1993).

Campbell, *Monoclonal Antibody Technology: Laboratory Techniques in Biochemistry and Molecular Biology*, vol. 13, Elsevier Science Publishers, Amsterdam, The Netherlands (1984) (Table of Contents Only).

Capecchi, "Altering the Genome by Homologous Recombination," *Science* 244:1288–1292 (1989).

Capecchi, "High Efficiency Transformation by Direct Microinjection of DNA into Cultured Mammalian Cells," *Cell* 22:479–488 (1980).

Cenatiempo, "Prokaryotic gene expression in vitro: transcription–translation coupled systems," *Biochimie* 68:505–515 (1986).

Chard, *An Introduction to Radioimmunoassay and Related Techniques*, Elsevier Science Publishers, Amsterdam, The Netherlands (1986) (Table of Contents Only).

Chater et al., "Streptomyces ØC31–Like Phages: Cloning Vectors, Genome Changes and Host Range," in *Sixth International Symposium on Actinomycetes Biology*, edited by Szabe et al., Akademiai Kaido, Budapest, Hungary, pp. 45–52 (1986).

Chen and Okayama, "High–Efficiency Transformation of Mammalian Cells by Plasmid DNA," *Molecular and Cellular Biology* 7(8):2745–2752 (1987).

Chomczynski and Sacchi, "Single–Step Method of RNA Isolation by Acid Guanidium Thiocyanate–Phenol–Chloroform Extraction," *Analytical Biochemistry* 162:156–159 (1987).

Chu et al., "Electroporation for the efficient transfection of mammalian cells with DNA," *Nucleic Acids Research* 15:1311–1326 (1987).

Curiel et al., "Gene Transfer to Respiratory Epithelial Cells via the Receptor–mediated Endocytosis Pathway," *Am. J. Respir. Cell. Mol. Biol.* 6:247–252 (1992).

Curtin et al., "Inhibition of the growth of human hepatocellular carcinoma in vitro and in athymic mice by a quinazoline inhibitor of thymidylate synthase, CB3717," *Br. J. Cancer* 53:361–368 (1986).

Dolle et al., "5,7–Dimethoxy–3–(4–pyridinyl)quinoline is a Potent and Selective Inhibitor of Human Vascular β–Type Platelet–Derived Growth Factor Receptor Tyrosine Kinase," *J. Med. Chem.* 37:2627–2629 (1994).

Dong et al., "Activation of tumoricidal properties in macrophages by lipopolysaccharide requires protein–tyrosine kinase activity," *Journal of Leukocyte Biology* 53:53–60 (1993).

Dong et al., "Protein Tyrosine Kinase Inhibitors Decrease Induction of Nitric Oxide Synthase Activity in Lipopolysaccharide–Responsive and Lipopolysaccharide–Nonresponsive Murine Macrophages," *The Journal of Immunology* 151(5):2717–2724 (1993).

Dreborg et al., "Ch. 10—The chemistry and standardization of allergens," in *Handbook of Experimental Immunology—vol. 1: Immunochemistry*, 4th Ed., edited by Weir et al., Blackwell Scientific Publications, Oxford, England, pp. 10.1–10.28 (1986).

Engvall and Perlmann, "Enzyme–Linked Immunosorbent Assay, ELISA. III. Quantitation of Specific Antibodies by Enzyme–Labeled Anti–Immunoglobulin in Antigen–Coated Tubes," *J. Immunology* 109:129–135 (1972).

Felgner et al., "Lipofection: A Highly Efficient, Lipid–mediated DNA–transfection Procedure," *Proc. Natl. Acad. Sci. USA* 84:7413–7417 (1987).

Felgner et al., "Cationic Liposome–Mediated Transfection," *Nature* 337:387–388 (1989).

Fernandes et al., "Biochemical and Antitumor Effects of 5,8–Dideazaisopteroylglutamate, a Unique Quinazoline Inhibitor of Thymidylate Synthase," *Cancer Research* 43:1117–1123 (1983).

Ferris et al., "Synthesis of Quinazoline Nucleosides from Ribose and Anthranilonitrole. Application of Phase–Transfer Catalysis in Nucleoside Synthesis," *J. Org. Chem.* 44(2):173–178 (1979).

Fingl and Woodbury, "Chapter 1—General Principles," in *The Pharmacological Basis of Therapeutics* 5th edition, Goodman and Gilman editors, MacMillan Publishing Co., Inc., New York, pp. 1–46 (1975).

Fry et al., "A Specific Inhibitor of the Epidermal Growth Factor Receptor Tyrosine Kinase," *Science* 265:1093–1095 (1994).

Gazit et al., "Tyrphostins 1. Synthesis and Biological Activity of Protein Tyrosine Kinase Inhibitors," *J. Med. Chem.* 32:2344–2352 (1989).

Gazit et al., "Tyrphostins. 3. Structure–Activity Relationship Studies of a α–Substituted Benzylidenemalonotrile 5–S–Aryltyrophostins," *J. Med. Chem.* 36:3556–3564 (1993).

Gennaro (editor), *Remington's Pharmaceutical Sciences* (1990) (Table of Contents Only).

Gerard et al., "cDNA Synthesis by Cloned Moloney Murine Leukemia Virus Reverse Transcriptase Lacking Rnase H Activity," *Focus* 11(4):66–69 (1989).

Gilman et al., "Isolation of sigma–28–specific promoters from *Bacillus subtilis* DNA," *Gene* 32:11–20 (1984).

Glick and Whitney, "Factors and affecting the expression of foreign proteins in *Escherichia coli*," *Journal of Industrial Microbiology* 1:277–282 (1987).

Goding, "Conjugation of Antibodies with Fluorochromes: Modifications to the Standard Methods," *J. Immunological Methods* 13:215–226 (1976).

Gold et al., "Translational Initiation in Prokaryotes," *Ann. Rev. Microbiol.* 35:365–403 (1981).

Gottesman, "Bacterial Regulation: Global Regulatory Networks," *Ann. Rev. Genet.* 18:415–441 (1984).

Gryczan, "Ch. 10—Molecular Cloning in *Bacillus subtilis*," in *The Molecular Biology of the Bacilli*, edited by Dubnau, Academic Press, New York, pp. 307–329 (1982).

Hamer and Walling, "Regulation In Vivo of a Cloned Mammalian Gene: Cadmium Induces the Transcription of a Mouse Metallothionein Gene in SV40 Vectors," *J. of Molecular and Applied Genetics* 1:273–288 (1982).

Hammer et al., "Spontaneous Inflammatory Disease in Transgenic Rats Expressing HLA–B27 and Human $\beta_2$m: An Animal Model of HLA–B27–Associated Human Disorders," *Cell* 63:1099–1112 (1990).

Hanks and Hunter, "The eukaryotic protein kinase superfamily: kinase (catalytic) domain structure and classification," *FASEB J.* 9:576–596 (1995).

Haslam et al., "Pleckstrin domain homology," *Nature* 363:309–310 (1993).

Houdebine and Chourrout, "Transgenesis in Fish," *Experientia* 47:891–897 (1991).

Hurby et al., in *Synthetic Peptides: A User's Guide*, edited by Grant, Washington University School of Medicine, W.H. Freeman and Company, New York, pp. 289–307 (1992).

Izaki, *Japanese Journal of Bacteriology* 33(6):729–742 (1978).

Jackman, "ICI D1694, a Quinazoline Antifolate Thymidylate Synthase Inhibitor That Is a Potent Inhibitor of L1210 Tumor Cell Growth in Vitro and in Vivo: A New Agent for Clinical Study," *Cancer Research* 51:5579–5586 (1991).

Jasny, "Insect Viruses Invade Biotechnology," *Science* 238:1653 (1987).

John and Twitty, "Plasmids as Epidemiologic Markers in Nosocomial Gram–Negative Bacilli: Experience at a University and Review of the Literature," *Reviews of Infectious Diseases* 8:693–704 (1986).

Johnston and Hopper, "Isolation of the yeast regulatory gene GAL4 and analysis of its dosage effects on the galactose/melibiose regulon," *Proc. Natl. Acad. Sci. USA* 79:6971–6975 (1982).

Jones et al., "Quinazoline Antifolates Inhibiting Thymidylate Synthase: Varation of the Amino Acid," *J. Med. Chem.* 29:1114–1118 (1986).

Joyner et al., "Production of a mutation in mouse En–2 gene by homologous recombination in embryonic stem cells," *Nature* 338:153–156 (1989).

Kasprzak et al., "Location of a Contact Site Between Actin and Myosin in the Three–Dimensional Structure of the Acto–S1 Complex," *Biochemistry* 28:9230–9238 (1989).

Kaur, "Tyrphostin induced growth inhibition: correlation with effect on $p210^{bcr-abl}$ autokinase activity in K562 chronic myelogenous leukemia," *Anti–Cancer Drugs* 5:213–222 (1994).

Kendall and Cohen, "Plasmid Transfer in *Streptomyces lividans*: Identification of a kil–kor System Associated with the Transfer Region of PIJ101," *Journal of Bacteriology* 169:4177–4183 (1987).

King et al., "Site–specific dephosphorylation and deactivation of the human insulin receptor tyrosine kinase by particulate and soluble phosphotyrosyl protein phosphatases," *Biochem. J.* 275:413–418 (1991).

Kohler and Milstein, "Continuous cultures of fused cells secreting antibody of predefined specificity," *Nature* 256:495–497 (1975).

Kuo et al., "Effects of signalling transduction modulators on the transformed phenotypes in v–H–ras–transformed NIH 3T3 cells," *Cancer Letters* 74:197–202 (1993).

Lasko et al., "Loss of constitutional heterozygosity in human cancer," *Ann Rev Genet* 25:281–314 (1991).

Lee and Skibo, "Active–Site–Directed Reductive Alkylation of Xanthine Oxidase by Imidazo[4,5–g]quinazoline–4,9–diones Functionalized with a Leaving Group," *Biochemistry* 26:7355–7362 (1987).

Lemus et al., "Studies of Extended Quinone Methides. Synthesis and Physical Studies of Purine–like Monofunctional and Bifunctional Imidazo[4,5–g]quinazoline Reductive Alkylating Agents," *J. Org. Chem.* 54:3611–3618 (1989).

Levitzki, "Tryphostins: tyrosine kinase blockers as novel antiproliferative agents and dissectors of signal transduction," *FASEB J.* 6:3275–3282 (1992).

Ley and Seng, "Synthesis Using Benzofuroxan," *Synthesis* 1975:415–422 (1975).

Lutz et al., "The Distribution of Two hnRNP–Associated Proteins Defined by a Monoclonal Antibody Is Altered in Heat–Shocked HeLa Cells," *Experimental Cell Research* 175:109–124 (1988).

Lyall et al., "Tyrphostins Inhibit Epidermal Growth Factor (EGF)–Receptor Tyrosine Kinase Activity in Living Cells and EGF–stimulated Cell Proliferation," *J. Biol. Chem.* 264:14503–14509 (1989).

MaGuire et al., "A New Series of PDGF Receptor Tyrosine Kinase Inhibitors: 3–Substituted Quinoline Derivatives," *J. Med. Chem.* 37:2129–2137 (1994).

Maniatis, "Ch. 11—Recombinant DNA Procedures in the Study of Eukaryotic Genes," in *Cell Biology: A Comprehensive Treatise, vol. 3, Gene Sequence Expression*, Academic Press, NY, pp. 563–608 (1980).

Maxwell et al., "$^{19}$F Nuclear Magnetic Resonance Imaging of Drug Distribution in Vivo: The Disposition of an Antifolate Anticancer Drug in Mice," *Magnetic Resonance in Medicine* 17:189–196 (1991).

Mayer et al., "A novel viral oncogene with structural similarity to phospholipase C," *Nature* 332:272–275 (1988).

McKnight, "Functional Relationships between Transcriptional Control Signals of the Thymidine Kinase Genes of Herpes Simplex Virus," *Cell* 31:355–365 (1982).

Michael A. Innis et al., *PCR Protocols: A Guide to Methods and Applications*, edited by Michael A. Innis et al., Academic Press, San Diego (1990) (Table of Contents Only).

Miller et al., "An Insect Baculovirus Host–Vector System for High–Level Expression of Foreign Genes," in *Genetic Engineering: Principles and Methods*, edited by Setlow et al., Plenum Press, 8:277–298 (1986).

Miller, "Human gene therapy comes of age," *Nature* 357:455–460 (1992).

Mini et al., "Cytotoxic Effects of Folate Antagonists against Methotrexate–resistant Human Leukemic Lymphoblast CCRF–CEM Cell Lines," *Cancer Research* 45:325–330 (1985).

Mulligan, "The Basic Science of Gene Therapy," *Science* 260:926–932 (1993).

Nelson, "Detection of Acridinium Esters by Chemiluminescence," *Nonisotopic DNA Probe Techniques*, ed. Larry J. Kricka, (San Diego: Academic Press, Inc.) pp. 275–310 (1992).

Okayama and Berg, "A cDNA Cloning Vector That Permits Expression of cDNA Inserts in Mammalian Cells," *Molecular and Cellular Biology* 3:280–289 (1983).

Pati, "Novel vectors for expression of cDNA encoding epitope–tagged proteins in mammalian cells," *Gene* 114:2856–288 (1992).

Pawson and Schlessinger, "SH2 and SH3 domains," *Current Biology* 3(7):434–442 (1993).

Peterson and Barnes, "Genistein and Biochanin A Inhibit the Growth of Human Prostate Cancer Cells but not Epidermal Growth Factor Receptor Tyrosine Autophosphorylation," *The Prostate* 22:335–345 (1993).

Phillips and Castle, "Quino[1,2–c]quinazolines. I. Synthesis of Quino[1,2–c]quinazolinium Derivatives and the Related Indazolo[2,3–a]quinoline Derivatives as Analogs of the Antitumor Benzo[c]phenanthridine Alkaloids," *J. Heterocyclic Chemistry* 17:1489–1496 (1980).

Pillemer et al., "Insulin Dependence of Murine Lymphoid T–Cell Leukemia," *Brit. J. Cancer* 50:80–85 (1992).

Ponting and Bork, "Pleckstrin's repeat performance: a novel domain in G–protein signaling?" *TIBS* 21:245–246 (1996).

Posner et al., "Kinetics of Inhibition by Tyrphostins of the Tyrosine Kinase Activity of the Epidermal Growth Factor Receptor and Analysis by a New Computer Program," *Molecular Pharmacology* 45:673–683 (1993).

Pursel et al., "Genetic Engineering of Livestock," *Science* 244:1281–1288 (1989).

Reece et al., "Pharmacokinetics of Trimetrexate Administered by Five–Day Continuous Infusion to Patients with Advanced Cancer," *Cancer Research* 47:2996–2999 (1987).

Rendu et al., "Inhibition of Platelet Activation by Tyrosine Kinase Inhibitors," *Biochemical Pharmacology* 44(5):881–888 (1992).

Robertson, *Teratocarcinomas and embryonic stem cells: a practical approach*, IRL Press (1987) (Table of Contents).

Rubin, "Drosophila melanogaster as an Experimental Organism," *Science* 240:1453–1459 (1988).

Sadowski et al., A Noncatalytic Domain Conserved among Cytoplasmic Protein–Tyrosine Kinases Modifies the Kinase Function and Transforming Activity of Fujinami Sarcoma Virus P130$^{gag-fps}$, *Molecular and Cellular Biology* 6(12):4396–4408 (1986).

Sambrook and Maniatis., *Molecular Cloning: A Laboratory Manual, 2nd Edition*, Cold Spring Harbor Laboratory Press (1989) (Table of Contents—All Three vols.).

Sauro and Thomas, "Decreased Sensitivity of Aorta from Hypertensive Rats to Vasorelaxation by Tryphostin," *Life Sciences* 53:PL371–376 (1993).

Sauro and Thomas, "Tyrphostin Attenuates Platelet–Derived Growth Factor–Induced Contraction in Aortic Smooth Muscle Through Inhibition of Protein Tyrosine Kinase(s)," *The Journal of Pharmacology and Experimental Therapeutics* 267:1119–1125 (1993).

Sculier et al., "Role of an Intensive Care Unit (ICU) in a Medicinal Onocology Department," *Cancer Immunol. and Immunotherapy* 23:A65 at abstract No. 257 (1986).

Sikora and Grzelakowska–Sztabert, "Quinazoline CB 3717 and CB 3703 Inhibitors of Folate Retention and Metabolism in Ehrlich Ascites Carcinoma Cells and Some Organs of the Host–Mouse," *Cancer Letters* 23:289–295 (1984).

Sikora et al., "Development of an Assay for the Estimation of $N^{10}$–Propargyl–5,8–dideazafolic Acid Polyglutamatesb 55 in Tumor Cells," *Analytical Biochemistry* 172:344–355 (1988).

Silver et al., "Amino terminus of the yeast GAL4 gene product is sufficient for nuclear localization," *Proc. Natl. Acad. Sci. USA* 81:5951–5955 (1984).

Simons et al., "Gene Transfer into Sheep," *Bio/Technology* 6:179–182 (1988).

St. Groth and Scheidegger, "Production of Monoclonal Antibodies: Strategy and Tactics," *J. Immunol. Methods* 35:1–21 (1980).

Sternberger et al., "The Unlabeled Antibody Enzyme Method of Immunohistochemistry: Preparation and Properties of Soluble Antigen–Antibody Complex (Horseradish Peroxidase–Antihorseradish Peroxidase) and its Use in Identification of Spirochetes," *J. Histochemistry and Cytochemistry* 18(5):315–333 (1970).

Superti–Furga et al., "Csk inhibition of c–Src activity requires both the SH2 and SH3 domains of Src," *EMBO J.* 12:2625–2634 (1993).

Tijssen, *Practice and Theory of Enzyme Immunoassays: Laboratory Techniques in Biochemistry and Molecular Biology*, vol. 15, Elsevier Science Publishers, Amsterdam, The Netherlands (1985) (Table of Contents Only).

Tokino et al., "Characterization of the Human," p. 57 (KIP2) gene: alternative splicing, insertion/deletion polymorphisms in VNTR sequences in the coding region, and mutational analysis. *Hum. Genet.* 97:625–631 (1996).

Ulmanen et al., "Transcription and Translation of Foreign Genes in *Bacillus subtilis* by the Aid of a Secretion Vector," *Journal of Bacteriology* 162:176–182 (1985).

Ward et al., "Construction and characterization of a series of multi–copy promoter–probe plasmid vectors for Streptomyces using the aminoglycoside phosphotransferase gene from Tn5 as indicator," *Mol. Gen. Genet.* 203:468–478 (1986).

Watson, "Drosophila WARTS– tumor suppressor and member of the myotonic dystrophy protein kinase family," *BioEssays* 17:673–676 (1995).

Wilchek and Jakoby, "The Literature on Affinity Chromatography," *Methods in Enzymology* 34:3–10 (1974).

Wolbring et al., "Inhibition of GTP–utilizing Enzymes by Tyrphostins," *J. Biol. Chem.* 269:22470–22472 (1994).

Xu et al., "Identifying tumor suppressors in genetic mosaics: The Drosophila lats gene encodes a putative protein kinase," *Development* 121:1053–1063 (1995).

Yang et al., "In Vivo and In Vitro Gene Transfer to Mammalian Somatic Cells by Particle Bombardment," *Proc. Natl. Acad. Sci. USA* 87:9568–9572 (1990).

Yoneda et al., "The Antiproliferative Effects of Tyrosine Kinase Inhibitors Tyrphostins on a Human Squamous Cell Carcinoma in Vitro and in Nude Mice," *Cancer Research* 51:4430–4435 (1991).

\* cited by examiner

FIG. 1A

```
Wart1_h    1                                              MKRSEKPEGYRQ   12

********. *..*** ******.*. **.*   ...... ..   ** .* .
Wart2_h    1   MRPKTFPATTYSGNSRQRLQEIREGLKQPSKSSVQGLPAGPNSDTSLDAKVLGSKDATRQ   60
Wart1_h   13   MRPKTFPASNYTVSSRQMLQEIRESLRNLSKPS-----DAAKAEHNM------SKMSTED   61

.*.* ****  .***.*** *******.  .* ...*** ****.* ** *..*  .
Wart2_h   61   QQQMRATPKFGPYQKALREIRYSLLPFANESGTS-AAAEVNRQMLQELVNAGCDQEMAGR  119
Wart1_h   62   PRQVRNPPKFGTHHKALQEIRNSLLPFANETNSSRSTSEVNPQMLQDLQAAGFDEDMVIQ  121

** * .******.*.****.* *** **.     * **. . .* .*.
Wart2_h  120   ALKQTGSRSIEAALEYISKMGYLDPRNEQIV----RVIKQT-SPGKGLMPTPVTRRPSFE  174
Wart1_h  122   ALQKTNNRSIEAAIEFISKMSYQDPRREQMAAAAARPINASMKPGN--VQQSVNRKQSWK  179

*. .*  . * * *  . ..  ...*. .. **      .*.         . *
Wart2_h  175   GTGDSFASYHQLSGTPY-EGPSFGADGPTALEEMPRP--------YVDY-------LFP-  217
Wart1_h  180   GSKESLVP--QRHGPPLAESVAYHSESPNSQTDVGRPLSGSGISAFVQAHPSNGQRVNPP  237

.* * *. .. **.*              *....*           *
Wart2_h  218   ------GVGPHGPGHQHQHPPKG----------------YGASVEAAGAHFPLQGAHYGR  255
Wart1_h  238   PPPQVRSVTPPPPPPRGQTPPPRGTTPPPPSWEPNSQTKRYSGNME------------YVI  285

... . ** **  .*    **. * *.*.* *              .
Wart2_h  256   PHL--LVPGE-PLGYGVQRSPSFQS--KTPPETG--GYASLPTKGQ-------------G  295
Wart1_h  286   SRISPVPPGAWQEGY---PPPPLNTSPMNPPNQGQRGISSVPVGRQPIIMQSSSKFNFPS  342

* **   .* . *      ***   ** .   *..  *. **  .
Wart2_h  296   GPPG----AGLA-F---------------PPPAAGLYVPHPHHKQAGPAAHQLHVLGSRS  335
Wart1_h  343   GRPGMQNGTGQTDFMIHQNVVPAGTVNRQPPP------PYPLTAANGQSPSALQTGGSAA  396

... * ***.. *.*** *..**... ..* ** .. * .* .*** .
Wart2_h  336   QV-FASDSPPQSLLTPSRNSLNVDLYELGSTSVQ-QWPAATLARRDSLQKPGLEAPPRAH  393
Wart1_h  397   PSSYTNGSIPQSMMVPNRNSHNMELYNISVPGLQTNWPQSSSAPAQSSPSSGHEIPTW--  454

.*. ** *.****.  *  *..  .....**  . ****.*.* * .****.***
Wart2_h  394   VAFRPDCPVPSRTNSFNSHQP---RPGPPGKAEPSLPAPNTVTAVTAAHILHPVKSVRVL  450
Wart1_h  455   ---QPNIPV--RSNSFNN--PLGNRASHSANSQPS---ATTVTAITPAPIQQPVKSMRVL  504

.** ***..*.**.*.* *   *.**       ..       *   .* **
Wart2_h  451   RPEPQTAVGPSHPAWVPAPAPAPAPAPAPAAEGLDAKEEHALALGGAGAFPLDVEYGGPD  510
Wart1_h  505   KPELQTALAPTHPSWIPQPIQTVQPSPFP-----EGTASNVTVMPPVAEAP---NYQGP-  555

********  ..  *  *. *. ...*. ** *.*  * ** . *
Wart2_h  511   RRCPPPPYPKHLLLRSKS-EWART1_HDLDSLC-AGMEQ--SLRAGPNEPEGGDKSRKS-AKGDK  565
Wart1_h  556   ----PPPYPKHLLHQNPSVPPYE--SISKPSKEDQPSL---PKE----DESEKSYENVDS  602

* *.****.***. ****.***.***** **** *************.*. **...*. r
Wart2_h  566   GGKDKKQIQTSPVPVRKNSRDEEKRESRIKSYSPYAFKFFMEQHVENVIKTYQQKVNRRL  625
Wart1_h  603   GDKEKKQITTSPITVRKNKKDEERRESRIQSYSPQAFKFFMEQHVENVLKSHQQRLHRKK  662
```

FIG. 1B

```
             ***  **   **    *.****.*  ******  ********************************
Wart2_h  626 QLEQEMAKAGLCEAEQEQMRKILYQKESNYNRLKRAKMDKSMFVKIKTLGIGAFGEVCLA 685
Wart1_h  663 QLENEMMRVGLSQDAQDQMRKMLCQKESNYIRLKRAKMDKSMFVKIKTLGIGAFGEVCLA 722

****  ****  *********  **************************.*********.*****
Wart2_h  686 CKVDTHALYAMKTLRKKDVLNRNQVAHVKAERDILAEADNEWVVKLYYSFQDKDSLYFVM 745
Wart1_h  723 RKVDTKALYATKTLRKKDVLLRNQVAHVKAERDILAEADNEWVVRLYYSFQDKDNLYFVM 782

**************  ***  *********  *.**********************  ****
Wart2_h  746 DYIPGGDMMSLLIRMEVFPEHLARFYIAELTLAIESVHKMGFIHRDIKPDNILIDLDGHI 805
Wart1_h  783 DYIPGGDMMSLLIRMGIFPESLARFYIAELTCAVESVHKMGFIHRDIKPDNILIDRDGHI 842

***************.*****  *  * *****. *. * * *.******* **.** .**
Wart2_h  806 KLTDFGLCTGFRWTHNSKYYQKGSHVRQDSMEPSDLWDDVSNCRCGDRLKTLEQRARKQH 865
Wart1_h  843 KLTDFGLCTGFRWTHDSKYYQSGDHPRQDSMDFSNEWGDPSSCRCGDRLKPLERRAARQH 902

********************  *********************************  **  ***.**
Wart2_h  866 QRCLAHSLVGTPNYIAPEVLLRKGYTQLCDWWSVGVILFEMLVGQPPFLAPTPTETQLKV 925
Wart1_h  903 QRCLAHSLVGTPNYIAPEVLLRTGYTQLCDWWSVGVILFEMLVGQPPFLAQTPLETQMKV 962

***. .****.* ******  ***  ***   ...  ***.****..******  .******.*  *
Wart2_h  926 INWENTLHIPAQVKLSPEARDLITKLCCSADHRLGRNGADDLKAHPFFSAIDFSSDIRKQ 985
Wart1_h  963 INWQTSLHIPPQAKLSPEASDLIIKLCRGPEDRLGKNGADEIKAHPFFKTIDFSSDLRQQ 1022

.*.*.* *.** ********  .*. *      ***   * ************
Wart2_h  986 PAPYVPTISHPMDTSNFDPVDEESPWNDASEGSTKAWDTLTS--PNNKHPEHAFYEFTFR 1043
Wart1_h 1023 SASYIPKITHPTDTSNFDPVDPDKLWSDDNEEENVN-DTLNGWYKNGKHPEHAFYEFTFR 1081

********.  ***    *    ...*. .*  .  ** *.       ***
Wart2_h 1044 RFFDDNGYPFRCPKPSGAEASQAESSDLESSDLVDQTEGCQ-----PVYV 1088
Wart1_h 1082 RFFDDNGYPYNYPKPIEYEYINSQGSEQQSDE-DDQNTGSEIKNRDLVYV 1130
```

FIG. 2A

```
Wart1_h    1                                                        MKRSEKPE    8
Wart_dm    1                                      MHPAGEKRGGRPNDKYTAEALES       23
Wart1_h    9   GYRQMRPKTFPASNYTVSSRQMLQEIRESLRNLSKPSDAAKAEHNMSKMSTEDPRQVRNP      68
Wart_dm   24   IKQDLTRFEVQNNHRNNQNYTPLRYTATNGRNDALTPDYHHAKQPMEPPPSASPAPDVVI     83
Wart1_h   69   PKFGTHHKALQEIRNSLLPFANETNSSRSTSEVNPQMLQDLQAAGFDEDMVIQALQKTNN    128
Wart_dm   84   PPPPAIVGQPGAGSISVSGVGVGVVGVANGRVPKMMTALMPNKLIRKPSIERDTASSHYL    143
Wart1_h  129   RSIEAAIEFISKMSYQDPRREQMAAAAARPINASMKPGNVQQSVNRKQSWKGSKESLVPQ    188

* .*.*   .              .  *.  *.*.* ** .  .* *                  *.*
Wart_dm  144   RCSPALDSGAGSSRSDSPHSHHTHQPSSRT-VGNPGGNGGFS---------------PSP    187
Wart1_h  189   RHGPPLAESV---------AYHSESPNSQTDVGRPLSGSGISAFVQAHPSNGQRVNPPPP    239

.  *.** ****  *.   ..*****   * **.         ** *
Wart_dm  188   SGFSEVAPPAPPPRNPTASS-AATPPPPV-PPTSQA--------YVKRR-----------    226
Wart1_h  240   PQVRSVTPP-PPPRGQTPPPRGTTPPPPSWEPNSQTKRYSGNMEYVISRISPVPPGAWQE    298

.*.**  *   .**  **  *        .*.*  *.          *.*     *
Wart_dm  227   ---SPALNNRPPAIAPPTQ--RGNS-------PVITQN-----------GLKNPQQQ---    260
Wart1_h  299   GYPPPPLNTSP--MNPPNQGQRGISSVPVGRQPIIMQSSSKFNFPSGRPGMQNGTGQTDF    356

. *    *. *    .*.*  *****  .   *  .*..        .*.***      *
Wart_dm  261   LTQQLKSLNLYPGGGSGAVV-EPPPPYLIQGGAGGAAPPP-------PPPSYTA-----S    307
Wart1_h  357   MIHQ----NVVP---AGTVNRQPPPPYPLTA-ANGQSPSALQTGGSAAPSSYTNGSIPQS    408

*                          ** .*.**     *****
Wart_dm  308   M------------------------QSRQSPTQSQQSDYRKSPSSG-------------    329
Wart1_h  409   MMVPNRNSHNMELYNISVPGLQTNWPQSSSAPAQS-------SPSSGHEIPTWQPNIPVR    461

** *  *...*  .. ***.         ***       *** .*
Wart_dm  330   ------------IYSATSAGSPSPITVSLPPAPLAKPQPRVYQARSQQPIIMQSVKSTQV    377
Wart1_h  462   SNSFNNPLGNRASHSANSQPSATTVT-AITPAPI-------------QQP-----VKSMRV   503

** ****.**  **   ..   *.    *...*. .*.*        * *.. *
Wart_dm  378   QKFVLQTAVAPQSPSSASASNSPVHVLAAPPSYPQKSAAVVQQQQQAAAAAHQQQHQHQQ    437
Wart1_h  504   LKPELQTALAPTHPSWIPQPIQTVQ----PSPFPEGTASNVTVMPPVAEAPNYQ------    553

*            ** *.*            .. .*
Wart_dm  438   SKPATPTTPPLVGLNSKPNCLEPPSYAKSMQAKAATVVQQQQQQQQQQQVQQQQVQQQQ    497
Wart1_h  554   ---------GP------------PPPYPK---------------------HLLHQ--    566

**.       ***.*
Wart_dm  498   QQQQQLQALRVLQAQAQRERDQRERERDQQKLANGNPGRQMLPPPPYQSNNNNNSEIKPP    557
Wart1_h  567   ----------------------------------NPS-----VPPYES----------   575

**...   *...*    ...* ..  * .*.                    **   .
Wart_dm  558   SCNNNNNIQISNSNLATTPPIPPAKYNNNSSNTGANSSGGSNGSTGTTASSSTSCKKIKHA    617
```

FIG. 2B

```
Wart1_h    576 --------ISKPSKEDQPSLPK---EDESEKSYENVDSGDKE-----------KKQITT 612

***  **   *.***.* **  .*************.***.**  **  **.***.**
Wart_dm    618 SPIPERKKISKEKEEERKEFRIRWART1_HSPQAFKFFMEQHIENVIKSYRQRTYRKNQLEKEMH 680
Wart1_h    613 SPITVRKN---KKDEERRESRIQSYSPQAFKFFMEQHVENVLKSHQQRLHRKKQLENEMM 669

.***....*..*****..********************.*..*.******..*..*.**
Wart_dm    678 KVGLPDQTQIEMRKMLNQKESNYIRLKRAKMDKSMFVKLKPIGVGAFGEVTLVSKIDTSN 740
Wart1_h    670 RVGLSQDAQDQMRKMLCQKESNYIRLKRAKMDKSMFVKIKTLGIGAFGEVCLARKVDTKA 729

***.*****.***.*******************.***.*********************
Wart_dm    738 HLYAMKTLRKADVLKRNQVAHVKAERDILAEADNNWVVKLYYSFQDKDNLYFVMDYIPGG 800
Wart1_h    730 -LYATKTLRKKDVLLRNQVAHVKAERDILAEADNEWVVRLYYSFQDKDNLYFVMDYIPGG 788

*.*****..***.*.********.****.*******************************
Wart_dm    798 DLMSLLIKLGIFEEELARFYIAEVTCAVDSVHKMGFIHRDIKPDNILIDRDGHIKLTDFG 860
Wart1_h    789 DMMSLLIRMGIFPESLARFYIAELTCAVESVHKMGFIHRDIKPDNILIDRDGHIKLTDFG 848

********.*****.*.*.*****.*..  ..  ** **** *.***
Wart_dm    858 LCTGFRWTHNSKYYQENGNHSRQDSMEPWEEYSENGP-------KPTVLERRRMRDHQRV 913
Wart1_h    849 LCTGFRWTHDSKYYQ-SGDHPRQDSMDFSNEWGDPSSCRCGDRLKP--LERRAARQHQRC 905

****************.*.****** *******.***********..*****.*****
Wart_dm    911 LAHSLVGTPNYIAPEVLERSGYTQLCDYWSVGVILYEMLVGQPPFLANSPLETQQKVINW 973
Wart1_h    906 LAHSLVGTPNYIAPEVLLRTGYTQLCDWWSVGVILFEMLVGQPPFLAQTPLETQMKVINW 965

. .******.**.**.***.**...****..**.*.*.***.***..*.*.*.*.
Wart_dm    971 EKTLHIPPQAELSREATDLIRRLCASADKRLGKS-VDEVKSHDFFKGIDFA-DMRKQKAP 1031
Wart1_h    966 QTSLHIPPQAKLSPEASDLIIKLCRGPEDRLGKNGADEIKAHPFFKTIDFSSDLRQQSAS 1025

*** * *************.**.*.*.  ..  ** *      *.*.***
Wart_dm    1029 YIPEIKHPTDTSNFDPVDPEKLRSNDSTMSSGDDVDQNDRTF-----------HGFFEFT 1080
Wart1_h    1026 YIPKITHPTDTSNFDPVDPDKLWSDDN-----EEENVND-TLNGWYKNGKHPEHAFYEFT 1079

******.
Wart_dm    1078 FRRFFDDK 1088
Wart1_h    1080 FRRFFDDN 1087
```

HUMAN ORTHOLOGUES OF WART

RELATED APPLICATIONS

This application is related to and claims priority to the U.S. Provisional Application Serial No. 60/072,023, filed on Jan. 21, 1998, by Plowman et al., and entitled "HUMAN ORTHOLOGUES OF WART", which is hereby incorporated by reference herein in its entirety, including any drawings.

FIELD OF THE INVENTION

The present invention relates in part to protein kinases. In particular, the invention concerns the identification of protein kinase proteins which are human orthologues of the drosophila WART gene (hWART).

BACKGROUND OF THE INVENTION

The following description is provided to aid in understanding the invention, but is not admitted to describe or constitute prior art to the invention.

Cellular signal transduction is a fundamental mechanism whereby extracellular stimuli are relayed to the interior of cells and thereby regulate diverse cellular processes. One of the key biochemical mechanisms of signal transduction involves the reversible phosphorylation of proteins. Phosphorylation of polypeptides regulates the activity of mature proteins by altering their structure and function. Phosphate most often resides on the hydroxyl moiety of serine, threonine, or tyrosine amino acids in proteins.

Enzymes that mediate phosphorylation of cellular effectors generally fall into two classes. The first class consists of protein kinases which transfer a phosphate moiety from nucleotide triphosphates to protein substrates. The second class consists of protein phosphatases which hydrolyze phosphate moieties from phosphoryl protein substrates. The converse functions of protein kinases and protein phosphatases balance and regulate the flow of signals in signal transduction processes.

Protein kinases are generally divided into two classes: receptor and non-receptor type proteins. Protein kinases may also be divided into three classes based upon the amino acids they act upon: (1) Some catalyze the addition or hydrolysis of phosphate on serine or threonine only; (2) some catalyze the addition or hydrolysis of phosphate on tyrosine only; and (3) some catalyze the addition or hydrolysis of phosphate on serine, threonine, and tyrosine.

Altered protein kinase activity has been associated with multiple abnormal cellular functions, including increased cell proliferation. Increased cell proliferation can result from at least two cellular events: (i) mutation, chromosome translocation, or gene amplification of proto-oncogenes (Bishop, Cell 64:235–248, 1991), or (ii) inactivation, loss by mutation, chromosomal loss, mitotic recombination, or gene conversion of tumor suppressor genes (Lasko et al., Ann Rev Genet 25:281–314).

A large number of potential tumor suppressor genes have been isolated from Drosophila melanogaster, a species of fruit fly. Watson et al., J. Cell Sci. 18:19–33, 1994. Potential tumor suppressor genes are identified in this organism by first deleting, obstructing, or mutating a gene, and then detecting over-proliferative cell growth of specific tissues in dissected larvae and pupae. Xu et al., Development 121:1053–1063, 1995. This organism provides an ideal system for identifying potential tumor suppressor genes as it reproduces rapidly and its genome is readily manipulated by persons skilled in the art.

An example of a putative tumor suppressor gene, identified in Drosophila is the wts gene. Loss or inactivation of both copies of the wts gene results in the growth of tumors on the legs and wings of the flies. Bryant et al., Development 1993 Supplement: 239–249, 1993. The large size of these tumors suggests that the cells undergo more divisions than normal. Id. In addition, the rounded shape of the tumors suggests that the division of the mutant cells is not preferentially oriented. Id. These observations taken together with the increased thickness of the cuticles around the mutant cells suggest that the wts gene regulates cell adhesion, cell contact inhibition, and/or cell boundary recognition in Drosophila.

Several of the genes characterized as potential tumor suppressors in Drosophila are cloned. In particular, the wts gene contains a region that bears sequence similarity to the catalytic regions of mammalian non-receptor serine/threonine protein kinases. Watson, BioEssays 17:673–676, 1995. However, the human orthologues of the drosophila wts gene have not been reported.

SUMMARY OF THE INVENTION

The invention relates in part to novel human orthologues of the Drosophila wts gene (hWARTs). The Drosophila wts gene encodes a non-receptor serine/threonine kinase. The properties of the human orthologues are described herein. The present invention concerns polypeptides of hWART, nucleic acids encoding such polypeptides, cells, tissues and animals containing such nucleic acids, antibodies to the polypeptides, assays utilizing the polypeptides, and methods relating to all of the foregoing.

The term "orthologue" as used herein, refers to a gene that is more c related, in terms of nucleic acid sequence, to another gene than a gene which is a homologue. In the context of this invention, "homologous" indicates that the nucleotide sequences of two genes and/or the sequences of the gene products (e.g., amino acid sequences) have significant similarity, and that the gene products perform a similar cellular function. Thus, two homologous genes may have sequences which have 50, 60, 70, 80, 90, or greater percent nucleotide sequence identity. By "closely related" in the context of this invention, it is meant nucleic acid sequences that have greater than 90% identity.

The hWARTS genes encode proteins that are potential drug targets for controlling aberrant cell proliferation. Unlike their Drosophila ortholog, the hWARTS genes may not function as tumor suppressor genes. While their mRNA is absent from most normal cells they are abundantly expressed in many types of tumor cells. However, based on the high degree of sequence identity in the catalytic and non-catalytic regions between the hWART proteins and the Drosophila wts, it is likely that the hWART genes are involved in regulating cell adhesion, cell contact inhibition, and/or cell boundary recognition, and in regulation of signal transduction pathways related to cell proliferation.

Thus, in a first aspect, the invention features an isolated, enriched, or purified nucleic acid molecule encoding an hWART polypeptide.

By "isolated" in reference to nucleic acid it is meant a polymer of 14, 17, 21 or more nucleotides conjugated to each other, including DNA or RNA that is isolated from a natural source or that is synthesized. The isolated nucleic acid of the present invention is unique in the sense that it is not found in a pure or separated state in nature. Use of the term "isolated" indicates that a naturally occurring sequence has been removed from its normal cellular (i.e., chromosomal) environment. Thus, the sequence may be in a cell-free solution or placed in a different cellular environment. The term does not imply that the sequence is the only nucleotide sequence present, but that it is essentially free (about 90–95% pure at least) of non-nucleotide material naturally associated with it and thus is meant to be distinguished from isolated chromosomes.

By the use of the term "enriched" in reference to nucleic acid it is meant that the specific DNA or RNA sequence constitutes a significantly higher fraction (2–5 fold) of the total DNA or RNA present in the cells or solution of interest than in normal or diseased cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

The term "significant" here is used to indicate that the level of increase is useful to the person making such an increase, and generally means an increase relative to other nucleic acids of about at least 2 fold, more preferably at least 5 to 10 fold or even more. The term also does not imply that there is no DNA or RNA from other sources. The other source DNA may, for example, comprise DNA from a yeast or bacterial genome, or a cloning vector such as pUC19. This term distinguishes the sequence from naturally occurring enrichment events, such as viral infection, or tumor type growths, in which the level of one mRNA may be naturally increased relative to other species of mRNA. That is, the term is meant to cover only those situations in which a person has intervened to elevate the proportion of the desired nucleic acid.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level this level should be at least 2–5 fold greater, e.g., in terms of mg/ml). Individual clones isolated from a cDNA library may be purified to electrophoretic homogeneity. The claimed DNA molecules obtained from these clones can be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^6$-fold purification of the native message. Thus, purification of at least one order of magnitude, preferably two or three orders, and more preferably four or five orders of magnitude is expressly contemplated. The term is also chosen to distinguish clones already in existence which may encode hWARTs but which have not been isolated from other clones in a library of clones. Thus, the term covers clones encoding hWART which are isolated from other non-hWART clones.

The term "nucleic acid molecule" describes a polymer of deoxyribonucleotides (DNA) or ribonucleotides (RNA). The nucleic acid molecule may be isolated from a natural source by cDNA cloning or subtractive hybridization or synthesized manually. The nucleic acid molecule may be synthesized manually by the triester synthetic method or by using an automated DNA synthesizer.

The term "cDNA cloning" refers to hybridizing a small nucleic acid molecule, a probe, to genomic cDNA. The probe hybridizes (binds) to complementary sequences of cDNA.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus if a nucleic acid sequence contains the following sequence of bases, thymine, adenine, guanine and cytosine, a "complement" of this nucleic acid molecule would be a molecule containing adenine in the place of thymine, thymine in the place of adenine cytosine in the place of guanine, and guanine in the place of cytosine. Because the complement can contain a nucleic acid sequence that forms optimal interactions with the parent nucleic acid molecule, such a complement can bind with high affinity to its parent molecule.

The term "hybridize" refers to a method of interacting a nucleic acid sequence with a DNA or RNA molecule in solution or on a solid support, such as nitrocellulose, nylon or some combination of these materials. If a nucleic acid sequence binds to the DNA or RNA molecule with high affinity, it is said to "hybridize" to the DNA or RNA molecule. The strength of the interaction between the probing sequence and its target can be assessed by varying the stringency of the hybridization conditions. Under highly stringent hybridization conditions only highly complementary nucleic acid sequences hybridize. Preferably, such conditions prevent hybridization of nucleic acids having one or two mismatches out of 20 contiguous nucleotides.

Various low or high stringency hybridization conditions may be used depending upon the specificity and selectivity desired. Stringency is controlled by varying salt or denaturant concentrations. Examples of hybridization conditions are shown in the examples described herein. High stringent conditions may mean conditions that are at least as stringent as the following: hybridization in 50% formamide, 5×SSC, 50 mM $NaH_3PO_4$, pH 6.8, 0.5% SDS, 0.1 mg/mL sonicated salmon sperm DNA, and 5×Denhart solution at 42 C. overnight; washing with 2×SSC, 0.1% SDS at 45 C.; and washing with 0.2×SSC, 0.1% SDS at 45 C. Those skilled in the art will recognize how such conditions can be varied to vary specificity and selectivity.

cDNAs are molecules that may be reverse-transcribed from fragments of message RNA from a genomic source. These fragments form a cDNA library of nucleic acid molecules. cDNA libraries are constructed from natural sources such as mammalian blood, semen, or tissue.

The term "subtractive hybridization" refers to a method similar to cDNA cloning except that cDNA prepared from mRNA in unstimulated cells is added to mRNA in stimulated or different types of cells. cDNA/mRNA can then be precipitated to enrich the mRNA specific to the stimulation signal or different cell type.

The term "hWART nucleic acid molecule" as used herein refers to a nucleic acid molecule that encodes an hWART polypeptide. hWART nucleic acid molecules can be identified by hybridization procedures and cloning procedures as described herein.

An hWART polypeptide can be encoded by a full-length nucleic acid sequence or any portion of the full-length nucleic acid sequence. In preferred embodiments, the isolated nucleic acid comprises, consists essentially of, or consists of a nucleic acid sequence set forth in SEQ ID NO:1, or SEQ ID NO:2, a nucleic acid sequence that hybridizes to the nucleic acid sequence set forth in SEQ ID NO:1, or SEQ ID NO:2, or a functional derivative (as defined below) of either of the foregoing. The nucleic acid may be isolated from a natural source by cDNA cloning or subtractive hybridization; the natural source may be mammalian (human) blood, semen, or tissue and the nucleic acid may be synthesized by the triester or other method or by using an automated DNA synthesizer.

The term "mammalian" refers to such organisms as mice, rats, rabbits, goats, more preferably monkeys and apes, and most preferably humans.

In other preferred embodiments, the nucleic acid molecule of the invention comprises a nucleotide sequence that (a) encodes a polypeptide having the full length amino acid sequence set forth in SEQ ID NO:3 or SEQ ID NO:4; (b) is the complement of the nucleotide sequence of (a); (c) hybridizes under highly stringent conditions to the nucleotide molecule of (a) and encodes a naturally occurring hWART polypeptide; (d) encodes an hWART polypeptide having the full length amino acid sequence of the sequence set forth in SEQ ID NO:3 or SEQ ID NO:4, except that it lacks one or more of the following segments of amino acid residues: 12–45, 55–151, 236–377, 404–520, 555–559, 601–702, 691–998, 1011–1086 of SEQ ID NO:3, or 1–33, 43–139, 342–466, 467–480, 514–518, 974–1048 of SEQ ID NO:4; (e) is the complement of the nucleotide sequence of (d); (f) encodes a polypeptide having the amino acid sequence set forth in SEQ ID NO:3 or SEQ ID NO:4 from amino acid residues 12–45, 55–151, 236–377, 404–520, 555–559, 601–702, 691–998, 1011–1086 of SEQ ID NO:3, or 1–33, 43–139, 342–466, 467–480, 514–518, 974–1048 of SEQ ID NO:4; (g) is the complement of the nucleotide sequence of (f); (h) encodes a polypeptide having the full length amino acid sequence set forth in SEQ ID NO:3 or SEQ ID NO:4, except that it lacks one or more of the domains selected from the group consisting of an N-terminal domain, a catalytic domain, and a C-terminal domain; or (i) is the complement of the nucleotide sequence of (h). The nucleic acid molecule of the invention is isolated, enriched, or purified from, preferably, a mammal, or most preferably from a human.

In yet other preferred embodiments, the nucleic acid is an isolated conserved or unique region, for example those useful for the design of hybridization probes to facilitate identification and cloning of additional polypeptides, or for the design of PCR probes to facilitate cloning of additional polypeptides.

By "conserved nucleic acid regions", it is meant regions present on two or more nucleic acids encoding an hWART polypeptide, to which a particular nucleic acid sequence can hybridize under lower stringency conditions. Examples of lower stringency conditions suitable for screening for nucleic acids encoding hWARTs polypeptides are provided in Abe, et al. J. Biol. Chem. 19:13361, 1992 (hereby incorporated by reference herein in its entirety, including any drawings). Preferably, conserved regions differ by no more than 5 out of 20 contiguous nucleotides.

By "unique nucleic acid region" it is meant a sequence present in a full length nucleic acid coding for an hWART polypeptide that is not present in a sequence coding for any other known naturally occurring polypeptide. Such regions preferably comprise 14, 17, 21 or more contiguous nucleotides present in the full length nucleic acid encoding an hWART polypeptide. In particular, a unique nucleic acid region is preferably of human origin.

In yet another aspect, the invention relates to a nucleic acid vector comprising a nucleic acid molecule encoding an hWART polypeptide and a promoter element effective to initiate transcription in a host cell.

The term "nucleic acid vector" relates to a single or double stranded circular nucleic acid molecule that can be transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that the restriction enzymes operate upon are readily available to those skilled in the art. A nucleic acid molecule of the invention can be inserted into a vector by cutting the vector with restriction enzymes and ligating the two pieces together.

Many techniques are available to those skilled in the art to facilitate transformation or transfection of the expression construct into a prokaryotic or eukaryotic organism. The terms "transformation" and "transfection" refer to methods of inserting an expression construct into a cellular organism. These methods involve a variety of techniques, such as treating the cells with high concentrations of salt, an electric field, or detergent, to render the host cell outer membrane or wall permeable to nucleic acid molecules of interest.

The term "promoter element" describes a nucleotide sequence that is incorporated into a vector that, once inside an appropriate cell, can facilitate transcription factor and/or polymerase binding and subsequent transcription of portions of the vector DNA into mRNA. The promoter element precedes the 5' end of the hWART nucleic acid molecule such that the latter is transcribed into mRNA. Host cell machinery then translates mRNA into a polypeptide.

Those skilled in the art would recognize that a nucleic acid vector can contain many other nucleic acid elements besides the promoter element and the hWART nucleic acid molecule. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, periplasm or peroxisome localization signals, or signals useful for polypeptide purification.

The invention also features a nucleic acid probe for the detection of a nucleic acid encoding an hWART polypeptide in a sample.

The term "nucleic acid probe" refers to a nucleic molecule that is complementary to and can bind a nucleic acid sequence encoding the amino acid sequence substantially similar to that set forth in SEQ ID NO:3, or SEQ ID NO:4.

In preferred embodiments, the nucleic acid probe hybridizes to nucleic acid molecules encoding at least 46 contiguous amino acids of the sequences set forth in SEQ ID NO:3, SEQ ID NO:4, or a functional derivative thereof. Various low or high stringency hybridization conditions may be used depending upon the specificity and selectivity desired. Under highly stringent hybridization conditions only highly complementary nucleic acid sequences hybridize. Preferably, such conditions prevent hybridization of nucleic acids having 1 or 2 mismatches out of 20 contiguous nucleotides.

Methods for using the probes include detecting the presence or amount of hWART RNA in a sample by contacting the sample with a nucleic acid probe under conditions such that hybridization occurs and detecting the presence or amount of the probe bound to hWART RNA. The nucleic acid duplex formed between the probe and a nucleic acid sequence coding for an hWART polypeptide may be used in the identification of the sequence of the nucleic acid detected (for example see, Nelson et al., in Nonisotopic DNA Probe Techniques, p. 275 Academic Press, San Diego (Kricka, ed., 1992) hereby incorporated by reference herein in its entirety, including any drawings). Kits for performing such methods may be constructed to include a container having disposed therein a nucleic acid probe.

The invention also features a nucleic acid molecule as set forth in SEQ ID NO:1 or SEQ ID NO:2 or fragments thereof, comprising one or more regions that encode an hWART polypeptide or an hWART domain polypeptide, where the hWART polypeptide or the hWART domain polypeptide is fused to a non-WART polypeptide. Such fused polypeptides include, for example, but are not limited to, a GST-fusion protein.

The invention also features recombinant nucleic acid, preferably in a cell or an organism. The recombinant nucleic acid may contain a sequence set forth in SEQ ID NO:1, SEQ ID NO:2, or a functional derivative thereof and a vector or a promoter effective to initiate transcription in a host cell. The recombinant nucleic acid can alternatively contain a transcriptional initiation region functional in a cell, a sequence complimentary to an RNA sequence encoding an hWART polypeptide and a transcriptional termination region functional in a cell.

Another aspect of the invention relates to a recombinant cell or tissue comprising a nucleic acid molecule encoding an hWART polypeptide. The recombinant cell may comprise a nucleic acid molecule encoding either an hWART polypeptide; an hWART domain polypeptide; or an hWART polypeptide or hWART domain polypeptide fused to a non-WART polypeptide.

The term "recombinant organism" refers to an organism that has a new combination of genes or nucleic acid molecules. A new combination of genes or nucleic acid molecules can be introduced to an organism using a wide array of nucleic acid manipulation techniques available to those skilled in the art.

The term "organism" relates to any living being comprised of a least one cell. An organism can be as simple as one eukaryotic cell or as complex as a mammal. Therefore, a recombinant organism can also be a recombinant cell.

The recombinant cell can be a eukaryotic or prokaryotic organism.

The term "eukaryote" refers to an organism comprised of cells that contain a nucleus. Eukaryotes are differentiated from "prokaryotes" which do not have a nucleus and lack other cellular structures found in eukaryotes, such as mitochondria and endoplasmic reticulum. Prokaryotes include unicellular organisms, such as bacteria while eukaryotes are represented by yeast, invertebrates, and vertebrates.

The recombinant cell can harbor a nucleic acid vector that is extragenomic. The term "extragenomic" refers to a nucleic acid vector which does not insert into the cell genome. Many nucleic acid vectors are designed with their own origins of replication allowing them to utilize the recombinant cell replication machinery to copy and propagate the vector nucleic acid sequence. These vectors are small enough that they are not likely to harbor nucleic acid sequences homologous to genomic sequences of the recombinant cell. Thus these vectors replicate independently of the host genome and do not recombine with or integrate into the genome.

A recombinant cell can harbor a portion of a nucleic acid vector in an intragenomic fashion. The term "intragenomic" defines a nucleic acid construct that is incorporated within the cell genome. Multiple nucleic acid vectors available to those skilled in the art contain nucleic acid sequences that are homologous to nucleic acid sequences in a particular organism's genomic DNA. These homologous sequences will result in recombination events that integrate portions of the vector into the genomic DNA. Those skilled in the art can control which nucleic acid sequences of the vector are integrated into the cell genome by flanking the portion to be incorporated into the genome with homologous sequences in the vector.

Another aspect of the invention features an isolated, enriched, or purified hWART polypeptide.

By "hWART polypeptide" it is meant an amino acid sequence substantially similar to the sequence shown in SEQ ID NO:3, SEQ ID NO:4, or fragments thereof. A sequence that is substantially similar will preferably have at least 90% identity (more preferably at least 95% and most preferably 99–100%) to the sequence of SEQ ID NO:3 or SEQ ID NO:4.

The hWART polypeptides of the present invention preferably have a substantially similar biological activity to the proteins encoded by the full length nucleic acid sequence set forth in SEQ ID NO:1 or SEQ ID NO:2, or to the proteins with amino acid sequence set forth in SEQ ID NO:3 or SEQ ID NO:4. By "biological activity" it is meant an activity of the hWART protein in a cell. The biological activity of the hWART is related to some of the activities of the cell which include, but are not limited to, cell proliferation motogenesis, metastasis, tumor escape, cell adhesion, transformation, or apoptosis.

By "identity" is meant a property of sequences that measures their similarity or relationship. Identity is measured by dividing the number of identical residues in the two sequences by the total number of residues and multiplying the product by 100. Thus, two copies of exactly the same sequence have 100% identity, but sequences that are less highly conserved and have deletions, additions, or replacements have a lower degree of identity. Those skilled in the art will recognize that several computer programs are available for determining sequence identity.

By "isolated" in reference to a polypeptide is meant a polymer of 6, 12, 18 or more amino acids conjugated to each other, including polypeptides that are isolated from a natural source or that are synthesized. The isolated polypeptides of the present invention are unique in the sense that they are not found in a pure or separated state in nature. Use of the term "isolated" indicates that a naturally occurring sequence has been removed from its normal cellular environment. Thus, the sequence may be in a cell-free solution or placed in a different cellular environment. The term does not imply that the sequence is the only amino acid chain present, but that it is essentially free (about 90–95% pure at least) of material naturally associated with it.

By the use of the term "enriched" in reference to a polypeptide it is meant that the specific amino acid sequence constitutes a significantly higher fraction (2–5 fold) of the total of amino acids present in the cells or solution of interest than in normal or diseased cells or in the cells from which the sequence was taken. This could be caused by a person by preferential reduction in the amount of other amino acids present, or by a preferential increase in the amount of the specific amino acid sequence of interest, or by a combination of the two. However, it should be noted that "enriched" does not imply that there are no other amino acid sequences present, just that the relative amount of the sequence of interest has been significantly increased. The term significant here is used to indicate that the level of increase is useful to the person making such an increase, and generally means an increase relative to other amino acids of about at least 2 fold, more preferably at least 5 to 10 fold or even more. The term also does not imply that there is no amino acid from other sources. The other source amino acid may, for example, comprise amino acid encoded by a yeast or bacterial genome, or a cloning vector such as pUC19. The term is meant to cover only those situations in which a person has intervened to elevate the proportion of the desired nucleic acid.

It is also advantageous for some purposes that an amino acid sequence be in purified form. The term "purified" in reference to a polypeptide does not require absolute purity (such as a homogeneous preparation); instead, it represents an indication that the sequence is relatively purer than in the natural environment (compared to the natural level this level should be at least 2–5 fold greater, e.g., in terms of mg/mL. Purification of at least one order of magnitude, preferably two or three orders, and more preferably four or five orders of magnitude is expressly contemplated. The substance is preferably free of contamination at a functionally significant level, for example 90%, 95%, or 99% pure.

In another aspect, the invention features an isolated, enriched, or purified hWART polypeptide fragment.

By "hWART polypeptide fragment" it is meant an amino acid sequence that is less than the full-length amino acid sequence. The full-length amino acid sequences of hWART1 and hWART2 are shown in SEQ ID NO:3 and SEQ ID NO:4. Examples of fragments include hWART domains, hWART mutants and hWART-specific epitopes.

By "hWART domain" it is meant a portion of the hWART polypeptide having homology to amino acid sequences from one or more known proteins wherein the sequence predicts some common function, interaction or activity. Well known examples of domains are the SH2 (Src Homology 2) domain (Sadowski, et al, Mol. Cell. Biol. 6:4396, 1986; Pawson and Schlessinger, Curr. Biol. 3:434, 1993), the SH3 domain (Mayer, et al, Nature 332:272, 1988; Pawson and Schlessinger, Curr. Biol. 3:434, 1993), and pleckstrin (PH) domain (Ponting, TIBS 21:245, 1996; Haslam, et al, Nature 363:309, 1993), all of which are domains that mediate protein:protein interaction or protein:lipid interaction, and the kinase catalytic domain (Hanks and Hunter, FASEB J 9:576–595, 1995). Computer programs designed to detect such homologies are well known in the art. The relative homology is at least 20%, more preferably at least 30% and most preferably at least 35%.

By "hWART mutant" it is meant an hWART polypeptide which differs from the native sequence in that one or more amino acids have been changed, added or deleted. Changes in amino acids may be conservative or non-conservative. By "conservative" it is meant the substitution of an amino acid for one with similar properties such as charge, hydrophobicity, structure, etc. Examples of polypeptides encompassed by this term include, but are not limited to, (1) chimeric proteins which comprise a portion of an hWART polypeptide sequence fused to a non-hWART polypeptide sequence, for example, a polypeptide sequence of hemmaglutinin (HA), (2) hWART proteins lacking a specific domain, for example the catalytic domain, and (3) hWART proteins having a point mutation. An hWART mutant will retain some useful function such as, for example, binding to a natural binding partner, catalytic activity, or the ability to bind to an hWART specific antibody (as defined below).

By "hWART-specific epitope" it is meant a sequence of amino acids that is both antigenic and unique to an hWART polypeptide. An hWART-specific epitope can be used to produce hWART-specific antibodies, as more fully described herein. Particularly preferred epitopes are shown in the Examples section below.

By "recombinant hWART polypeptide" it is meant to include a polypeptide produced by recombinant DNA techniques such that it is distinct from a naturally occurring polypeptide either in its location (e.g., present in a different cell or tissue than found in nature), purity or structure. Generally, such a recombinant polypeptide will be present in a cell in an amount different from that normally observed in nature.

The polypeptide of the invention comprises an amino acid sequence having (a) the full length amino acid sequence set forth in SEQ ID NO:3 or SEQ ID NO:4; (b) the full length amino acid sequence of the sequence set forth in SEQ ID NO:3 or SEQ ID NO:4, except that it lacks one or more of the following segments of amino acid residues:12–45, 55–151, 236–377, 404–520, 555–559, 601–702, 691–998, 1011–1086 of SEQ ID NO:3, or 1–33, 43–139, 342–466, 467–480, 514–518, 974–1048 of SEQ ID NO:4; (c) the amino acid sequence set forth in SEQ ID NO:3 or SEQ ID NO:4 from amino acid residues 12–45, 55–151, 236–377, 404–520, 555–559, 601–702, 691–998, 1011–1086 of SEQ ID NO:3, or 1–33, 43–139, 342–466, 467–480, 514–518, 974–1048 of SEQ ID NO:4; or (d) the full length amino acid sequence set forth in SEQ ID NO:3 or SEQ ID NO:4 except that it lacks one or more of the domains selected from the group consisting of an N-terminal domain, a catalytic domain, and a C-terminal domain.

In yet another aspect, the invention features an antibody (e.g., a monoclonal or polyclonal antibody), or antibody fragment, having specific binding affinity to an hWART polypeptide or hWART polypeptide fragment.

By "specific binding affinity" is meant that the antibody binds to target (hWART) polypeptides with greater affinity than it binds to other polypeptides under specified conditions. Antibodies having specific binding affinity to an hWART polypeptide may be used in methods for detecting the presence and/or amount of an hWART polypeptide in a sample by contacting the sample with the antibody under conditions such that an immunocomplex forms and detecting the presence and/or amount of the antibody conjugated to the hWART polypeptide. Diagnostic kits for performing such methods may be constructed to include a first container containing the antibody and a second container having a conjugate of a binding partner of the antibody and a label, such as, for example, a radioisotope. The diagnostic kit may also include notification of an FDA approved use and instructions therefor.

The term "polyclonal" refers to antibodies that are heterogenous populations of antibody molecules derived from the sera of animals immunized with an antigen or an antigenic functional derivative thereof. For the production of polyclonal antibodies, various host animals may be immunized by injection with the antigen. Various adjuvants may be used to increase the immunological response, depending on the host species.

"Monoclonal antibodies" are substantially homogenous populations of antibodies to a particular antigen. They may be obtained by any technique which provides for the production of antibody molecules by continuous cell lines in culture. Monoclonal antibodies may be obtained by methods known to those skilled in the art. See, for example, Kohler, et al., Nature 256:495–497 (1975), and U.S. Pat. No. 4,376, 110.

The term "antibody fragment" refers to a portion of an antibody, often the hypervariable region and portions of the surrounding heavy and light chains, that displays specific binding affinity for a particular molecule. A hypervariable region is a portion of an antibody that physically binds to the polypeptide target.

In another aspect, the invention features a hybridoma which produces an antibody having specific binding affinity to an hWART polypeptide. By "hybridoma" is meant an immortalized cell line which is capable of secreting an antibody, for example an hWART antibody. In preferred embodiments the hWART antibody comprises a sequence of amino acids that is able to specifically bind an hWART polypeptide.

The invention features a method for identifying human cells containing an hWART polypeptide, or a related sequence. The method involves identifying the novel polypeptide in human cells using techniques that are routine and standard in the art, such as those described herein for identifying hWART polypeptides (e.g., cloning, Southern or Northern blot analysis, in situ hybridization, PCR amplification, etc.).

The invention also features methods of screening cells for natural binding partners of hWART polypeptides. By "natural binding partner" it is meant a protein that interacts with an hWART polypeptide. Binding partners include ligands, agonists, antagonists and downstream signaling molecules such as adaptor proteins and may be identified by techniques well known in the art such as co-immunoprecipitation or by using, for example, a two-hybrid screen. (Fields and Song, U.S. Pat. No. 5,283,173, issued Feb. 1, 1994 and, incorporated be reference herein.) The present invention also features the purified, isolated or enriched versions of the polypeptides identified by the methods described above.

In another aspect, the invention provides a method for identifying a substance capable of modulating hWART activity comprising the steps of (a) contacting an hWART polypeptide with a test substance; and (b) determining whether the substance alters the activity of said polypeptide.

The invention also features another method of identifying substances capable of modulating the function of an hWART polypeptide. The method comprises the following steps: (a) expressing an hWART polypeptide in cells; (b) adding a compound to the cells; and (c) monitoring a change or an absence of a change in cell phenotype, cell proliferation, catalytic activity of the hWART polypeptide, and binding a natural binding partner.

The term "compound" includes small organic molecules including, but not limited to, oxindolinones, quinazolines, tyrphostins, quinoxalines, and those contained within extracts from natural sources. Examples of such compounds are included in section XIII, below.

The term "function" refers to the cellular role of a serine-threonine protein kinase. The serine-threonine protein kinase family includes members that regulate many steps in signaling cascades, including cascades controlling cell growth, migration, differentiation, gene expression, muscle contraction, glucose metabolism, cellular protein synthesis, and regulation of the cell cycle.

The term "modulates" refers to the ability of a compound to alter the function of a protein kinase. A modulator preferably activates the catalytic activity of a protein kinase, more preferably activates or inhibits the catalytic activity of a protein kinase depending on the concentration of the compound exposed to the protein kinase, or most preferably inhibits the catalytic activity of a protein kinase.

The term "catalytic activity", in the context of the invention, defines the ability of a protein kinase to phosphorylate a substrate. Catalytic activity can be measured, for example, by determining the amount of a substrate converted to a product as a function of time. Phosphorylation of a substrate occurs at the active-site of a protein kinase. The active-site is normally a cavity in which the substrate binds to the protein kinase and is phosphorylated.

The term "substrate" as used herein refers to a molecule that is phoshorylated by or directly interacts with the protein kinase. The substrate is preferably a peptide and more preferably a protein. In relation to the protein kinase RAF, preferred substrates are MEK and the MEK substrate MAPK.

The term "activates" refers to increasing the cellular function of a protein kinase. The protein kinase function is preferably the interaction with a natural binding partner or catalytic activity.

The term "inhibit" refers to decreasing the cellular function of a protein kinase. The protein kinase function is preferably the interaction with a natural binding partner or catalytic activity.

The term "modulates" also refers to altering the function of a protein kinase by increasing or decreasing the probability that a complex forms between a protein kinase and a natural binding partner. A modulator preferably increases the probability that such a complex forms between the protein kinase and the natural binding partner, more preferably increases or decreases the probability that a complex forms between the protein kinase and the natural binding partner depending on the concentration of the compound exposed to the protein kinase, and most preferably decreases the probability that a complex forms between the protein kinase and the natural binding partner.

The term "complex" refers to an assembly of at least two molecules bound to one another. Signal transduction complexes often contain at least two protein molecules bound to one another, either transiently or in succession. For instance, a receptor protein tyrosine kinase, GRB2, SOS, and RAF sequentially interact in response to a mitogenic ligand.

The term "expressing" as used herein refers to the production of an hWART polypeptide from a nucleic acid vector containing an hWART gene within a cell. The nucleic acid vector is transfected into cells using well known techniques in the art as described herein.

The term "adding" as used herein refers to administering a solution comprising a compound to the medium bathing cells. The solution comprising the compound can also comprise an agent, such as dimethyl sulfoxide, which facilitates the uptake of the compound into the cells.

The term "monitoring" refers to observing the effect of adding the compound to the cells of the method. The effect can be manifested in a change in cell phenotype, cell proliferation, protein kinase catalytic activity, or in the interaction between a protein kinase and a natural binding partner.

The term "cell phenotype" refers to the outward appearance of a cell or tissue or the function of the cell or tissue. Examples of cell or tissue phenotype are cell size (reduction or enlargement), cell proliferation (increased or decreased numbers of cells), cell differentiation (a change or absence of a change in cell shape), cell survival, apoptosis (cell death), or the utilization of a metabolic nutrient (e.g., glucose uptake). Changes or the absence of changes in cell phenotype are readily measured by techniques known in the art.

The term "cell proliferation" refers to the rate at which a group of cells divides. The number of cells growing in a vessel can be quantitated by a person skilled in the art when that person visually counts the number of cells in a defined area using a comon light microscope. Alternatively, cell proliferation rates can be quantitated by laboratory apparatae that optically measure the density of cells in an appropriate medium.

The method can utilize any of the molecules disclosed in the invention. These molecules include nucleic acid molecules encoding hWART polypeptides, nucleic acid vectors, recombinant cells, polypeptides, or antibodies of the invention.

Substances identified as modulators of hWART activity can be used to study the effects of hWART modulation in animal models of cell proliferative disorders. For example, inhibitors of hWART activity can be tested as treatments for cell proliferative disorders such as leukemia or lymphoma using subcutaneous xenograph models in mice.

In a preferred embodiment, the invention provides a method for treating or preventing an abnormal condition by administering a compound which is a modulator of hWART function in vitro. The abnormal condition preferably involves abnormality in hWART signal transduction pathway, and most preferably is cancer. Such compounds preferably show positive results in one or more in vitro assays for an activity corresponding to treatment of the disease or disorder in question (such as the assays described in example 9 below). Examples of substances that can be screened for favorable activity are provided in section XIII below.

The summary of the invention described above is non-limiting and other features and advantages of the invention will be apparent from the following detailed description, and from the claims.

BRIEF DESCRIPTION OF THE FIGURES

FIG. 1 is a sequence alignment of the hWART1 (SEQ ID NO:3) and hWART2 (SEQ ID NO:4) amino acid sequences.

FIG. 2 is a sequence alignment of the hWART1 (SEQ ID NO:3) and Drosophila WART (SEQ ID NO:13) amino acid sequences.

DETAILED DESCRIPTION OF THE INVENTION

The present invention is based in part upon the isolation and characterization of nucleic acid molecules encoding novel hWART proteins. The invention also relates to nucleic acid molecules encoding portions of hWART polypeptides, nucleic acid molecules encoding at least one hWART functional portion, nucleic acid vectors harboring such nucleic acid molecules, recombinant cells containing such nucleic acid vectors, purified polypeptides encoded by such nucleic acid molecules, antibodies to such polypeptides, and methods of identifying compounds that modulate the function of hWART polypeptides. Also disclosed are methods for diagnosing abnormal cell proliferative conditions in an organism.

I. The Nucleic Acids of the Invention

A. hWART1 Nucleic Acid

The full-length human Wart1 cDNA is 7,382 bp long and consists of a 3,390 bp open reading frame (ORF) flanked by 394 and 3,554 bp of 5' and 3' untranslated regions (UTR) respectively. A 41 nucleotide polyA-rich tail follows the 3' UTR. There are two potential start codons at positions 395 and 431, neither corresponding to the Kozak consensus for initiating methionines. Although the second start site aligns to the N-terminal sequence of the related WART2, we have designated position 395 as the start site since it is the first start site encountered in this extended ORF. There are two additional ATGs located 5' to the start codon at position 395, but they are followed by stop codons after 31 and 10 nucleotides, respectively. The 3,390 nucleotide ORF has the potential to encode a 1,130 amino acid protein.

The 5' untranslated region from nucleotide 12–63 displays 10 copies of the tri-nucleotide repeat, GGC. This repeat is very similar to one found in the human retinoid X receptor beta (BG:M84820). Such repeats have been reported to undergo expansion in various human diseases particularly those associated with neuronal phenotypes. The 3' untranslated region contains an inverted 289 bp Alu-J subfamily repeat (between nucleotides 6,058–6,346). A polyadenylation signal (AATAAA) is found at position 7,338 followed by a 20 nucleotide long polyadenylated stretch.

Sequence analysis of multiple cDNA clones identified three polymorphisms in the human Wart1 gene: (1) at nucleotide 978 resulting in an Ala/Gly change; (2) at nucleotide 1,840, silent; (3) at nucleotides 3,252–3,253 comprising a deletion of two adenosines that results in a C-terminal truncation of the Wart1_h gene, disrupting the putative kinase domain. The frame shift mutation at position 3252 was observed in two independent clones isolated from the human bone marrow cDNA source. The non-mutated sequence however, was also confirmed in multiple independent clones. Conceivably, truncation of the WART1 STK could play a role in disease progression.

At least 8 EST fragments match the WART1_h gene over its 3' untranslated region and only one (GB:Z16134) was found to span part of the coding region of this gene (nucleotides 2,138–3,977).

B. hWART2 Nucleic Acid

The full-length human Wart2 cDNA is 5,276 bp long and consists of a 3,264 bp open reading frame (ORF) flanked by 394 and 1,612 bp of 5' and 3' untranslated regions (UTR) respectively. A 23 nucleotide polyA-rich tail follows the 3' UTR. This ORF has the potential to encode a 1,088 amino acid polypeptide. Based on amino acid sequence homology to the Drosophila and human Wart1 proteins we beleive that this ORF encodes the human Wart2 protein. There are 5 additional ORF's, none longer than 144 nucleotides, 5' to nucleotide 375. The ATG at position 375 fits the Kozak consensus for translational initiation.

Fourteen EST and one STS fragment match the Wart2_h cDNA sequence. These ESTs cluster into 5 contigs and match the Wart2_h coding region at the following positions: N56660 at 712, R75698 at 3,077, H26525 at 3,109, R01798 at 2,751, AA30618 at 163. The latter is a TIGR EST whose 3' end matches position 5,276 at the 3' end of the Wart2 gene.

II. The Proteins of the Invention

The open reading frame (ORF) of the full-length hWART1 nucleic acid molecule is predicted to encode a protein of 1130 amino acids with a predicted molecular weight of approximately 127 kDa. The ORF of the full-length hWART2 nucleic acid molecule is predicted to encode a protein of 1088 amino acids with a molecular weight of approximately 120 kDa. Structural analysis of these protein sequences predicts that hWART1 and hWART2 are likely to be intracellular proteins.

A. hWART1 Protein

Analysis of the deduced amino acid sequence predicts hWART1 to be an intracellular protein, lacking both a signal sequence and transmembrane domain. The predicted amino acid sequence contains a long N-terminal region that is believed to be predominately alpha helical and hydrophilic followed by a C-terminal domain with all the motifs characteristic of a serine-threonine kinase. Several regions of homology exist between the hWART1, hWART2 and Drosophila homologue. A Smith-Waterman pairwise alignment of hWART1 and hWART2 is shown in FIG. 1, and a similar alignment between hWART1 and Drosophila WART (SEQ ID NO:13) is shown in FIG. 2. The description and boundaries of these motifs are described in the following paragraphs.

The extreme N-terminal region of the hWART1 protein extending from 12–45 amino acids, shares 66% identity and 78% similarity to the corresponding region in hWART2. This domain is referred to as "BOX A". Box B lies ten amino acids C-terminal to Box A and extends from amino acids 55–151. Box B shares 56% identity and 77% similarity to the corresponding region in hWART2. Drosophila WART protein lacks significant homology to the N-terminal Box A and B present in the two human proteins. A Smith-Waterman search of the nonredundant protein database with the amino acid sequences of Box A and Box B does not reveal any significant homologies that might suggest a potential function for these two conserved regions.

hWART1 contains a proline-rich region, consisting of 26% prolines, extending from amino acids 236–377. This region is distantly similar to Volvox extensin proteins (40% amino acid identity with Volvox cateri extensin GB:x65165 using Smith-Waterman alignment) and may represent a protein interaction domain as well as a possible site for interaction with proteins containing SH3 motifs. WART homologues from Drosophila melanogaster (PIR:A56155) and Caenorhabditis elegans (EMBL:Z8159) have an N-terminal proline-rich comparable to the one found in hWART1, but this region is lacking in hWART2. Box C extends from amino acids 404–520 and is 44% identical and 73% similar to hWART2. A small portion of Box C is also found in a similar position in D. melanogaster WART but is mostly replaced with a glutamine-rich region. A Smith-Waterman search of the nonredundant protein database with the amino acid sequence of Box C did not reveal significant homologies that would suggest a potential function for this region. The 5' amino acid motif $P_4Y$ is present between amino acids 555–559 of hWART1 and is conserved in hWART2 and Drosophila WART. This region may represent an SH3 or WW domain binding site or may be a site for tyrosine phosphorylation and SH2 interactions.

A distinguishing feature of the WART family is the extended homology flanking both the N- and C-terminal side of their predicted serine-threonine kinase domain. This extended homology is present in the human and mouse WART1 and WART2, D. melanogaster WART, and C. elegans WART. The N-terminal flanking region of the hWART1 catalytic domain extends from amino acids 601–702 of hWART1 and is 69%, 71%, and 45% identical and 85%, 85%, and 64% similar with hWART2, D. melanogaster WART, and C. elegans WART, respectively. The catalytic domain of WART1 (amino acids 691–998) is 85%, 75%, and 53% identical 90%, 87%, and 72% similar with hWART2, D. melanogaster WART, C. elegans WART, respectively. The region C-terminal to the catalytic domain, extending from amino acids 1011–1086 in hWART1 is 63%, 53%, and 40% identical and 76%, 73%, and 56% similar with hWART2, D. melanogaster WART, and C. elegans WART, respectively.

The extended homology on either side of the catalytic domain of the WART kinases suggests these regions may actually be a part of this enzymatic domain. Other Serine-threonine kinases including Calmodulin-dependent kinases and DUN1 kinases from S. cerevesiae, are also characterized by an extended kinase domain.

B. hWART2 Protein

The 5276 bp human WART2 sequence is predicted to encode a polypeptide of 1,088 amino acids (SEQ ID NO:4). Analysis of the deduced amino acid sequence predicts hWART2 to be an intracellular protein, lacking both a signal sequence and transmembrane domain. Like hWART1, it contains a long N-terminal region that is predominately alpha helical and hydrophilic followed by a C-terminal domain with all the motifs characteristic of a serine-threonine kinase. Several regions of homology exist between hWART1, hWART2 and the Drosophila homologue (FIGS. 1 and 2). Box A extends from amino acids 1–33 and is 66% identical and 78% similar to the corresponding region in hWART1. Box B lies 21 amino acids C-terminal to Box A from amino acids 43–139. The hWART2 Box B is 56% identical and 77% similar to the corresponding region in hWART1. Box C extends from amino acids 342–466 and is 44% identical and 73% similar to hWART1. A GC nucleotide repeat region encodes alternating prolines and alanines (PAPA Box) from amino acids 467–480. This motif is also present in the human Cdk-inhibitor p57KIP2 (GB:U22398), and in the myosin light chain protein from several species. A recent study examined the human p57KIP2 for genetic variations in a large number of tumors (Tokino et al., "Characterization of the human p57 (KIP2) gene: alternative splicing, insertion/deletion polymorphisms in VNTR sequences in the coding region, and mutational analysis." Hum. Genet. 97:625–631, 1996). This study identified 4 types of 12-bp deletions in the proline/alanine rich region of p57KIP2, none of which were somatic mutations, suggesting that the GC repeat region of hWART2 may also be subject to variations in size, possibly resulting in altered gene function. The $P_4Y$ motif lies at amino acids 514–518 in hWART2 and is also found in a similar location in hWART1 and D. melanogaster WART.

The region immediately N-terminal to the core of the WART2 kinase domain extends from amino acid 564–665 and is 69%, 65%, and 41% identical and 85%, 82%, and 62% similar with human WART1, D. melanogaster WART, and C. elegans WART, respectively. The catalytic domain of WART2 (amino acids 666–973) is 85%, 75%, and 53% identical and 90%, 86%, and 70% similar with hWART1, D. melanogaster WART, and C. elegans WART, respectively. The region C-terminal to the catalytic domain extends from amino acids 974–1048 in WART2 is 63%, 50%, and 36% identical and 76%, 72%, and 60% similar with hWART1, D. melanogaster WART, and C. elegans WART1, respectively.

III. Applications, Biological Significance, and Clinical Utility of hWARTs

Experimental studies of the WART homologues from lower organisms suggest hWART1 may play a role in the regulation of normal epithelial cell growth. Therefore, compounds that specifically modulate the function of these proteins would likely alter the growth or biology of epithelial tumors and would provide novel potential treatments for human cancer.

IV. A Nucleic Acid Probe for the Detection of hWARTs

A nucleic acid probe of the present invention may be used to probe an appropriate chromosomal or cDNA library by usual hybridization methods to obtain another nucleic acid molecule of the present invention. A chromosomal DNA or cDNA library may be prepared from appropriate cells according to recognized methods in the art (e.g. "Molecular Cloning: A Laboratory Manual", second edition, edited by Sambrook, Fritsch, & Maniatis, Cold Spring Harbor Laboratory, 1989).

In the alternative, chemical synthesis is carried out in order to obtain nucleic acid probes having nucleotide sequences which correspond to N-terminal and C-terminal portions of the amino acid sequence of the polypeptide of interest. Thus, the synthesized nucleic acid probes may be used as primers in a polymerase chain reaction (PCR) carried out in accordance with recognized PCR techniques, essentially according to PCR Protocols, "PCR Protocols, A Guide to Methods and Applications", edited by Innis et al., Academic Press, 1990, utilizing the appropriate chromosomal or cDNA library to obtain the fragment of the present invention.

One skilled in the art can readily design such probes based on the sequence disclosed herein using methods of computer alignment and sequence analysis known in the art (e.g. "Molecular Cloning: A Laboratory Manual", second edition, edited by Sambrook, Fritsch, & Maniatis, Cold Spring Harbor Laboratory, 1989). The hybridization probes of the present invention can be labeled by standard labeling techniques such as with a radiolabel, enzyme label, fluorescent label, biotin-avidin label, chemiluminescence, and the like. After hybridization, the probes may be visualized using known methods.

The nucleic acid probes of the present invention include RNA as well as DNA probes and nucleic acids modified in the sugar, phosphate or even the base portion as long as the probe still retains the ability to specifically hybridize under conditions as disclosed herein. Such probes are generated using techniques known in the art. The nucleic acid probe may be immobilized on a solid support. Examples of such solid supports include, but are not limited to, plastics such as polycarbonate, complex carbohydrates such as agarose and sepharose, acrylic resins, such as polyacrylamide and latex beads, and nitrocellulose. Techniques for coupling nucleic acid probes to such solid supports are well known in the art.

The test samples suitable for nucleic acid probing methods of the present invention include, for example, cells or nucleic acid extracts of cells, or biological fluids. The sample used in the above-described methods will vary based on the assay format, the detection method and the nature of the tissues, cells or extracts to be assayed. Methods for preparing nucleic acid extracts of cells are well known in the art and can be readily adapted in order to obtain a sample which is compatible with the method utilized.

V. A Probe Based Method and Kit for Detecting hWART

One method of detecting the presence of hWART in a sample comprises (a) contacting the sample with one of the above-described nucleic acid probes, under conditions such that hybridization occurs, and (b) detecting the presence of the probe bound to a nucleic acid molecule in the sample. One skilled in the art would select the nucleic acid probe according to techniques known in the art as described above. Samples to be tested include but should not be limited to RNA samples of human tissue.

A kit for detecting the presence of hWART in a sample comprises at least one container having disposed therein an above-described nucleic acid probe. The kit may further comprise other containers comprising one or more of the following: wash reagents and reagents capable of detecting the presence of bound nucleic acid probe. Examples of detection reagents include, but are not limited to radiolabelled probes, enzymatically labeled probes (horseradish peroxidase, alkaline phosphatase), and affinity labeled probes (biotin, avidin, or steptavidin).

In detail, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, Tris-buffers, and the like), and containers which contain the reagents used to detect the hybridized probe, bound antibody, amplified product, or the like. One skilled in the art will readily recognize that the nucleic acid probes described in the present invention can readily be incorporated into one of the established kit formats which are well known in the art.

VI. DNA Constructs Comprising an hWART Nucleic Acid Molecule and Cells Containing These Constructs The present invention also relates to a recombinant DNA molecule comprising, 5' to 3', a promoter effective to initiate transcription in a host cell and one of the above-described nucleic acid molecules. In addition, the present invention relates to a recombinant DNA molecule comprising a vector and a nucleic acid molecule described herein. The present invention also relates to a nucleic acid molecule comprising a transcriptional region functional in a cell, a sequence complimentary to an RNA sequence encoding an amino acid sequence corresponding to an hWART polypeptide, or functional derivative, and a transcriptional termination region functional in said cell. The above-described molecules may be isolated and/or purified DNA molecules.

The present invention also relates to a cell or organism that contains an hWART nucleic acid molecule, as described herein, and thereby is capable of expressing a peptide. The polypeptide may be purified from cells which have been altered to express the polypeptide. A cell is said to be "altered to express a desired polypeptide" when the cell, through genetic manipulation, is made to produce a protein which it normally does not produce or which the cell normally produces at lower levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression may vary from organism to organism, but will in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

If desired, the non-coding region 3' to the sequence encoding an hWART gene may be obtained by the above-described cloning methods. This region may be retained for its transcriptional termination regulatory sequences, such as termination and polyadenylation. Thus, by retaining the 3'-region naturally contiguous to the DNA sequence encoding an hWART gene, the transcriptional termination signals may be provided. Where the transcriptional termination signals are not satisfactorily functional in the expression host cell, then a 3' region functional in the host cell may be substituted.

Two DNA sequences (such as a promoter region sequence and an hWART sequence) are said to be operably linked if the nature of the linkage between the two DNA sequences does not (1) result in the introduction of a frame-shift mutation, (2) interfere with the ability of the promoter region sequence to direct the transcription of the second sequence, for example an hWART gene sequence, or (3) interfere with the ability of the second sequence to be transcribed by the promoter region sequence. Thus, a promoter region would be operably linked to a DNA sequence if the promoter were capable of effecting transcription of that DNA sequence. Thus, transcriptional and translational signals recognized by an appropriate host are necessary to express an hWART gene.

The present invention encompasses the expression of an hWART gene (or a functional derivative thereof) in either prokaryotic or eukaryotic cells. Prokaryotic hosts are, generally, very efficient and convenient for the production of recombinant proteins and are, therefore, one type of preferred expression system for these genes. Prokaryotes most frequently are represented by various strains of *E. coli*. However, other microbial strains may also be used, including other bacterial strains.

In prokaryotic systems, plasmid vectors that contain replication sites and control sequences derived from a species compatible with the host may be used. Examples of suitable plasmid vectors may include pBR322, pUC118, pUC119 and the like; suitable phage or bacteriophage vectors may include gt10, gt11 and the like; and suitable virus vectors may include pMAM-neo, pKRC and the like. Preferably, the selected vector of the present invention has the capacity to replicate in the selected host cell.

Recognized prokaryotic hosts include bacteria such as *E. coli* and those from genera such as Bacillus, Streptomyces, Pseudomonas, Salmonella, Serratia, and the like. However, under such conditions, the polypeptide will not be glycosylated. The prokaryotic host must be compatible with the replicon and control sequences in the expression plasmid.

To express hWART (or a functional derivative thereof) in a prokaryotic cell, it is necessary to operably link the gene sequence to a functional prokaryotic promoter. Such promoters may be either constitutive or, more preferably, regulatable (i.e., inducible or derepressible). Examples of constitutive promoters include the int promoter of bacteriophage 1, the bla promoter of the lactamase gene sequence of pBR322, and the CAT promoter of the chloramphenicol acetyl transferase gene sequence of pPR325, and the like. Examples of inducible prokaryotic promoters include the major right and left promoters of bacteriophage 1 ($P_L$ and $P_R$) , the trp, recA, lacZ, lacI, and gal promoters of *E. coli*, the a-amylase (Ulmanen, et at., J. Bacteriol. 162:176–182, 1985) and the sigma-28-specific promoters of *B. subtilis* (Gilman, et al., Gene sequence 32:11–20, 1984), the promoters of the bacteriophages of Bacillus (Gryczan, In: The Molecular Biology of the Bacilli, Academic Press, Inc., NY, 1982), and Streptomyces promoters (Ward, et at., Mol. Gen. Genet. 203:468–478, 1986). Prokaryotic promoters are reviewed by Glick, J. Ind. Microbiot. 1:277–282, 1987; Cenatiempo, Biochimie 68:505–516, 1986; and Gottesman, Ann. Rev. Genet. 18:415–442, 1984.

Proper expression in a prokaryotic cell also requires the presence of a ribosome binding site upstream of the gene sequence-encoding sequence. Such ribosome binding sites are disclosed (see, for example, Gold, et at., Ann. Rev. Microbiol. 35:365–404, 1981). The selection of control sequences, expression vectors, transformation methods, and the like, are dependent on the type of host cell used to express the gene.

As used herein, "cell", "cell line", and "cell culture" may be used interchangeably and all such designations include the progeny of the cells. Thus, the words "transformants" or "transformed cells" include the primary subject cell and cultures derived therefrom, without regard to the number of transfers. It is also understood that all progeny may not be precisely identical in DNA content, due to deliberate or inadvertent mutations. However, as defined, mutant progeny have the same functionality as that of the originally transformed cell.

Host cells which may be used in the expression systems of the present invention are not strictly limited, provided that they are suitable for use in the expression of the hWART peptide of interest. Suitable hosts may often include eukaryotic cells. Preferred eukaryotic hosts include, for example, yeast, fungi, insect cells, and mammalian cells, either in vivo or in tissue culture. Mammalian cells which may be useful as hosts include HeLa cells, cells of fibroblast origin such as VERO, 3T3 or CHO-K1, or cells of lymphoid origin (such as 32D cells) and their derivatives. Preferred mammalian host cells include SP2/0 and J558L, as well as neuroblastoma cell lines such as IMR 332 and PC12 which may provide better capacities for correct post-translational processing.

In addition, plant cells are also available as hosts, and control sequences compatible with plant cells are available, such as the cauliflower mosaic virus 35S and 19S, and nopaline synthase promoter and polyadenylation signal sequences. Another preferred host is an insect cell, for example the Drosophila larvae. Using insect cells as hosts, the Drosophila alcohol dehydrogenase promoter can be used (Rubin, Science 240:1453–1459, 1988). Alternatively, baculovirus vectors can be engineered to express large amounts of hWART in insects cells (Jasny, Science 238:1653, 1987; Miller, et al., In: Genetic Engineering, 1986; Setlow, J. K., et al., eds., Plenum, Vol. 8, pp. 277–297).

Any of a series of yeast gene sequence expression systems can be utilized which incorporate promoter and termination elements from the actively expressed gene sequences coding for glycolytic enzymes; the systems are produced in large quantities when yeast are grown in mediums rich in glucose. Known glycolytic gene sequences can also provide very efficient transcriptional control signals. Yeast provides substantial advantages in that it can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., pre-peptides). For a mammalian host, several possible vector systems are available for the expression of hWART.

A particularly preferred yeast expression system is that utilizing Schizosaccharmocyces pombe. This system is useful for studying the activity of members of the Src family (Superti-Furga, et al., EMBO J. 12:2625, 1993) and other non-receptor-TKs, the function of which is often regulated by the activity of tyrosine phosphatases.

A wide variety of transcriptional and translational regulatory sequences may be employed, depending upon the nature of the host. The transcriptional and translational regulatory signals may be derived from viral sources, such as adenovirus, bovine papilloma virus, cytomegalovirus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

Expression of hWART in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer, et al., J. Mol. Appl. Gen. 1:273–288, 1982); the TK promoter of Herpes virus (McKnight, Cell 31:355–365, 1982); the SV40 early promoter (Benoist, et al., Nature (London) 290:304–310, 1981); and the yeast gal4 gene sequence promoter (Johnston, et al., Proc. Natl. Acad. Sci. (USA) 79:6971–6975, 1982; Silver, et al., Proc. Natl. Acad. Sci. (USA) 81:5951–5955, 1984).

Translation of eukaryotic mRNA is initiated at the codon which encodes the first methionine. For this reason, it is preferable to ensure that the linkage between a eukaryotic promoter and a DNA sequence which encodes hWART (or a functional derivative thereof) does not contain any intervening codons which are capable of encoding a methionine (i.e., AUG). The presence of such codons results either in the formation of a fusion protein (if the AUG codon is in the same reading frame as the coding sequence) or a frame-shift mutation (if the AUG codon is not in the same reading frame as an hWART coding sequence).

An hWART nucleic acid molecule and an operably linked promoter may be introduced into a recipient prokaryotic or eukaryotic cell either as a nonreplicating DNA (or RNA) molecule, which may either be a linear molecule or, more preferably, a closed covalent circular molecule (a plasmid). Since such molecules are incapable of autonomous replication, the expression of the gene may occur through the transient expression of the introduced sequence. Alternatively, permanent or stable expression may occur through the integration of the introduced DNA sequence into the host chromosome.

A vector may be employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, Mol. Cell. Bio. 3:280, 1983.

The introduced nucleic acid molecule can be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as those capable of replication in *E. coil* (such as, for example, pBR322, ColEl, pSC101, pACYC 184, pVX). Such plasmids are, for example, disclosed by Sambrook (c.f. "Molecular Cloning: A Laboratory Manual", second edition, edited by Sambrook, Fritsch, & Maniatis, Cold Spring Harbor Laboratory, 1989). Bacillus plasmids include pC194, pC221, pT127, and the like. Such plasmids are disclosed by Gryczan (In: The Molecular Biology of the Bacilli, Academic Press, NY, 1982, pp. 307–329). Suitable Streptomyces plasmids include p1J101 (Kendall, et al., J. Bacteriol. 169:4177–4183, 1987), and streptomyces bacteriophages such as fC31 (Chater, et al., In: Sixth International Symposium on Actinomycetales Biology, Akademiai Kaido, Budapest, Hungary, 1986, pp. 45–54). Pseudomonas plasmids are reviewed by John, et al., Rev. Infect. Dis. 8:693–704, 1986, and Izaki, Jpn. J. Bacteriol. 33:729–742, 1978.

Preferred eukaryotic plasmids include, for example, BPV, vaccinia, SV40, 2-micron circle, and the like, or their derivatives. Such plasmids are well known in the art (Botstein, et al., Miami Wntr. Symp. 19:265–274, 1982); Broach, In: "The Molecular Biology of the Yeast Saccharomyces: Life Cycle and Inheritance", Cold Spring Harbor Laboratory, Cold Spring Harbor, NY, p. 445–470 1981; Broach, Cell 28:203–204, 1982; Bollon et at., J. Clin. Hematol. Oncol. 10:39–48, 1980; Maniatis, In: Cell Biology: A Comprehensive Treatise, Vol. 3, Gene Sequence Expression, Academic Press, NY, pp. 563–608, 1980.

Once the vector or nucleic acid molecule containing the construct(s) has been prepared for expression, the DNA construct(s) may be introduced into an appropriate host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene molecule(s) results in the production of hWART or fragments or functional derivatives thereof. This can take place in the transformed cells as such, or following the induction of these cells to differentiate (for example, by administration of bromodeoxyuracil to neuroblastoma cells or the like). A variety of incubation conditions for the transformed cells can be used to foster expression of the polypeptides of the present invention. The most preferred conditions are those which mimic physiological conditions.

VII. An Antibody having Binding Affinity to an hWART Polypeptide and Hybridomas Producing the Antibody The present invention also relates to an antibody having specific binding affinity to an hWART polypeptide. The polypeptide may have the amino acid sequence set forth in SEQ ID NO:3 or SEQ ID NO:4, or a fragment thereof, or at least 41 contiguous amino acids thereof. Such an antibody may be identified by comparing its binding affinity to the desired polypeptide, for example an hWART polypeptide, with its binding affinity to another (non-hWART) polypeptide. Those which bind selectively to the desired polypeptide would be chosen for use in methods requiring a distinction between the desired polypeptide and other polypeptides. Such methods could include, but should not be limited to, the analysis of altered expression of the desired polypeptide in tissue containing other polypeptides and assay systems using whole cells.

An hWART polypeptide of the present invention can be used to produce antibodies or hybridomas. One skilled in the art will recognize that if an antibody is desired, such a peptide would be generated as described herein and used as an immunogen. The antibodies of the present invention include monoclonal and polyclonal antibodies, as well fragments of these antibodies, and humanized forms. Humanized forms of the antibodies of the present invention may be generated using one of the procedures known in the art such as chimerization or CDR grafting. The present invention also relates to a hybridoma which produces the above-described monoclonal antibody, or binding fragment thereof. A hybridoma is an immortalized cell line which is capable of secreting a specific monoclonal antibody.

In general, techniques for preparing monoclonal antibodies and hybridomas are well known in the art (Campbell, "Monoclonal Antibody Technology: Laboratory Techniques in Biochemistry and Molecular Biology," Elsevier Science Publishers, Amsterdam, The Netherlands, 1984; St. Groth et al., J. Immunol. Methods 35:1–21, 1980). Any animal (mouse, rabbit, and the like) which is known to produce antibodies can be immunized with the selected polypeptide. Methods for immunization are well known in the art. Such methods include subcutaneous or intraperitoneal injection of the polypeptide. One skilled in the art will recognize that the amount of polypeptide used for immunization will vary based on the animal which is immunized, the antigenicity of the polypeptide and the site of injection.

The polypeptide may be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Agl4 myeloma cells, and allowed to become monoclonal antibody producing hybridoma cells. Any one of a number of methods well known in the art can be used to identify the hybridoma cell which produces an antibody with the desired characteristics. These include screening the hybridomas with an ELISA assay, western blot analysis, or radioimmunoassay (Lutz, et al., Exp. Cell Res. 175:109–124, 1988). Hybridomas secreting the desired antibodies are cloned and the class and subclass is determined using procedures known in the art (Campbell, "Monoclonal Antibody Technology: Laboratory Techniques in Biochemistry and Molecular Biology", supra, 1984).

For polyclonal antibodies, antibody containing antisera is isolated from the immunized animal and is screened for the presence of antibodies with the desired specificity using one of the above-described procedures. The above-described antibodies may be detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagnetic atoms, and the like. Procedures for accomplishing such labeling are well-known in the art, for example, see (Stemberger, et al., J. Histochem. Cytochem. 18:315, 1970; Bayer, et al., Meth. Enzym. 62:308, 1979; Engval, et al., Immunot. 109:129, 1972; Goding, J. Immunol. Meth. 13:215, 1976). The labeled antibodies of the present invention can be used for in vitro, in vivo, and in situ assays to identify cells or tissues which express a specific peptide.

The above-described antibodies may also be immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "Handbook of Experimental Immunology" 4th Ed., Blackwell Scientific Publications, Oxford, England, Chapter 10, 1986; Jacoby, et al., Meth. Enzym. 34, Academic Press, N.Y., 1974). The immobilized antibodies of the present invention can be used for in vitro, in vivo, and in situ assays as well as in immunochromotography.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides, for example see Hurby et al., "Application of Synthetic Peptides: Antisense Peptides", In Synthetic Peptides, A User's Guide, W.H. Freeman, NY, pp. 289–307, 1992, and Kaspczak, et al., Biochemistry 28:9230–8, 1989.

VIII. An Antibody Based Method and Kit for Detecting hWART

The present invention encompasses a method of detecting an hWART polypeptide in a sample comprising incubating a test sample with one or more of the antibodies of the present invention and determining whether the antibody binds to the test sample. The method can include the steps of, for example: (a) contacting the sample with an above-described antibody, under conditions such that immunocomplexes form, and (b) detecting the presence of said antibody bound to the polypeptide. Altered levels, either an increase or decrease, of hWART in a sample as compared to normal levels may indicate an abnormality or disorder.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, "An Introduction to Radioimmunoassay and Related Techniques" Elsevier Science Publishers, Amsterdam, The Netherlands 1986; Bullock et al., "Techniques in Immunocytochemistry," Academic Press, Orlando, Fla. Vol. 1 (1982), Vol. 2 (1983), Vol. 3 (1985); Tijssen, "Practice and Theory of Enzyme Immunoassays: Laboratory Techniques in Biochemistry and Molecular Biology," Elsevier Science Publishers, Amsterdam, The Netherlands (1985).

The immunological assay test samples of the present invention include cells, protein or membrane extracts of cells, or biological fluids such as blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily adapted in order to obtain a sample which is compatible with the system utilized.

A kit contains all the necessary reagents to carry out the previously described methods of detection. The kit may comprise: (i) a first container containing an above-described antibody, and (ii) a second container containing a conjugate comprising a binding partner of the antibody and a label. In another preferred embodiment, the kit further comprises one or more other containers comprising one or more of the following: wash reagents and reagents capable of detecting the presence of bound antibodies.

Examples of detection reagents include, but are not limited to, labeled secondary antibodies, or in the alternative, if the primary antibody is labeled, the chromophoric, enzymatic, or antibody binding reagents which are capable of reacting with the labeled antibody. The compartmentalized kit may be as described above for nucleic acid probe kits. One skilled in the art will recognize that the antibodies described in the present invention can readily be incorporated into one of the established kit formats which are well known in the art.

IX. Isolation of Natural Binding Partners of hWART

The present invention also relates to methods of detecting natural binding partners capable of binding to an hWART polypeptide. A natural binding partner of hWART may be, for example, a substrate protein which is dephosphorylated as part of a signaling cascade. The binding partner(s) may be present within a complex mixture, for example, serum, body fluids, or cell extracts.

In general, methods for identifying natural binding partners comprise incubating a substance with a first polypeptide, hWART for the invention described herein, and detecting the presence of a substance bound to the first polypeptide. Preferred methods include the two-hybrid system of Fields and Song (supra) and co-immunoprecipitation wherein the first polypeptide is allowed to bind to a natural binding partner, then the polypeptide complex is immunoprecipitated using antibodies specific for the first polypeptide. The natural binding partner can then be isolated and identified by techniques well known in the art.

X. Identification of and Uses for Substances Capable of Modulating hWART Activity The present invention also relates to a method of detecting a substance capable of modulating hWART activity. Such substances can either enhance activity (agonists) or inhibit activity (antagonists). Agonists and antagonists can be peptides, antibodies, products from natural sources such as fungal or plant extracts or small molecular weight organic compounds. In general, small molecular weight organic compounds are preferred. Examples of classes of compounds that can be tested for hWART modulating activity are, for example but not limited to, thiazoles (see, for example U.S. applications No. 60/033,522 filed Dec. 19, 1996, and Ser. No. 08/660,900 filed Jun. 7, 1996), and naphthopyrones (U.S. Pat. No. 5,602,171, issued Feb. 11, 1997).

In general the method comprises incubating cells that produce hWART in the presence of a test substance and detecting changes in the level of hWART activity or hWART binding partner activity. A change in activity may be manifested by increased or decreased binding of an hWART polypeptide to a natural binding partner or increased or decreased biological response in cells. Biological responses can include, for example, proliferation, differentiation, survival, or motility. The substance thus identified would produce a change in activity indicative of the agonist or antagonist nature of the substance. Once the substance is identified it can be isolated using techniques well known in the art, if not already available in a purified form.

The present invention also encompasses a method of agonizing (stimulating) or antagonizing hWART associated activity in a mammal comprising administering to said mammal an agonist or antagonist to hWART in an amount sufficient to effect said agonism or antagonism. Also encompassed in the present application is a method of treating diseases in a mammal with an agonist or antagonist of hWART-related activity comprising administering the agonist or antagonist to a mammal in an amount sufficient to agonize or antagonize hWART associated function(s). The particular compound can be administered to a patient either by itself or in a pharmaceutical composition where it is mixed with suitable carriers or excipient(s). In treating a patient, a therapeutically effective dose of the compound is administered. A therapeutically effective dose refers to that amount of the compound that results in amelioration of symptoms or a prolongation of survival in a patient.

Toxicity and therapeutic efficacy of such compounds can be determined by standard pharmaceutical procedures in cell cultures or experimental animals. Cell culture assays and animal studies can be used for determining the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. Compounds which exhibit large therapeutic indices are preferred. The data obtained from these cell culture assays and animal studies can be used in formulating a range of dosages for use in human. The dosage of such compounds lies preferably within a range of circulating concentrations that include the $ED_{50}$ with little or no toxicity. The dosage may vary within this range depending upon the dosage form employed and the route of administration utilized.

For any compound used in the method of the invention, the therapeutically effective dose can be estimated initially from cell culture assays by determining an $IC_{50}$ (i.e., the concentration of the test compound which achieves a half-maximal disruption of the protein complex, or a half-maximal inhibition of the cellular level and/or activity of a cellular component, ex. hWART). A dose can then be formulated in animal models to achieve a circulating plasma concentration range that includes the $IC_{50}$ as determined in cell culture. Such information can be used to more accurately determine useful doses in humans. Levels in plasma may be measured, for example, by HPLC. The exact formulation, route of administration and dosage can be chosen by the individual physician in view of the patient's condition. (See e.g. Fingl et al., in "The Pharmacological Basis of Therapeutics", Ch. 1 p1, 1975).

It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the oncogenic disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in "Remington's Pharmaceutical Sciences," 1990, 18th ed., Mack Publishing Co., Easton, Pa. Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated. Particular formulations suitable for parenteral administration of hydrophobic compounds can be found in U.S. Pat. No. 5,610,173, issued Mar. 11, 1997 and U.S. Provisional Application Ser. No. 60/039,870, filed Mar. 5, 1997, both of which are hereby incorporated by reference herein in their entirety, including any figures and drawings.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Small organic molecules may be directly administered intracellularly due to their hydrophobicity.

Pharmaceutical compositions suitable for use in the present invention include compositions wherein the active ingredients are contained in an amount effective to achieve its intended purpose. Determination of an effective amount is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

The present invention also includes a kit containing the the active ingredients mentioned above. The kit may or may not include other compounds, such as carriers or excipients, and the active ingredient may be included in a suitable pharmaceutical composition. The kit may include a protocol for the use of the compounds of the invention. Said protocol may be approved by the Food and Drug Administration or an equivalent agency.

XI. Transgenic Animals

Also contemplated by the invention are transgenic animals useful for the study of hWART activity in complex in vivo systems. A "transgenic animal" is an animal having cells that contain DNA which has been artificially inserted into a cell, which DNA becomes part of the genome of the animal which develops from that cell. Preferred transgenic animals are primates, mice, rats, cows, pigs, horses, goats, sheep, dogs and cats. The transgenic DNA may encode a human hWART polypeptide. Native expression in an animal may alternatively be reduced by providing an amount of antisense RNA or DNA effective to reduce expression of the target gene.

A variety of methods are available for the production of transgenic animals associated with this invention. DNA sequences encoding hWART can be injected into the pronucleus of a fertilized egg before fusion of the male and female pronuclei, or injected into the nucleus of an embryonic cell (e.g., the nucleus of a two-cell embryo) following the initiation of cell division (Brinster, et al., Proc. Nat. Acad. Sci. USA 82: 4438, 1985). Embryos can be infected with viruses, especially retroviruses, modified to carry inorganic-ion receptor nucleotide sequences of the invention.

Pluripotent stem cells derived from the inner cell mass of the embryo and stabilized in culture can be manipulated in culture to incorporate nucleotide sequences of the invention. A transgenic animal can be produced from such cells through implantation into a blastocyst that is implanted into a foster mother and allowed to come to term. Animals suitable for transgenic experiments can be obtained from standard commercial sources such as Charles River (Wilmington, Mass.), Taconic (Germantown, N.Y.), Harlan Sprague Dawley (Indianapolis, Ind.), etc.

The procedures for manipulation of the rodent embryo and for microinjection of DNA into the pronucleus of the zygote are well known to those of ordinary skill in the art (Hogan, et al., supra). Microinjection procedures for fish, amphibian eggs and birds are detailed in Houdebine and Chourrout, Experientia 47:897–905, 1991. Other procedures for introduction of DNA into tissues of animals are described in U.S. Pat. No. , 4,945,050 (Sandford et al., Jul. 30, 1990).

By way of example only, to prepare a transgenic mouse, female mice are induced to superovulate. After being allowed to mate, the females are sacrificed by $CO_2$ asphyxiation or cervical dislocation and embryos are recovered from excised oviducts. Surrounding cumulus cells are removed. Pronuclear embryos are then washed and stored until the time of injection. Randomly cycling adult female mice are paired with vasectomized males. Recipient females are mated at the same time as donor females. Embryos then are transferred surgically. The procedure for generating transgenic rats is similar to that of mice. See Hammer, et al., Cell 63:1099–1112, 1990.

Methods for the culturing of embryonic stem (ES) cells and the subsequent production of transgenic animals by the introduction of DNA into ES cells using methods such as electroporation, calcium phosphate/DNA precipitation and direct injection also are well known to those of ordinary skill in the art. (See, for example, Teratocarcinomas and Embryonic Stem Cells, A Practical Approach, E. J. Robertson, ed., IRL Press, 1987). In cases involving random gene integration, a clone containing the sequence(s) of the invention is co-transfected with a gene encoding resistance. Alternatively, a gene encoding neomycin resistance is physically linked to the sequence(s) of the invention. Transfection and isolation of desired clones are carried out by any one of several methods well known to those of ordinary skill in the art (E. J. Robertson, supra). DNA molecules introduced into ES cells can also be integrated into the chromosome through the process of homologous recombination. (See Capecchi, Science 244: 1288, 1989.) Methods for positive selection of the recombination event (i.e., neo resistance) and dual positive-negative selection (i.e., neo resistance and gancyclovir resistance) and the subsequent identification of the desired clones by PCR have been described by Capecchi, supra and Joyner et al., Nature 338: 153, 1989, the teachings of which are incorporated by reference herein. The final phase of the procedure is to inject targeted ES cells into blastocysts and to transfer the blastocysts into pseudopregnant females. The resulting chimeric animals are bred and the offspring are analyzed by Southern blotting to identify individuals that carry the transgene. Procedures for the production of non-rodent mammals and other animals have been discussed by others. (See Houdebine and Chourrout, supra; Pursel, et al., Science 244:1281, 1989; Simms, et al., Bio/Technology 6:179, 1988.)

Thus, the invention provides transgenic, nonhuman mammals containing a transgene encoding an hWART polypeptide or a gene effecting the expression of an hWART polypeptide. Such transgenic nonhuman mammals are particularly useful as an in vivo test system for studying the effects of introducing an hWART polypeptide, or for regulating the expression of an hWART polypeptide (i.e., through the introduction of additional genes, antisense nucleic acids, or ribozymes).

XII. Gene Therapy hWART nucleic acid sequences, both mutated and non-mutated, will also be useful in gene therapy (reviewed in Miller, Nature 357:455–460, 1992). Miller states that advances have resulted in practical approaches to human gene therapy that have demonstrated positive initial results. The basic science of gene therapy is described in Mulligan, Science 260:926, 1993. As used herein "gene therapy" is a form of gene transfer and is included within the definition of gene transfer as used herein and specifically refers to gene transfer to express a therapeutic product from a cell in vivo or in vitro. Gene transfer can be performed ex vivo on cells which are then transplanted into a patient, or can be performed by direct administration of the nucleic acid or nucleic acid-protein complex into the patient.

In one preferred embodiment, an expression vector containing an hWART coding sequence or an hWART mutant coding sequence, as described above, is inserted into cells, the cells are grown in vitro and then infused in large numbers into patients. In another preferred embodiment, a DNA segment containing a promoter of choice (for example a strong promoter) is transferred into cells containing an endogenous hWART in such a manner that the promoter segment enhances expression of the endogenous hWART gene (for example, the promoter segment is transferred to the cell such that it becomes directly linked to the endogenous hWART gene).

The gene therapy may involve the use of an adenovirus containing hWART cDNA targeted to an appropriate cell type, systemic hWART increase by implantation of engineered cells, injection with hWART virus, or injection of naked hWART DNA into appropriate cells or tissues, for example adipose tissue.

Expression vectors derived from viruses such as retroviruses, vaccinia virus, adenovirus, adeno-associated virus, herpes viruses, other RNA viruses, or bovine papilloma virus, may be used for delivery of nucleotide sequences (eg., cDNA) encoding recombinant hWART protein into the targeted cell population (e.g., tumor cells or fat cells). Methods which are well known to those skilled in the art can be used to construct recombinant viral vectors containing coding sequences. See, for example, the techniques described in Maniatis et al., Molecular Cloning: A Laboratory Manual, Cold Spring Harbor Laboratory, N.Y. (1989), and in Ausubel et al., Current Protocols in Molecular Biology, Greene Publishing Associates and Wiley Interscience, N.Y. (1989). Alternatively, recombinant nucleic acid molecules encoding protein sequences can be used as naked DNA or in reconstituted system e.g., liposomes or other lipid systems for delivery to target cells (See e.g., Feigner et al., Nature 337:387–8, 1989). Several other methods for the direct transfer of plasmid DNA into cells exist for use in human gene therapy and involve targeting the DNA to receptors on cells by complexing the plasmid DNA to proteins. See, Miller, supra.

In its simplest form, gene transfer can be performed by simply injecting minute amounts of DNA into the nucleus of a cell, through a process of microinjection. (Capecchi M R, Cell 22:479–88, 1980). Once recombinant genes are introduced into a cell, they can be recognized by the cell's normal mechanisms for transcription and translation, and a gene product will be expressed. Other methods have also been attempted for introducing DNA into larger numbers of cells. These methods include: transfection, wherein DNA is precipitated with $CaPO_4$ and taken into cells by pinocytosis (Chen C. and Okayama H, Mol. Cell Biol. 7:2745–52, 1987); electroporation, wherein cells are exposed to large voltage pulses to introduce holes into the membrane (Chu G., et al., Nucleic Acids Res., 15:1311–26, 1987); lipofection/liposome fusion, wherein DNA is packaged into lipophilic vesicles which fuse with a target cell (Feigner P L., et al., Proc. Natl. Acad. Sci. USA. 84:7413–7, 1987); and particle bombardment using DNA bound to small projectiles (Yang N S., et al., Proc. Natl. Acad. Sci. 87:9568–72, 1990). Another method for introducing DNA into cells is to couple the DNA to chemically modified proteins.

It has also been shown that adenovirus proteins are capable of destabilizing endosomes and enhancing the uptake of DNA into cells. The admixture of adenovirus to solutions containing DNA complexes, or the binding of DNA to polylysine covalently attached to adenovirus using protein crosslinking agents substantially improves the uptake and expression of the recombinant gene. (Curiel, et al., Am. J. Respir. Cell. Mol. Biol., 6:247–52, 1992).

As used herein "gene transfer" means the process of introducing a foreign nucleic acid molecule into a cell. Gene transfer is commonly performed to enable the expression of a particular product encoded by the gene. The product may include a protein, polypeptide, antisense DNA or RNA, or enzymatically active RNA. Gene transfer can be performed in cultured cells or by direct administration into animals. Generally gene transfer involves the process of nucleic acid contact with a target cell by non-specific or receptor mediated interactions, uptake of nucleic acid into the cell through the membrane or by endocytosis, and release of nucleic acid into the cytoplasm from the plasma membrane or endosome. Expression may require, in addition, movement of the nucleic acid into the nucleus of the cell and binding to appropriate nuclear factors for transcription.

In another preferred embodiment, a vector having nucleic acid sequences encoding an hWART is provided in which the nucleic acid sequence is expressed only in specific tissue. Methods of achieving tissue-specific gene expression as set forth in International Publication No. WO 93/09236, filed Nov. 3, 1992 and published May 13, 1993.

In all of the preceding vectors set forth above, a further aspect of the invention is that the nucleic acid sequence contained in the vector may include additions, deletions or modifications to some or all of the sequence of the nucleic acid, as defined above.

In another preferred embodiment, an hWART nucleic acid is used in gene replacement. "Gene replacement" as used herein means supplying a nucleic acid sequence which is capable of being expressed in vivo in an animal and thereby providing or augmenting the function of an endogenous gene which is missing or defective in the animal. Methods of introducing the nucleic acid into the animal to be treated are as described above.

One skilled in the art appreciates that any modifications made to a complex can be manifested in a modification of any of the molecules in that complex. Thus, the invention includes any modifications to nucleic acid molecules, polypeptides, antibodies, or compounds in a complex. All of these aspects and features are explained in detail with respect to PYK-2 in PCT publication WO 96/18738, which is incorporated herein by reference in its entirety, including any drawings. Those skilled in the art will readily appreciate that such descriptions can be easily adapted to hWART polypeptides and nucleic acid molecules as well, and is therefore equally applicable to the present invention.

XIII. Compounds that Modulate the Function of hWART Proteins

In an effort to discover novel treatments for diseases, biomedical researchers and chemists have designed, synthesized, and tested molecules that inhibit the function of protein kinases. Some small organic molecules form a class of compounds that modulate the function of protein kinases. Examples of molecules that have been reported to inhibit the function of protein kinases include, but are not limited to, bis monocyclic, bicyclic or heterocyclic aryl compounds (PCT WO 92/20642, published Nov. 26, 1992 by Maguire et al.), vinylene-azaindole derivatives (PCT WO 94/14808, published Jul. 7, 1994 by Ballinari et al.), 1-cyclopropyl-4-pyridyl-quinolones (U.S. Pat. No. 5,330,992), styryl compounds (U.S. Pat. No. 5,217,999), styryl-substituted pyridyl compounds (U.S. Pat. No. 5,302,606), certain quinazoline derivatives (EP Application No. 0 566 266 A1), seleoindoles and selenides (PCT WO 94/03427, published Feb. 17, 1994 by Denny et al.), tricyclic polyhydroxylic compounds (PCT WO 92/21660, published Dec. 10, 1992 by Dow), and benzylphosphonic acid compounds (PCT WO 91/15495, published Oct. 17, 1991 by Dow et al). The compounds that can traverse cell membranes and are resistant to acid hydrolysis are potentially advantageous therapeutics as they can become highly bioavailable after being administered orally to patients. However, many of these protein kinase inhibitors only weakly inhibit the function of protein kinases. In addition, many inhibit a variety of protein kinases and will therefore cause multiple side-effects as therapeutics for diseases.

Some indolinone compounds, however, form classes of acid resistant and membrane permeable organic molecules. WO 96/22976, published Aug. 1, 1996 by Ballinari et al. describes hydrosoluble indolinone compounds that harbor tetralin, naphthalene, quinoline, and indole substituents fused to the oxindole ring. These bicyclic substituents are in turn substituted with polar moieties including hydroxylated alkyl, phosphate, and ether moieties. U.S. patent application Ser. No. 08/702,232, filed Aug. 23, 1996, entitled "Indolinone Combinatorial Libraries and Related Products and Methods for the Treatment of Disease" by Tang et al. and Ser. No. 08/485,323, filed Jun. 7, 1995, entitled "Benzylidene-Z-Indoline Compounds for the Treatment of Disease" by Tang et al. and International Patent Publication WO 96/22976, published Aug. 1, 1996 by Ballinari et al., all of which are incorporated herein by reference in their entirety, including any drawings, describe indolinone chemical libraries of indolinone compounds harboring other bicyclic moieties as well as monocyclic moieties fused to the oxindole ring. Applications Ser. No. 08/702,232, filed Aug. 23, 1996, entitled "Indolinone Combinatorial Libraries and Related Products and Methods for the Treatment of Disease" by Tang et al. Ser. No. 08/485,323, filed Jun. 7, 1995, entitled "Benzylidene-Z-Indoline Compounds for the Treatment of Disease" by Tang et al. and WO 96/22976, published Aug. 1, 1996 by Ballinari et al. teach methods of indolinone synthesis, methods of testing the biological activity of indolinone compounds in cells, and inhibition patterns of indolinone derivatives.

Other examples of substances capable of modulating hWART activity include, but are not limited to, tyrphostins, quinazolines, quinoxolines, and quinolines.

The quinazolines, tyrphostins, quinolines, and quinoxolines referred to above include well known compounds such as those described in the literature. For example, representative publications describing quinazoline include Barker et al., EPO Publication No. 0 520 722 Al; Jones et al., U.S. Pat. No. 4,447,608; Kabbe et al., U.S. Pat. No. 4,757,072; Kaul and Vougioukas, U.S. Pat. No. 5,316,553; Kreighbaum and Comer, U.S. Pat. No. 4,343,940; Pegg and Wardleworth, EPO Publication No. 0 562 734 Al; Barker et al., *Proc. of Am. Assoc. for Cancer Research* 32:327 (1991); Bertino, J. R., *Cancer Research* 3:293–304 (1979); Bertino, J. R., *Cancer Research* 9(2 part 1):293–304 (1979); Curtin et al., *Br. J. Cancer* 53:361–368 (1986); Fernandes et al., *Cancer Research* 43:1117–1123 (1983); Ferris et al. *J. Org. Chem.* 44(2):173–178; Fry et al., *Science* 265:1093–1095 (1994); Jackman et al., *Cancer Research* 51:5579–5586 (1981); Jones et al. *J. Med. Chem.* 29(6):1114–1118; Lee and Skibo, *Biochemistry* 26(23):7355–7362 (1987); Lemus et al., *J. Org. Chem.* 54:3511–3518 (1989); Ley and Seng, *Synthesis* 1975:415–522 (1975); Maxwell et al., *Magnetic Resonance in Medicine* 17:189–196 (1991); Mini et al., *Cancer Research* 45:325–330 (1985); Phillips and Castle, *J. Heterocyclic Chem.* 17(19):1489–1596 (1980); Reece et al., *Cancer Research* 47(11):2996–2999 (1977); Sculier et al., *Cancer Immunol. and Immunother.* 23:A65 (1986); Sikora et al., *Cancer Letters* 23:289–295 (1984); Sikora et al., *Analytical Biochem.* 172:344–355 (1988); all of which are incorporated herein by reference in their entirety, including any drawings.

Quinoxaline is described in Kaul and vougioukas, U.S. Pat. No. 5,316,553, incorporated herein by reference in its entirety, including any drawings.

Quinolines are described in Dolle et al., *J. Med. Chem.* 37:2627–2629 (1994); MaGuire, *J. Med. Chem.* 37:2129–2131 (1994); Burke et al., *J. Med. Chem.* 36:425–432 (1993); and Burke et al. *BioOrganic Med. Chem. Letters* 2:1771–1774 (1992), all of which are incorporated by reference in their entirety, including any drawings.

Tyrphostins are described in Allen et al., *Clin. Exp. Immunol.* 91:141–156 (1993); Anafi et al., *Blood* 82:12:3524–3529 (1993); Baker et al., *J. Cell Sci.* 102:543–555 (1992); Bilder et al., *Amer. Physiol. Soc.* pp. 6363–6143:C721–C730 (1991); Brunton et al., *Proceedings of Amer. Assoc. Cancer Rsch.* 33:558 (1992); Bryckaert et al., *Experimental Cell Research* 199:255–261 (1992); Dong et al., *J. Leukocyte Biology* 53:53–60 (1993); Dong et al., *J. Immunol.* 151(5):2717–2724 (1993); Gazit et al., *J. Med. Chem.* 32:2344–2352 (1989); Gazit et al., "*J. Med. Chem.* 36:3556–3564 (1993); Kaur et al., *Anti-Cancer Drugs* 5:213–222 (1994); Kaur et al., King et al., *Biochem. J.* 275:413–418 (1991); Kuo et al., *Cancer Letters* 74:197–202 (1993); Levitzki, A., *The FASEB J.* 6:3275–3282 (1992); Lyall et al., *J. Biol. Chem.* 264:14503–14509 (1989); Peterson et al., *The Prostate* 22:335–345 (1993); Pillemer et al., *Int. J. Cancer* 50:80–85 (1992); Posner et al., *Molecular Pharmacology* 45:673–683 (1993); Rendu et al., *Biol. Pharmacology* 44(5):881–888 (1992); Sauro and Thomas, *Life Sciences* 53:371–376 (1993); Sauro and Thomas, *J. Pharm. and Experimental Therapeutics* 267(3):119–1125 (1993); Wolbring et al., *J. Biol. Chem.* 269(36):22470–22472 (1994); and Yoneda et al., *Cancer Research* 51:4430–4435 (1991); all of which are incorporated herein by reference in their entirety, including any drawings.

Other compounds that could be used as modulators include oxindolinones such as those described in U.S. patent application Ser. No. 08/702,232 filed Aug. 23, 1996, incorporated herein by reference in its entirety, including any drawings.

EXAMPLES

The examples below are non-limiting and are merely representative of various aspects and features of the present invention. The examples below demonstrate the isolation and characterization of novel human WART nucleic acids and polypeptides.

Example 1

Cloning of Murine WART1

Total RNAs were isolated using the Guanidine Salts/Phenol extraction protocol of Chomczynski and Sacchi (P. Chomczynski and N. Sacchi, Anal. Biochem. 162:156, 1987) from murine embryos from gestational day 12. These RNA were used to generate single-stranded cDNA using the Superscript Preamplification System (GIBCO BRL, Gaithersburg, Md.; Gerard, G F et al., Focus 11:66, 1989). A typical reaction used 10 $\mu$g total RNA with 1.5 $\mu$g oligo(dT)$_{12-18}$ in a reaction volume of 60 $\mu$L. The product was treated with RNaseH and diluted to 100 $\mu$L with H$_2$O. For subsequent PCR amplification, 1–4 $\mu$L of the sscDNA was used in each reaction.

Degenerate oligonucleotides targeted for the Epidermal Growth Factor (EGF) family were synthesized on an Applied Biosystems 3948 DNA synthesizer using established phosphoramidite chemistry, precipitated with ethanol and used unpurified for PCR. The sequence of the degenerate oligonucleotide primers used were the following:
KITDFG=5'-CAYGTNAARATHACNGAYTTYGG-3' (SEQ ID NO:5) and
KCWMID=5'-GGRTCDATCATCCAGCAYTT-3' (SEQ ID NO:6).
These primers were derived from the sense and antisense strands, respectively of peptide sequences KITDFG (SEQ ID NO:7) and KCWMID (SEQ ID NO:8). Degenerate nucleotide residue designations are: N=A, C, G, or T; R=A or G; Y=C or T; H=A, C or T not G; and D=A, G or T not C.

PCR reactions were performed using degenerate primers applied to the murine day 12 embryo single-stranded cDNA. The primers were added at a final concentration of 5 $\mu$M each to a mixture containing 10 mM TrisHCL (pH 8.3), 50 mM KCL, 1.5 mM MgCl$_2$, 200 $\mu$M each deoxynucleoside triphosphate, 0.001% geletin, 1.5 U AmpliTaq DNA Polymerase (Perkin-Elmer/Cetus), and 1–4 $\mu$L cDNA. Following 3 min denaturation at 95° C., the cycling conditions were 94° C. for 30 s, 50° C. for 1 min, and 72° C. for 1 min 45 s for 35 cycles. PCR fragments migrating between 300–350 bp were isolated from 2% agarose gels using the GeneClean Kit (Bio101), and T-A cloned into the PCRII vector (Invitrogen Corp. U.S.A.) according to the manufacturer's protocol.

Colonies were selected for mini plasmid DNA-preparations using Qiagen columns and the plasmid DNA was sequenced using cycle sequencing dye-terminator kit with AmpliTaq DNA Polymerase, FS (ABI, Foster City, Calif.). Sequencing reaction products were run on an ABI Prism 377 DNA Sequencer, and analyzed using the BLAST alignment algorithm (Altschul, S. F. et al., J.Mol.Biol. 215:403–10). This analysis lead to the isolation of clone 105–4–10 corresponding to murine WART1.

Clone 105-4-10 exhibits 65% homology with the predicted amino acid sequence of the Drosophila serine-threonine kinase WART (Gene Bank (GB): L39847) using MPsrch_tnp (Oxford Molecular Group, UK) a DNA to protein pairwise search implementation of the Smith-Waterman algorithm. While the 5' primer recognized a sequence encoding the predicted kinase homology domain, the 3' primer hybridized to a sequence whose translation was out of frame with the peptide it had been designed to amplify. Nonetheless, the intervening sequence contained the expected kinase motifs.

Example 2 cDNA Cloning and Characterization of Human WART1

A second PCR strategy was designed to isolate the human orthologue of the novel mouse clone. Degenerate primers based on clone 105-4-10 were used to amplify templates derived from a pool of primary human non-small cell lung carcinomas. Total RNAs from primary human lung tumors were isolated as in Example 1. The sequence of the degenerate oligonucleotide primers used were as follows:

5774=5'-TCCRAACAGDATNACNCCNACNSWCCA-3' (SEQ ID NO:9) and

5326=5'-TTYGGNYTNTGYACNGGNTTYMGNTGG-3' (SEQ ID NO:10).

These primers were derived from the sense and antisense strands, respectively of peptide sequences FGLCTGFRW (SEQ ID NO:11) and WSVGVILFE (SEQ ID NO:12) present in the murine WART1 clone. The amplification conditions were similar to those described in Example 1 using oligonucleotides KITDFG (SEQ ID NO:7 and KCW-MID (SEQ ID NO:8). Two distinct PCR products were isolated, SuSTK15 (268 bp) and SuSTK17 (273 bp). These two fragments share 72% DNA identity and 88% amino acid sequence identity to one another. SuSTK15_h has been designated as hWART1 cDNA because it is more related to the murine WART1 cDNA (90% DNA identity; 98% amino acid identity), than SuSTK17_h (74% DNA sequence identity; 83% amino acid identity). SuSTK17_h has been designated as hWART2.

Example 3

Isolation of hWART1

A human bone marrow gt11 cDNA library was probed with the PCR fragments corresponding to human WART1. Probes were $^{32}$P-labeled by random priming and used at $2\times10^6$ cpm/mL following standard techniques known in the art for library screening. Prehybridization (3 h) and hybridization (overnight) were conducted at 42° C. in 5×SSC, 5×Denhart's solution, 2.5% dextran sulfate, 50 mM $Na_2PO_4$ [pH 7.0], 50% formamide with 100 mg/mL denatured salmon sperm DNA. Stringent washes were performed at 65° C. in 0.1×SSC and 0.1% SDS. DNA sequencing was carried out on both strains using a cycle sequencing dye-terminator kit with AmpliTaq DNA Polymerase, FS (ABI, Foster City, Calif.). Sequencing reaction products were run on an ABI Prism 377 DNA Sequencer.

Three cDNAs were isolated and completely sequenced. Two of the clones were found to be overlapping clones that encoded a long C-terminal open reading frame (ORF) but lacked an upstream stop codon. The third clone was found to contain no significant ORFs but was later found to encode the 3' untranslated region (UTR) of the human WART1 cDNA. Rescreening of the bone marrow cDNA library yielded two more cDNA clones which upon sequencing were found to contain a long ORF contiguous with the two clones isolated from the previous screening of the bone marrow cDNA library.

The full-length human WART1 cDNA is 7,382 bp long and consists of a 3,390 bp ORF. This ORF is flanked by 394 and 3,554 bp of 5' and 3' untranslated regions (UTR) respectively. A 41 nucleotide polyA-rich tail follows the 3' UTR. There are two potential start codons at positions 395 and 431, neither corresponding to the Kozak consensus for initiating methionines. Although the second start site aligns to the N-terminal sequence of the related WART2, we have designated position 395 as the start site since it is the first start site encountered in this extended ORF. There are two additional ATGs located 5' to the start codon at position 395, but they are followed by stop codons after 31 and 10 nucleotides, respectively. The 3,390 bp ORF has the potential to encode a 1,130 amino acid protein.

The 5' UTR from nucleotide 12–63 displays 10 copies of the tri-nucleotide repeat, GGC. This repeat is very similar to one found in the human retinoid X receptor beta (GB:M84820). Such repeats have been reported to undergo expansion in various human diseases particulary those associated with neuronal phenotypes. The 3' UTR contains an inverted 289 bp Alu-J subfamily repeat (between nucleotides 6,058–6,346). A polyadenylation signal (AATAAA) is found at position 7,338 followed by a 20 nucleotide long polyadenylated stretch.

Sequence analysis of multiple cDNA clones identified three polymorphisms in the human WART1 gene: (1) at nucleotide 978 resulting in an Ala/Gly change; (2) at nucleotide 1,840, silent; (3) at nucleotides 3,252–3,253 comprising a deletion of two adenosines that results in a C-terminal truncation of the hWART1 gene, disrupting the putative kinase domain. The frame shift mutation at position 3252 was observed in two independent clones isolated from the human bone marrow cDNA source. The non-mutated sequence, however, was also confirmed in multiple independent clones. Conceivably, truncation of the WART1 Serine-threonine kinase could play a role in disease progression.

Example 4

Isolation of cDNA Encoding the hWART2 Gene

SuSTK17_h was used as a probe to screen a λ.gt11 human bone marrow cDNA library. Multiple cDNA clones were isolated and two (W2D4 and W2D1.8) were sequenced fully on both strands. Clone W2D4 lies 5' of clone W2D1.8 separated by an internal EcoRI site in the full-length hWART2 cDNA.

The full-length 5,276 bp hWART2 cDNA consists of a 3,264 bp ORF flanked by 394 and 1,612 bp of 5' and 3' UTRs, respectively. A 23 nucleotide polyA-rich tail follows the 3' UTR. This ORF has the potential to encode a 1,088 amino acid polypeptide. Based on amino acid sequence homology to the Drosophila and human WART1 proteins we believe that this ORF encodes the hWART2 protein. There are 5 additional ORF's none longer than 144 nucleotides, 5' to nucleotide 375. The ATG at position 375 fits the Kozak consensus for translational initiation.

Example 5

Distribution of Human WART1 and WART2 mRNA in Normal Tissues and Tumor Cell Lines Northern blots were obtained from Clontech (Palo Alto, Calif.) containing 2 μg polyA+ RNA from 16 different adult human tissues (spleen, thymus, prostate, testis, ovary, small intestine, colonic mucosa, heart, brain, placenta, lung, liver, skeletal muscle, kidney, pancreas, and peripheral blood leukocytes), and four different human fetal tissues (brain, lung, liver, and kidney), on charge-modified nylon membrane. Additional Northern blots were prepared by running 20 gg total RNA on formaldehyde 1.2% agarose gel and transferring to nylon membranes.

Filters were hybridized with random prime [$^{32}$P]dCTP-labeled probes synthesized from the 270 bp inserts from SuSTK15 (hWART1) or SuSTK17 (hWART2). Hybridization was performed at 6020 C. overnight in 6×SSC, 0.1% SDS, 1×Denhardt's solution, 100 mg/mL denatured herring s with 1–2'10$^6$ cpm/mL of $^{32}$P-labeled DNA probes. The filters were washed in 0.1×SSC/0.1% SDS, 65° C., and exposed overnight on Kodak XAR-2 film.

hWART1 RNA expression was not detected in 18 normal samples tested. Similarly hWART2 expression was undetectable in 15 of the 18 samples, but was seen in three hormonally responsive tissues: uterus, prostate, and testis.

Expression of hWART1 and hWART2 was next examined in a panel of human tumor cell lines representing a diverse sampling of tumor types. hWART1 showed strong expression in cell lines from non-small cell lung cancer, ovarian tumors, central nervous system tumors, renal tumors, and breast tumors. hWART2 expression was consistently expressed, although usually at lower levels than hWART1 in virtually all samples tested, except for most of the colon cancer lines. The robust overexpression of hWART1 and hWART2 in tumor cells versus normal tissues may provide an attractive target for oncology drug development. The tissue distribution of hWART1 and hWART2 mRNA is summarized in Table 1.

TABLE 1

Expression of hWART1 and hWART2 in various tissues

| Cell type | Origin | hWART1* expression | hWART2* expression |
|---|---|---|---|
| Brain | Normal tissue | 0 | 0 |
| Cerebellum | Normal tissue | 0 | 0 |
| Thymus | Normal tissue | 0 | 0 |
| Salivary Gland | Normal tissue | 0 | 0 |
| Lung | Normal tissue | 0 | 0 |
| Heart | Normal tissue | 0 | 0 |
| Liver | Normal tissue | 0 | 0 |
| Pancreas | Normal tissue | 0 | 0 |
| Kidney | Normal tissue | 0 | 0 |
| Stomach | Normal tissue | 0 | 0 |
| Duodenum | Normal tissue | 0 | 0 |
| Uterus | Normal tissue | 0 | 0 |
| Prostate | Normal tissue | 0 | 1 |
| Skel. Muscle | Normal tissue | 0 | 0 |
| Placenta | Normal tissue | 0 | 0 |
| Fetal Brain | Normal tissue | 0 | 0 |
| Mammary Gland | Normal tissue | 0 | 0 |
| Testis | Normal tissue | 0 | 1 |
| HOP-92 | Lung tumor | 1 | 1 |
| EKVX | Lung tumor | 2 | 1 |
| NCI-H23 | Lung tumor | 4 | 1 |
| NCI-H226 | Lung tumor | 3 | 1 |
| NCI-H322M | Lung tumor | 4 | 1 |
| NCI-H460 | Lung tumor | 1 | 0 |
| NCI-H522 | Lung tumor | 1 | 1 |
| A549 | Lung tumor | 1 | 0 |
| HOP-62 | Lung tumor | 1 | 0 |
| OVCAR-3 | Ovarian tumor | 0 | 0 |
| OVCAR-4 | Ovarian tumor | 1 | 1 |
| OVCAR-5 | Ovarian tumor | 1 | 1 |
| OVCAR-8 | Ovarian tumor | 1 | 1 |
| IGROV1 | Ovarian tumor | 2 | 1 |
| SK-OV-3 | Ovarian tumor | 4 | 1 |
| SNB-19 | CNS tumor | 4 | 0 |
| SNB-75 | CNS tumor | 1 | 1 |
| U251 | CNS tumor | 2 | 1 |
| SF-268 | CNS tumor | 3 | 3 |
| SF-295 | CNS tumor | 1 | 1 |
| SF-539 | CNS tumor | 3 | 1 |
| CCRF-CEM | Leukemia | 3 | 0 |
| K-562 | Leukemia | 4 | 0 |
| MOLT-4 | Leukemia | 1 | 0 |
| HL-60 | Leukemia | 0 | 0 |
| RPMI 8226 | Leukemia | 1 | 0 |
| SR | Leukemia | 1 | 1 |
| DU-145 | Prostate | 1 | 1 |
| PC-3 | Prostate | 1 | 0 |
| HT-29 | Colon tumor | 0 | 0 |
| HCC-2998 | Colon tumor | 0 | 0 |
| HCT-116 | Colon tumor | 0 | 0 |
| SW620 | Colon tumor | 0 | 0 |
| Colo 205 | Colon tumor | 0 | 0 |
| HTC15 | Colon tumor | 2 | 1 |
| KM-12 | Colon tumor | 0 | 0 |
| UO-31 | Colon tumor | 0 | 1 |
| SN12C | Kidney tumor | 0 | 3 |
| A498 | Kidney tumor | 0 | 0 |
| CaKil | Kidney tumor | 2 | 2 |
| RXF-393 | Kidney tumor | 2 | 1 |
| ACHN | Kidney tumor | 0 | 0 |
| 786-0 | Kidney tumor | 3 | 0 |
| TK-10 | Kidney tumor | 3 | 4 |
| LOX IMVI | Melanoma | 3 | 2 |
| Malme-3M | Melanoma | 0 | 1 |
| SK-MEL-2 | Melanoma | 1 | 1 |
| SK-MEL-5 | Melanoma | 0 | 1 |
| SK-MEL-28 | Melanoma | 1 | 1 |
| UACC-62 | Melanoma | 4 | 1 |
| UACC-257 | Melanoma | 1 | 1 |
| M14 | Melanoma | 1 | 1 |
| MCF-7 | Breast tumor | 3 | 1 |
| MCF-7/ADR RES | Breast tumor | 1 | 1 |
| Hs578T | Breast tumor | 1 | 1 |
| MDA-MB-231 | Breast tumor | 0 | 1 |
| MDA-MB-435 | Breast tumor | 0 | 0 |
| MDA-N | Breast tumor | 0 | 1 |
| BT-549 | Breast tumor | 1 | 1 |
| T47D | Breast tumor | 4 | 1 |

*No expression is represented by 0 and maximal expression is represented by 4.

Example 6 hWART1 and hWART2 Expression Vector Construction

Full length expression constructs were generated for hWART1 and hWART2 from fully sequenced cDNA clones. These intact ORFs were inserted into pCDNAII (Invitrogen) or pRK5 for transient expression in mammalian cells. The hWART constructs were also tagged, by PCR mutagenesis, at their carboxy-terminal ends with the *Haemophilus influenza* hemaglutinin (HA) epitope YPYDVPDYAS (SEQ ID NO:14) (U.K. Pati, Gene 114:285–288, 1992).

An N-terminal myristolated form of both hWART1 and hWART2 were also generated by addition of a 5' amino tag to both proteins by PCR mediated mutagenesis using techniques known to those skilled in the art. These altered fragments were inserted into the same expression vectors. These expression constructs will allow targeting of the recombinant WART proteins to the membrane, potentially enhancing or deregulating their biologic effects.

Dominant negative forms of hWART1 and hWART2 can be constructed by a lysine to alanine substitution at the ATP-binding site in their kinase domains.

Example 7

Generation of hWART1- and hWART2-specific Immunoreagents hWART1- and hWART2-specific immunoreagents were raised in rabbits against KLH-conjugated synthetic peptides specific to the two proteins. The peptides were conjugated to a cysteine added to the C-terminal end of each peptide, using techniques known to those skilled in the art. Amino acid sequences of the peptide immunogens and their location within the human WART1 and WART2 sequences are:
hWART1:
ISKPSKEDQPSLPK (SEQ ID NO:15) (aa576–589) N-terminal to kinase domain.
DDQNTGSEIKNRDLVYV (SEQ ID NO:16) (aa1114–1130) C-terminus.
hWART2
PsgKNSRDEEKRESRI (SEQ ID NO:17) (aa579–594) N-terminal to kinase domain.
SDLVDQTEGCQPVYV (SEQ ID NO:18) (1074–1088) C-terminus.
SEQ ID NO:17 has 2 amino acid differences from the hWART2 sequence, due to only partial sequence information present at the time of its synthesis. These changes have no apparent effect on the specificity of the antisera generated using it as an immunogen.

Example 8

Transient Expression of hWART1 and hWART2 Constructs in Mammalian Cells

The hWART1 and hWART2 expression plasmids (10 g DNA/100 mm plate) containing the wild type or HA-tagged hWART1, wild type or HA-tagged hWART2 or the myristolated forms of hWART1 and hWART2 were introduced into COS and 293 cells with lipofectamine (Gibco BRL). After 72 hours, the cells were harvested in 0.5 mL solubilization buffer (20 mM Hepes pH 7.35, 150 mM NaCl, 10% glycerol, 1% Triton X-100, 1.5 mM $MgCl_2$, 1 mM EGTA, 2 mM phenylmethylsulfonyl fluoride, 1 µg/mL aprotinin). Sample aliquots were resolved by SDS polyacrylamide gel electrophoresis (PAGE) on 8% acrylamide/0.5% bis-acrylamide gels and electrophoretically transferred to nitrocellulose. Non-specific binding was blocked by preincubating blots in Blotto (phosphate buffered saline containing 5% w/v non-fat dried milk and 0.2% v/v nonidet P-40 (Sigma)), and recombinant protein was detected using a murine Mab to the HA decapeptide tag. Alternatively, recombinant protein can be detected using various hWART1- or hWART2-specific antisera.

Example 9

Screening Systems for the Identification of Inhibitors of hWART Activity

Assays may be performed in vitro or in vivo and are described in detail herein or can be obtained by modifying existing assays, such as the growth assay described in patent application Ser. No. 08/487,088, filed Jun. 7, 1995, by Tang et al., and entitled "Novel Pharmaceutical Compounds", or the assays described in patent application Ser. No. 60/005, 167, filed Oct. 13, 1995 by Seedorf et al., and entitled "Diagnosis and Treatment of TKA-1 related disorders", all of which are hereby incorporated herein by reference in their entirety including any drawings. Another assay which could be modified to use the genes of the present invention is described in International Application No. WO 94/23039, published Oct. 13, 1994, hereby incorporated herein by reference in its entirety including any drawings. Other possibilities include detecting kinase activity in an autophosphorylation assay or testing for kinase activity on standard substrates such as histones, myelin basic protein, gamma tubulin, or centrosomal proteins. Binding partners may be identified by putting the N-terminal portion of the protein into a two-hybrid screen or detecting phosphotyrosine of a dual specificity kinase (Fields and Song, U.S. Pat. No. 5,283,173, issued Feb. 1, 1994, incorporated by reference herein, including any drawings).

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

In view of the degeneracy of the genetic code, other combinations of nucleic acids also encode the claimed peptides and proteins of the invention. For example, all four nucleic acid sequences GCT, GCC, GCA, and GCG encode the amino acid alanine. Therefore, if for an amino acid there exists an average of three codons, a polypeptide of 100 amino acids in length will, on average, be encoded by $3^{100}$, or $5 \times 10^{47}$, nucleic acid sequences. It is understood by those skilled in the art that, with, Thus, a nucleic acid sequence can be modified to form a second nucleic acid sequence, encoding the same polypeptide as endoded by the first second nucleic acid sequences, using routine procedures and without undue experimentation. Thus, all possible nucleic acids that encode the claimed peptides and proteins are also fully described herein, as if all were written out in full taking into account the codon usage, especially that preferred in humans.

Furthermore, changes in the amino acid sequences of polypeptides, or in the corresponding nucleic acid sequence encoding such polypeptide, may be designed or selected to take place in an area of the sequence where the significant activity of the polypeptide remains unchanged. For example, an amino acid change may take place within a –turn, away from the active site of the polypeptide. Also changes such as deletions (e.g. removal of a segment of the polypeptide, or in the corresponding nucleic acid sequence encoding such polypeptide, which does not affect the active site) and additions (e.g. addition of more peptides to the polypeptide sequence without affecting the function of the active site, such as the formation of GST-fusion proteins, or additions in the corresponding nucleic acid sequence encoding such polypeptide without affecting the function of the active site) are also within the scope of the present invention. Such changes to the polypeptides can be performed by those with ordinary skill in the art using routine procedures and without undue experimentation. Thus, all possible nucleic and/or amino acid sequences that can readily be determined not to affect a significant activity of the peptide or protein of the invention are also fully described herein.

Other embodiments are within the following claims.

What is claimed is:

1. An isolated enriched, or purified nucleic acid molecule wherein said nucleic acid molecule comprises a nucleotide sequence that
    (a) encodes a polypeptide having the full length amino acid sequence of SEQ ID NO:3; or
    (b) is the complement of (a).

2. The nucleic acid molecule of claim 1, wherein said nucleic acid molecule is isolated, enriched, or purified from a mammal.

3. The nucleic acid molecule of claim 2, wherein said mammal is a human.

4. A nucleic acid molecule comprising the nucleic acid sequence set forth in SEQ ID NO:1.

5. The nucleic acid molecule of claim 1 or claim 4, further comprising a vector or promoter effective to initiate transcription in a host cell.

6. A nucleic acid molecule comprising the nucleotide sequence of claim 1 or claim 4, wherein said nucleotide sequence is fused to a nucleic acid sequence encoding a non-WART polypeptide.

7. A method for identifying a substance capable of modulating hWART function in a cell comprising the steps of:
    (a) expressing the polypeptide encoded by the nucleic molecule of claim 1 or claim 4 in a cell;
    (b) adding a test substance to the cell; and
    (c) monitoring a change in either cell phenotype, cell proliferation, cell differentiation, or catalytic activity.

8. The nucleic acid molecule according to claim 5, wherein said vector comprises at least one of an origin of replication, a ribosomal binding site, a nucleic acid sequence encoding a drug resistance enzyme, and nucleic acid sequences encoding secretion signals, periplasm or peroxisome localization signals, or signals useful for polypeptide purification.

9. A recombinant cell, comprising the nucleic acid molecule of claim 1.

10. A recombinant cell, comprising the nucleic acid molecule of claim 4.

11. A recombinant cell, comprising the nucleic acid molecule of claim 1 fused to a nucleic acid sequence encoding a non-WART polypeptide.

12. A recombinant cell, comprising the nucleic acid molecule of claim 4 fused to a nucleic acid sequence encoding a non-WART polypeptide.

13. An isolated enriched, or purified nucleic acid molecule wherein said nucleic acid molecule comprises a nucleotide sequence that
    (a) encodes a polypeptide having the full length amino acid sequence of SEQ ID NO:4; or
    (b) is the complement of (a).

14. The nucleic acid molecule of claim 13, wherein said nucleic acid molecule is isolated, enriched, or purified from a mammal.

15. The nucleic acid molecule of claim 14, wherein said mammal is a human.

16. An isolated, purified, or enriched nucleic acid molecule that
    (a) encodes a polypeptide consisting of amino acid residues 666–973 or 974–1048 of SEQ ID NO:4; or
    (b) is the complement of the nucleotide sequence of (a).

17. A nucleic acid molecule comprising a nucleotide sequence
    (a) encoding amino acid residues 666–973 of SEQ ID NO:4; or
    (b) is the complement of the nucleotide sequence of (a).

18. A nucleic acid molecule comprising the nucleic acid sequence set forth in SEQ ID NO:2.

19. The nucleic acid molecule of claim 13 or claim 18, further comprising a vector or promoter effective to initiate transcription in a host cell.

20. The nucleic acid molecule according to claim 19, wherein said vector comprises at least one of an origin of replication, a ribosomal binding site, a nucleic acid sequence encoding a drug resistance enzyme, and nucleic acid sequences encoding secretion signals, periplasm or peroxisome localization signals, or signals useful for polypeptide purification.

21. A nucleic acid molecule comprising the nucleotide sequence of claim 13, claim 16, claim 17, or claim 18, wherein said nucleotide sequence is fused to a nucleic acid sequence encoding a non-WART polypeptide.

22. A method for identifying a substance capable of modulating hWART function in a cell comprising the steps of:
    (a) expressing the polypeptide encoded by the nucleic acid molecule of claim 13, claim 16, claim 17, or claim 18 in a cell;

(b) adding a test substance to the cell; and (c) monitoring a change in either cell phenotype, cell proliferation, cell differentiation, or catalytic activity.

23. A recombinant cell, comprising the nucleic acid molecule set forth in any one of claim 13, claim 16, claim 17, or claim 18.

24. A recombinant cell, comprising the nucleic acid molecule set forth in any one of claim 13, claim 16, claim 17, or claim 18 fused to a nucleic acid sequence encoding a non-WART polypeptide.

* * * * *

SEQUENCE LISTING

<160> NUMBER OF SEQ ID NOS: 18

<210> SEQ ID NO 1
<211> LENGTH: 7382
<212> TYPE: DNA
<213> ORGANISM: HUMAN

<400> SEQUENCE: 1

| | | | | | | |
|---|---|---|---|---|---|---|
| cagcggagtg | cggcggcggc | gacactgagt | ggaaggcaaa | atggcggcgg | cggcggcggt | 60 |
| ggcctggtgt | taagggggaga | gccaggtcct | cacgacccct | gggacgggcc | gcgctggccc | 120 |
| gcggcagccc | ccccgttcgt | ctccccgctc | tgccccacca | gggatacttg | gggttgctgg | 180 |
| gacggactct | ggccgcctca | gcgtccgccc | tcaggcccgt | ggccgctgtc | caggagctct | 240 |
| gctctcccct | ccagagttaa | ttatttatat | tgtaaagaat | tttaacagtc | ctggggactt | 300 |
| ccttgaagga | tcattttcac | ttttgctcag | aagaaagctc | tggatctatc | aaataaagaa | 360 |
| gtccttcgtg | tgggctacat | atatagatgt | tttcatgaag | aggagtgaaa | agccagaagg | 420 |
| atatagacaa | atgaggccta | agacctttcc | tgccagtaac | tatactgtca | gtagccggca | 480 |
| aatgttacaa | gaaattcggg | aatcccttag | gaatttatct | aaaccatctg | atgctgctaa | 540 |
| ggctgagcat | aacatgagta | aaatgtcaac | cgaagatcct | cgacaagtca | gaaatccacc | 600 |
| caaatttggg | acgcatcata | aagccttgca | ggaaattcga | aactctctgc | ttccatttgc | 660 |
| aaatgaaaca | aattcttctc | ggagtacttc | agaagttaat | ccacaaatgc | ttcaagactt | 720 |
| gcaagctgct | ggatttgatg | aggatatggt | tatacaagct | cttcagaaaa | ctaacaacag | 780 |
| aagtatagaa | gcagcaattg | aattcattag | taaaatgagt | taccaagatc | ctcgacgaga | 840 |

-continued

```
gcagatggct gcagcagctg ccagacctat taatgccagc atgaaaccag ggaatgtgca      900
gcaatcagtt aaccgcaaac agagctggaa aggttctaaa gaatccttag ttcctcagag      960
gcatggcccg ccactagcag aaagtgtggc ctatcattct gagagtccca actcacagac     1020
agatgtagga agacctttgt ctggatctgg tatatcagca tttgttcaag ctcaccctag     1080
caacggacag agagtgaacc ccccaccacc acctcaagta aggagtgtta ctcctccacc     1140
acctccaaga ggccagactc cccctccaag aggtacaact ccacctcccc cttcatggga     1200
accaaactct caaacaaagc gctattctgg aaacatggaa tacgtaatct cccgaatctc     1260
tcctgtccca cctggggcat ggcaagaggg ctatcctcca ccacctctca acacttcccc     1320
catgaatcct cctaatcaag gacagagagg cattagttct gttcctgttg gcagacaacc     1380
aatcatcatg cagagttcta gcaaatttaa cttteccatca gggagacctg gaatgcagaa     1440
tggtactgga caaactgatt tcatgataca ccaaaatgtt gtccctgctg gcactgtgaa     1500
tcggcagcca ccacctccat atcctctgac agcagctaat ggacaaagcc cttctgcttt     1560
acaaacaggg ggatctgctg ctccttcgtc atatacaaat ggaagtattc ctcagtctat     1620
gatggtgcca aacagaaata gtcataacat ggaactatat aacattagtg tacctggact     1680
gcaaacaaat tggcctcagt catcttctgc tccagcccag tcatccccga gcagtgggca     1740
tgaaatccct acatggcaac ctaacatacc agtgaggtca aattctttta ataacccatt     1800
aggaaataga gcaagtcact ctgctaattc tcagccttct gctacaacag tcactgcaat     1860
tacaccagct cctattcaac agcctgtgaa agtatgcgt gtattaaaac cagagctaca     1920
gactgcttta gcacctacac acccttcttg gataccacag ccaattcaaa ctgttcaacc     1980
cagtcctttt cctgagggaa ccgcttcaaa tgtgactgtg atgccacctg ttgctgaagc     2040
tccaaactat caaggaccac caccacccta cccaaaacat ctgctgcacc aaaacccatc     2100
tgttcctcca tacgagtcaa tcagtaagcc tagcaaagag gatcagccaa gcttgcccaa     2160
ggaagatgag agtgaaaaga gttatgaaaa tgttgatagt ggggataaag aaaagaaaca     2220
gattacaact tcacctatta ctgttaggaa aaacaagaaa gatgaagagc gaagggaatc     2280
tcgtattcaa agttattctc ctcaagcatt taaattcttt atggagcaac atgtagaaaa     2340
tgtactcaaa tctcatcagc agcgtctaca tcgtaaaaaa caattagaga atgaaatgat     2400
gcgggttgga ttatctcaag atgcccagga tcaaatgaga aagatgcttt gccaaaaaga     2460
atctaattac atccgtctta aaagggctaa aatggacaag tctatgtttg tgaagataaa     2520
gacactagga ataggagcat ttggtgaagt ctgtctagca agaaaagtag atactaaggc     2580
tttgtatgca acaaaaactc ttcgaaagaa agatgttctt cttcgaaatc aagtcgctca     2640
tgttaaggct gagagagata tcctggctga agctgacaat gaatgggtag ttcgtctata     2700
ttattcattc caagataagg acaatttata ctttgtaatg gactacattc ctgggggtga     2760
tatgatgagc ctattaatta gaatgggcat cttttccagaa agtctggcac gattctacat     2820
agcagaactt acctgtgcag ttgaaagtgt tcataaaatg ggttttattc atagagatat     2880
taaacctgat aatattttga ttgatcgtga tggtcatatt aaattgactg actttggcct     2940
ctgcactggc ttcagatgga cacacgattc taagtactat cagagtggtg accatccacg     3000
gcaagatagc atggatttca gtaatgaatg ggggatccc tcaagctgtc gatgtggaga     3060
cagactgaag ccattagagc ggagagctga acgccagcac cagcgatgtc tagcacattc     3120 tttggtttggg actcccaatt atattgcacc tgaagtgttg ctacgaacag atacacaca     3180 gttgtgtgat tggtggagtg ttggtgttat tctttttgaa atgttggtgg acaacctcc     3240
```

```
tttcttggca caaacaccat tagaaacaca aatgaaggtt atcaactggc aaacatctct   3300
tcacattcca ccacaagcta aactcagtcc tgaagcttct gatcttatta ttaaactttg   3360
ccgaggaccc gaagatcgct taggcaagaa tggtgctgat gaaataaaag ctcatccatt   3420
ttttaaaaca attgacttct ccagtgacct gagacagcag tctgcttcat acattcctaa   3480
aatcacacac ccaacagata catcaaattt tgatcctgtt gatcctgata aattatggag   3540
tgatgataac gaggaagaaa atgtaaatga cactctcaat ggatggtata aaatggaaa    3600
gcatcctgaa catgcattct atgaatttac cttccgaagg ttttttgatg acaatggcta   3660
cccatataat tatccgaagc ctattgaata tgaatacatt aattcacaag gctcagagca   3720
gcagtcggat gaagatgatc aaaacacagg ctcagagatt aaaaatcgcg atctagtata   3780
tgtttaacac actagtaaat aaatgtaatg aggatttgta aagggcctg aaatgcgagg    3840
tgttttgagg ttctgagagt aaaattatgc aaatatgaca gagctatata tgtgtgctct   3900
gtgtacaata ttttattttc ctaaattatg ggaaatcctt ttaaaatgtt aatttattcc   3960
agccgtttaa atcagtattt agaaaaaaat tgttataagg aaagtaaatt atgaactgaa   4020
tattatagtc agttcttggt acttaaagta cttaaaataa gtagtgcttt gtttaaaagg   4080
agaaacctgg tatctatttg tatatatgct aaataatttt aaaatacaag agttttgaa    4140
attttttga aagacagttt tagttttatc ttgctttaac caaatatgaa acataccccc    4200
tattttacag agctcttttt tcccctcata accttgtttt tggtagaaaa taagctagag   4260
aaattaagcc atcgtgttgg tgagtgttcc taggctaatg ataatctgta taattcacat   4320
cctgaaacta aggaatacag ggttgaaaaa atattaaat gtttgtcaga aggaaaaata    4380
atgcatttat cttcccccc acccccgcc ccatggaata tttaatctat ttaatcttct     4440
tgcatttatt tctcaagaat tactggcttt aaaagaagcc aaagcactac tagcttttt    4500
tccatattgg tattttgat gctgcttcca attttaaaag ggaacaaagc tgccataaat    4560
cgaaatgttc aatactaaaa gctaaaatat ttctcaccat cctaagcaga taattatttt   4620
aattttcata tactttcct gtatagtaac tattttgatt atatcatcaa tgttacctgt    4680
ttcctctttc agaacagtgc tgcatataca gattgttatt ggcaaaggaa aatctggcta   4740
tctggcaata ttttacctaa gcgcagatta attggtgaaa aaattaactc ttaagatggc   4800
cattaataat taggaaagtt tacagagtgg tcttagtaga aaattcaagt cctcctaatt   4860
tatttaaggt tcaataatgc gttcaacatg cctgttatgt ataacgctta ggttctaagg   4920
aagattaagg tttcatacca aaatacatgt agcttatctt ttaggaaggg gaaaaaggct   4980
ccattttgac catagtaaaa tttgtgttgt gttttatttc cttttcttaa gctccactga   5040
taagggattg ttttatcaa aagttactat ttgtagattg gaggcataat tttagtgatt    5100
ttcatacttt tagctttctt cgcataaaag ctaattgaaa ccgtatatgt agtaaaatta   5160
aaggcagagc tgttgcagtt gaattggaga gttagggcaa agaacactta ttagcccaca   5220
cttcccacct ttctacaggt ggtcctttca gagctcagcc tgaaacccca ctactgtgtt   5280
atcgtgcgtc ttttgggggtt agtggttctt ttgagaatct gaaggaagct gtggactctt   5340
cctagaaaaa aaaccacac atacacatac aatgttgcat gcagtttcaa gggattttgg   5400
acatattgaa acctatcaca ggctgtaggt tatggacctc tgtgccatga gaaaattgat   5460
acattaaact aagaactttg tttttaactt accaatcact actcagcaca tcttatataa   5520
gctgataatt tgtgatggaa aaggtctgta gcatgtgata taaggtgacc ttatgaatgc   5580
```

-continued

| | |
|---|---|
| ctctcttgct ggtacattaa gttgttttaa tatatcattt ggaggggact gaaatgttag | 5640 |
| gctcattaca agcttgatac agaaatattt ctgaaggatt tctaatcaga attgtaaaac | 5700 |
| aatgtgctat catgaaatcg cagtcttcac ctcatggttc atggaacatt tggttagtcc | 5760 |
| cataaaatcc tatgcaaaac aaagtagttc aagaattttt aggtgggtag tcacatttat | 5820 |
| aaggtattcc tcttactctt tgggcttttt cagtctgatt tatttaaatt ttcatttagt | 5880 |
| tgttttactt ttggactaag gtgcaataca gtagaagata actttgttac atttatgttg | 5940 |
| taggaaaact aaggtgctgt ctcctccccc ttcccttccc acaaaatctg tattccccct | 6000 |
| attgctgaaa tgtaacagac actacaaatt ttgtattctt tttttgtttt ttgttttgag | 6060 |
| acagggtctc actctgtcac ccaggctgga gggcagtggc gcttcacagc tcactgcatc | 6120 |
| ctcaaccttg gggctcacg cagtcctccc gcctcagcct cccaagtagc tgggcatgcg | 6180 |
| ccaccaagcc cagctaattt ttgtatcttt agtagagatg gggtttcgcc atgttgccca | 6240 |
| ggttggtgtg gaattcctgg gctccagtta tatgcccacc tcagcctccc aaagtgctgg | 6300 |
| gattacagac gtgacccacc gcgcctggcg caaatatgta ttcttttaaa atttcctctg | 6360 |
| atactataag cttttttgcat ttatctgaag cagtatacat gcctttggta tcagcaattt | 6420 |
| taacagtttg gatatactta tcagctatct tattccaaaa ctacatctac ttcttccagt | 6480 |
| atagaatctg gtgcttcctg accaaaaaga tgagaaaaac aatgttaaaa atatagatgc | 6540 |
| tttccattga aatggagtga aaacattggt tctatatgtt ttcttttaaa ataattttct | 6600 |
| tattaaaaac ttgctgtctt tattatactt accctttta tgcatatcaa tagtatttat | 6660 |
| aagatgtgtt ctataattat gtaattgtag atactgttat gcattgtcca gtgcatcat | 6720 |
| aaggcaggcc ctactgctgt atcttttcta ccttcttatt tgtaatagaa actatagaat | 6780 |
| gtatgactaa aaagtcactt tgagattgac ttttttaaaa agttattacc ttctgctgtt | 6840 |
| gcaaagtgca aaactgtgag tggaattgtt ttattctgac ttaatgtgtt agaaattaga | 6900 |
| gaatacagtg ggaggatttt tagacattgc tgctgctgtt acccaaggta ttttagataa | 6960 |
| aaaatttta ataaacatcc ctttggtatt taaagtggaa catttagcct gttcattta | 7020 |
| atctaaagca aaaagtaatt tgggtcaaaa tattggtata tttgtaaagc gccttaatat | 7080 |
| atcccttgt ggaaggcact acacagttta cttttatatt gtattgtgta tataagtatt | 7140 |
| ttgtattaaa attgaatcag tggcaacatt aaagttttat aaaatcatgc tttgttagaa | 7200 |
| aaagaattac agctttgcaa tataactaat tgtttcgcat aattctgaat gtaatagata | 7260 |
| tgaataatca gcctgtgttt ttaatgaact tatttgtatt ttcccaatca ttttctctag | 7320 |
| tgtaatgttt gctgggataa taaaaaaaat tcaaatcttt cgaaaaaaaa aaaaaaaaa | 7380 |
| aa | 7382 |

<210> SEQ ID NO 2
<211> LENGTH: 5276
<212> TYPE: DNA
<213> ORGANISM: HUMAN

<400> SEQUENCE: 2

| | |
|---|---|
| gccccgggaa gatggagcag tcgccgtcca cgccaccgcc gccgcccggg gctcccccgt | 60 |
| ccctgcgggg ccagcagcag ctccagccac cagtgcccgg tctcccggcg cgagaggccc | 120 |
| gggagccgcc ggccaggacg cccccgaggg tgtagaccgc gcccctgga gagagtgata | 180 |
| atcttcaaaa tgaagacttt ggaaaatttt aggttctcta taggaactac aaaaatggaa | 240 |
| ggaaagaaca ttttcaaaag gaaattattt tgaaagtatg tttacaacaa actgatacta | 300 |

-continued

```
ttgacagttt ttttttttaaa taataaaaca ctttaagaag attgtattta tggtaaaagg    360
aaactggact aacaatgagg ccaaagactt ttcctgccac gacttattct ggaaatagcc    420
ggcagcgact gcaagagatt cgtgagggt taaagcagcc atccaagtct tcggttcagg    480
ggctacccgc aggaccaaac agtgacactt ccctggatgc caaagtcctg gggagcaaag    540
atgccaccag gcagcagcag cagatgagag ccaccccaaa gttcggacct tatcagaaag    600
ccttgaggga aatcagatat tccttgttgc cttttgctaa tgaatcgggc acctctgcag    660
ctgcagaagt gaaccggcaa atgctgcagg aactggtgaa cgcaggatgc gaccaggaga    720
tggctggccg agctctcaag cagactggca gcaggagcat cgaggccgcc ctggagtaca    780
tcagcaagat gggctacctg gacccgagga atgagcagat tgtgcgggtc attaagcaga    840
cctccccagg aaagggctc atgccaaccc cagtgacgcg gaggcccagc ttcgaaggaa    900
ccggcgattc gtttgcgtcc taccaccagc tgagcggtac cccctacgag ggcccaagct    960
tcggcgctga cggccccacg gcgctggagg agatgccgcg gccgtacgtg gactaccttt   1020
tccccggagt cggcccccac gggcccgccc accagcacca gcacccaccc aagggctacg   1080
gtgccagcgt agaggcagca ggggcacact tcccgctgca gggcgcgcac tacgggcggc   1140
cgcacctgct ggtgcctggg gaaccccctgg gctacggagt gcagcgcagc ccctccttcc   1200
agagcaagac gccgccggag accggggt acgccagcct gcccacgaag ggccagggag   1260
gaccgccagg cgccggcctc gctttcccac ccctgccgc cgggctctac gtgccgcacc   1320
cacaccacaa gcaggccggt cccgcggccc accagctgca tgtgctgggc tcccgcagcc   1380
aggtgttcgc cagcgacagc cccccgcaga gcctgctcac tccctcgcgg aacagcctca   1440
acgtggacct gtatgaattg ggcagcacct ccgtccagca gtggccggct gccaccctgg   1500
cccgccggga ctccctgcag aagccgggcc tggaggcgcc gccgcgcgcg cacgtggcct   1560
tccggcctga ctgcccagtg cccagcagga ccaactcctt caacagccac cagccgcggc   1620
ccggtccgcc tggcaaggcc gagccctccc tgcccgcccc caacaccgtg acggctgtca   1680
cggccgcgca catcttgcac ccggtgaaga gcgtgcgtgt gctgaggccg agccgcaga   1740
cggctgtggg gccctcgcac cccgcctggg tgccgcgcc tgccccggcc ccgccccccg   1800
ccccgcccc ggctgcggag ggcttggacg ccaaggagga gcatgccctg gcgctgggcg   1860
gcgcaggcgc cttcccgctg gacgtggagt acgaggcccc agaccggagg tgcccgcctc   1920
cgccctaccc gaagcacctg ctgctgcgca gcaagtcgga gcagtacgac ctggacagcc   1980
tgtgcgcagg catggagcag agcctccgtg cgggccccaa cgagcccgag ggcggcgaca   2040
agagccgcaa aagcgccaag gggacaaag gcggaaagga taaaaagcag attcagacct   2100
ctcccgttcc cgtccgcaaa acagcagag acgaagagaa gagagagtca cgcatcaaga   2160
gctactcgcc atacgccttt aagttcttca tggagcagca cgtggagaat gtcatcaaaa   2220
cctaccagca gaaggttaac cggaggctgc agctggagca agaaatggcc aaagctggac   2280
tctgtgaagc tgagcaggag cagatgcgga agatcctcta ccagaaagag tctaattaca   2340
acaggttaaa gagggccaag atggacaagt ctatgtttgt caagatcaaa accctgggga   2400
tcggtgcctt tggagaagtg tgccttgctt gtaaggtgga cactcacgcc ctgtacgcca   2460
tgaagaccct aaggaaaaag gatgtcctga accggaatca ggtggcccac gtcaaggccg   2520
agagggacat cctggccgag gcagacaatg agtgggtggt caaactctac tactccttcc   2580
aagacaaaga cagcctgtac tttgtgatgg actacatccc tggtggggac atgatgagcc   2640
```

-continued

```
tgctgatccg gatggaggtc ttccctgagc acctggcccg gttctacatc gcagagctga   2700
ctttggccat tgagagtgtc cacaagatgg gcttcatcca ccgagacatc aagcctgata   2760
acattttgat agatctggat ggtcacatta aactcacaga tttcggcctc tgcactgggt   2820
tcaggtggac tcacaattcc aaatattacc agaaagggag ccatgtcaga caggacagca   2880
tggagcccag cgacctctgg gatgatgtgt ctaactgtcg gtgtggggac aggctgaaga   2940
ccctagagca gagggcgcgg aagcagcacc agaggtgcct ggcacattca ctggtgggga   3000
ctccaaacta catcgcaccc gaggtgctcc tccgcaaagg gtacactcaa ctctgtgact   3060
ggtggagtgt tggagtgatt ctcttcgaga tgctggtggg gcagccgccc ttttttggcac   3120
ctactcccac agaaacccag ctgaaggtga tcaactggga aacacgctc cacattccag   3180
cccaggtgaa gctgagccct gaggccaggg acctcatcac caagctgtgc tgctccgcag   3240
accaccgcct ggggcggaat ggggccgatg acctgaaggc ccaccccttc ttcagcgcca   3300
ttgacttctc cagtgacatc cggaagcagc cagccccta cgttcccacc atcagccacc   3360
ccatggacac ctcgaatttc gaccccgtag atgaagaaag cccttggaac gatgccagcg   3420
aaggtagcac caaggcctgg gacacactca cctcgcccaa taacaagcat cctgagcacg   3480
cattttacga attcaccttc cgaaggttct tgatgacaa tggctacccc tttcgatgcc   3540
caaagccttc aggagcagaa gcttcacagg ctgagagctc agatttagaa agctctgatc   3600
tggtggatca gactgaaggc tgccagcctg tgtacgtgta gatgggggcc aggcacccccc   3660
accactcgct gcctcccagg tcaggtccc ggagccggtg ccctcacagg ccaatagggga   3720
agccgagggc tgttttgttt taaattagtc cgtcgattac ttcacttgaa attctgctct   3780
tcaccaagaa aacccaaaca ggacactttt gaaaacagga ctcagcatcg ctttcaatag   3840
gcttttcagg accttcactg cattaaaaca atattttga aaatttagta cagtttagaa   3900
agagcactta ttttgtttat atccattttt tcttactaaa ttataggat taactttgac   3960
aaatcatgct gctgttattt tctacatttg tattttatcc atagcactta ttcacattta   4020
ggaaaagaca taaaaactga agaacattga tgagaaatct ctgtgcaata atgtaaaaaa   4080
aaaaaaagat aacactctgc tcaatgtcac ggagaccatt ttatccacac aatggttttt   4140
gttttttatt ttttcccatg tttcaaaatt gtgatataat gatataatgt taaaagctgc   4200
ttttttttggc ttttttgcata tctagtataa taggaagtgt gagcaaggtg atgatgtggc   4260
tgtgatttcc gacgtctggt gtgtggagag tactgcatga gcagagttct tctattataa   4320
aattaccata tcttgccatt cacagcaggt cctgtgaata cgttttttact gagtgtcttt   4380
aaatgaggtc ttctagacag tgtgctgata atgtattgtg cgggtgacct cttcgctatg   4440
attgtatctc ttactgttt gttaaagaaa tgcagatgtg taactgagaa gtgatttgtg   4500
tgtgtgtctt ggttgtgatt ggattctttg ggggggggg aactgaaaca tttgtcatat   4560
actgaactta tatacatcaa aagggattaa tacagcgatg ccaaaaagtt taatcacgga   4620
cacacgtccg tttctgtagt ccgtatgctc tttcattctt ggtagagctg gtatgtggaa   4680
tgccataccct ctgaccctac tacttacctt tttactgaca gactgcccac actgaaagct   4740
tcagtgaatg ttcttagtcc tgttttcttc tgttactgtc aggaaactga gtgatctaat   4800
ggttctctca cttttttttt gttcttttag tgtactttgg aagtatcaaa tcttaacttg   4860
gtttaaacaa tacatattcc taacctttgt aaaaaagcaa agattcttca aaatgacatt   4920
gaaataaaaa gtaagcccata cgtatttttct tagaagtata gatgtatgtg cgtgtataca   4980
cacacacaca cacacacaga gataaacaca atattcctta tttcaaatta gtatgattcc   5040
```

-continued

```
tatttaaagt gatttatatt tgagtaaaaa gttcaattct tttttgcttt ttaaaaaatc      5100
tgatgcttca taattttcat tatattattc cacatatttt tccttgaagt tcttagcata      5160
atgtatccat tacttagtat atatctaggc aacaacactt agaagtttat cagtgtttaa      5220
actaaaaaaa taaagattcc tgtgtactgg ttcaaaaaaa aaaaaaaaaa aaaaaa          5276
```

<210> SEQ ID NO 3
<211> LENGTH: 1130
<212> TYPE: PRT
<213> ORGANISM: HUMAN

<400> SEQUENCE: 3

```
Met Lys Arg Ser Glu Lys Pro Glu Gly Tyr Arg Gln Met Arg Pro Lys
  1               5                  10                  15

Thr Phe Pro Ala Ser Asn Tyr Thr Val Ser Ser Arg Gln Met Leu Gln
             20                  25                  30

Glu Ile Arg Glu Ser Leu Arg Asn Leu Ser Lys Pro Ser Asp Ala Ala
         35                  40                  45

Lys Ala Glu His Asn Met Ser Lys Met Ser Thr Glu Asp Pro Arg Gln
 50                  55                  60

Val Arg Asn Pro Pro Lys Phe Gly Thr His His Lys Ala Leu Gln Glu
 65                  70                  75                  80

Ile Arg Asn Ser Leu Leu Pro Phe Ala Asn Glu Thr Asn Ser Ser Arg
                 85                  90                  95

Ser Thr Ser Glu Val Asn Pro Gln Met Leu Gln Asp Leu Gln Ala Ala
            100                 105                 110

Gly Phe Asp Glu Asp Met Val Ile Gln Ala Leu Gln Lys Thr Asn Asn
        115                 120                 125

Arg Ser Ile Glu Ala Ala Ile Glu Phe Ile Ser Lys Met Ser Tyr Gln
130                 135                 140

Asp Pro Arg Arg Glu Gln Met Ala Ala Ala Ala Arg Pro Ile Asn
145                 150                 155                 160

Ala Ser Met Lys Pro Gly Asn Val Gln Gln Ser Val Asn Arg Lys Gln
                165                 170                 175

Ser Trp Lys Gly Ser Lys Glu Ser Leu Val Pro Gln Arg His Gly Pro
            180                 185                 190

Pro Leu Ala Glu Ser Val Ala Tyr His Ser Glu Ser Pro Asn Ser Gln
        195                 200                 205

Thr Asp Val Gly Arg Pro Leu Ser Gly Ser Gly Ile Ser Ala Phe Val
    210                 215                 220

Gln Ala His Pro Ser Asn Gly Gln Arg Val Asn Pro Pro Pro Pro
225                 230                 235                 240

Gln Val Arg Ser Val Thr Pro Pro Pro Pro Arg Gly Gln Thr Pro
                245                 250                 255

Pro Pro Arg Gly Thr Thr Pro Pro Pro Ser Trp Glu Pro Asn Ser
            260                 265                 270

Gln Thr Lys Arg Tyr Ser Gly Asn Met Glu Tyr Val Ile Ser Arg Ile
        275                 280                 285

Ser Pro Val Pro Pro Gly Ala Trp Gln Glu Gly Tyr Pro Pro Pro
    290                 295                 300

Leu Asn Thr Ser Pro Met Asn Pro Pro Asn Gln Gly Gln Arg Gly Ile
305                 310                 315                 320

Ser Ser Val Pro Val Gly Arg Gln Pro Ile Ile Met Gln Ser Ser Ser
                325                 330                 335
```

```
Lys Phe Asn Phe Pro Ser Gly Arg Pro Gly Met Gln Asn Gly Thr Gly
            340                 345                 350

Gln Thr Asp Phe Met Ile His Gln Asn Val Val Pro Ala Gly Thr Val
            355                 360                 365

Asn Arg Gln Pro Pro Pro Tyr Pro Leu Thr Ala Ala Asn Gly Gln
370                 375                 380

Ser Pro Ser Ala Leu Gln Thr Gly Gly Ser Ala Ala Pro Ser Ser Tyr
385                 390                 395                 400

Thr Asn Gly Ser Ile Pro Gln Ser Met Met Val Pro Asn Arg Asn Ser
                405                 410                 415

His Asn Met Glu Leu Tyr Asn Ile Ser Val Pro Gly Leu Gln Thr Asn
            420                 425                 430

Trp Pro Gln Ser Ser Ser Ala Pro Ala Gln Ser Ser Pro Ser Ser Gly
            435                 440                 445

His Glu Ile Pro Thr Trp Gln Pro Asn Ile Pro Val Arg Ser Asn Ser
    450                 455                 460

Phe Asn Asn Pro Leu Gly Asn Arg Ala Ser His Ser Ala Asn Ser Gln
465                 470                 475                 480

Pro Ser Ala Thr Thr Val Thr Ala Ile Thr Pro Ala Pro Ile Gln Gln
                485                 490                 495

Pro Val Lys Ser Met Arg Val Leu Lys Pro Glu Leu Gln Thr Ala Leu
            500                 505                 510

Ala Pro Thr His Pro Ser Trp Ile Pro Gln Pro Ile Gln Thr Val Gln
            515                 520                 525

Pro Ser Pro Phe Pro Glu Gly Thr Ala Ser Asn Val Thr Val Met Pro
            530                 535                 540

Pro Val Ala Glu Ala Pro Asn Tyr Gln Gly Pro Pro Pro Tyr Pro
545                 550                 555                 560

Lys His Leu Leu His Gln Asn Pro Ser Val Pro Pro Tyr Glu Ser Ile
                565                 570                 575

Ser Lys Pro Ser Lys Glu Asp Gln Pro Ser Leu Pro Lys Glu Asp Glu
            580                 585                 590

Ser Glu Lys Ser Tyr Glu Asn Val Asp Ser Gly Asp Lys Glu Lys Lys
            595                 600                 605

Gln Ile Thr Thr Ser Pro Ile Thr Val Arg Lys Asn Lys Lys Asp Glu
    610                 615                 620

Glu Arg Arg Glu Ser Arg Ile Gln Ser Tyr Ser Pro Gln Ala Phe Lys
625                 630                 635                 640

Phe Phe Met Glu Gln His Val Glu Asn Val Leu Lys Ser His Gln Gln
                645                 650                 655

Arg Leu His Arg Lys Lys Gln Leu Glu Asn Glu Met Met Arg Val Gly
            660                 665                 670

Leu Ser Gln Asp Ala Gln Asp Gln Met Arg Lys Met Leu Cys Gln Lys
            675                 680                 685

Glu Ser Asn Tyr Ile Arg Leu Lys Arg Ala Lys Met Asp Lys Ser Met
            690                 695                 700

Phe Val Lys Ile Lys Thr Leu Gly Ile Gly Ala Phe Gly Glu Val Cys
705                 710                 715                 720

Leu Ala Arg Lys Val Asp Thr Lys Ala Leu Tyr Ala Thr Lys Thr Leu
                725                 730                 735

Arg Lys Lys Asp Val Leu Leu Arg Asn Gln Val Ala His Val Lys Ala
            740                 745                 750
```

-continued

Glu Arg Asp Ile Leu Ala Glu Ala Asp Asn Glu Trp Val Val Arg Leu
        755                 760                 765

Tyr Tyr Ser Phe Gln Asp Lys Asp Asn Leu Tyr Phe Val Met Asp Tyr
    770                 775                 780

Ile Pro Gly Gly Asp Met Met Ser Leu Leu Ile Arg Met Gly Ile Phe
785                 790                 795                 800

Pro Glu Ser Leu Ala Arg Phe Tyr Ile Ala Glu Leu Thr Cys Ala Val
                805                 810                 815

Glu Ser Val His Lys Met Gly Phe Ile His Arg Asp Ile Lys Pro Asp
            820                 825                 830

Asn Ile Leu Ile Asp Arg Asp Gly His Ile Lys Leu Thr Asp Phe Gly
                835                 840                 845

Leu Cys Thr Gly Phe Arg Trp Thr His Asp Ser Lys Tyr Tyr Gln Ser
    850                 855                 860

Gly Asp His Pro Arg Gln Asp Ser Met Asp Phe Ser Asn Glu Trp Gly
865                 870                 875                 880

Asp Pro Ser Ser Cys Arg Cys Gly Asp Arg Leu Lys Pro Leu Glu Arg
                885                 890                 895

Arg Ala Ala Arg Gln His Gln Arg Cys Leu Ala His Ser Leu Val Gly
                900                 905                 910

Thr Pro Asn Tyr Ile Ala Pro Glu Val Leu Leu Arg Thr Gly Tyr Thr
            915                 920                 925

Gln Leu Cys Asp Trp Trp Ser Val Gly Val Ile Leu Phe Glu Met Leu
    930                 935                 940

Val Gly Gln Pro Pro Phe Leu Ala Gln Thr Pro Leu Glu Thr Gln Met
945                 950                 955                 960

Lys Val Ile Asn Trp Gln Thr Ser Leu His Ile Pro Pro Gln Ala Lys
                965                 970                 975

Leu Ser Pro Glu Ala Ser Asp Leu Ile Lys Leu Cys Arg Gly Pro
            980                 985                 990

Glu Asp Arg Leu Gly Lys Asn Gly Ala Asp Glu Ile Lys Ala His Pro
            995                 1000                1005

Phe Phe Lys Thr Ile Asp Phe Ser Ser Asp Leu Arg Gln Gln Ser Ala
    1010                1015                1020

Ser Tyr Ile Pro Lys Ile Thr His Pro Thr Asp Thr Ser Asn Phe Asp
025                 1030                1035                1040

Pro Val Asp Pro Asp Lys Leu Trp Ser Asp Asn Glu Glu Asn
                1045                1050                1055

Val Asn Asp Thr Leu Asn Gly Trp Tyr Lys Asn Gly Lys His Pro Glu
            1060                1065                1070

His Ala Phe Tyr Glu Phe Thr Phe Arg Arg Phe Phe Asp Asp Asn Gly
    1075                1080                1085

Tyr Pro Tyr Asn Tyr Pro Lys Pro Ile Glu Tyr Glu Tyr Ile Asn Ser
    1090                1095                1100

Gln Gly Ser Glu Gln Gln Ser Asp Glu Asp Gln Asn Thr Gly Ser
105                 1110                1115                1120

Glu Ile Lys Asn Arg Asp Leu Val Tyr Val
            1125                1130

<210> SEQ ID NO 4
<211> LENGTH: 1088
<212> TYPE: PRT
<213> ORGANISM: HUMAN

<400> SEQUENCE: 4

-continued

```
Met Arg Pro Lys Thr Phe Pro Ala Thr Thr Tyr Ser Gly Asn Ser Arg
 1               5                  10                  15

Gln Arg Leu Gln Glu Ile Arg Glu Gly Leu Lys Gln Pro Ser Lys Ser
             20                  25                  30

Ser Val Gln Gly Leu Pro Ala Gly Pro Asn Ser Asp Thr Ser Leu Asp
         35                  40                  45

Ala Lys Val Leu Gly Ser Lys Asp Ala Thr Arg Gln Gln Gln Gln Met
     50                  55                  60

Arg Ala Thr Pro Lys Phe Gly Pro Tyr Gln Lys Ala Leu Arg Glu Ile
 65                  70                  75                  80

Arg Tyr Ser Leu Leu Pro Phe Ala Asn Glu Ser Gly Thr Ser Ala Ala
                 85                  90                  95

Ala Glu Val Asn Arg Gln Met Leu Gln Glu Leu Val Asn Ala Gly Cys
             100                 105                 110

Asp Gln Glu Met Ala Gly Arg Ala Leu Lys Gln Thr Gly Ser Arg Ser
             115                 120                 125

Ile Glu Ala Ala Leu Glu Tyr Ile Ser Lys Met Gly Tyr Leu Asp Pro
         130                 135                 140

Arg Asn Glu Gln Ile Val Arg Val Ile Lys Gln Thr Ser Pro Gly Lys
145                 150                 155                 160

Gly Leu Met Pro Thr Pro Val Thr Arg Arg Pro Ser Phe Glu Gly Thr
                 165                 170                 175

Gly Asp Ser Phe Ala Ser Tyr His Gln Leu Ser Gly Thr Pro Tyr Glu
             180                 185                 190

Gly Pro Ser Phe Gly Ala Asp Gly Pro Thr Ala Leu Glu Glu Met Pro
         195                 200                 205

Arg Pro Tyr Val Asp Tyr Leu Phe Pro Gly Val Gly Pro His Gly Pro
     210                 215                 220

Gly His Gln His Gln His Pro Pro Lys Gly Tyr Gly Ala Ser Val Glu
225                 230                 235                 240

Ala Ala Gly Ala His Phe Pro Leu Gln Gly Ala His Tyr Gly Arg Pro
                 245                 250                 255

His Leu Leu Val Pro Gly Glu Pro Leu Gly Tyr Gly Val Gln Arg Ser
             260                 265                 270

Pro Ser Phe Gln Ser Lys Thr Pro Pro Glu Thr Gly Gly Tyr Ala Ser
         275                 280                 285

Leu Pro Thr Lys Gly Gln Gly Gly Pro Gly Ala Gly Leu Ala Phe
     290                 295                 300

Pro Pro Pro Ala Ala Gly Leu Tyr Val Pro His Pro His His Lys Gln
305                 310                 315                 320

Ala Gly Pro Ala Ala His Gln Leu His Val Leu Gly Ser Arg Ser Gln
                 325                 330                 335

Val Phe Ala Ser Asp Ser Pro Gln Ser Leu Leu Thr Pro Ser Arg
             340                 345                 350

Asn Ser Leu Asn Val Asp Leu Tyr Glu Leu Gly Ser Thr Ser Val Gln
         355                 360                 365

Gln Trp Pro Ala Ala Thr Leu Ala Arg Arg Asp Ser Leu Gln Lys Pro
     370                 375                 380

Gly Leu Glu Ala Pro Arg Ala His Val Ala Phe Arg Pro Asp Cys
385                 390                 395                 400

Pro Val Pro Ser Arg Thr Asn Ser Phe Asn Ser His Gln Pro Arg Pro
                 405                 410                 415
```

-continued

```
Gly Pro Pro Gly Lys Ala Glu Pro Ser Leu Pro Ala Pro Asn Thr Val
            420                 425                 430

Thr Ala Val Thr Ala Ala His Ile Leu His Pro Val Lys Ser Val Arg
            435                 440                 445

Val Leu Arg Pro Glu Pro Gln Thr Ala Val Gly Pro Ser His Pro Ala
            450                 455                 460

Trp Val Pro Ala Pro Ala Pro Ala Pro Ala Pro Ala Pro Ala Pro Ala
465                 470                 475                 480

Ala Glu Gly Leu Asp Ala Lys Glu His Ala Leu Ala Leu Gly Gly
                485                 490                 495

Ala Gly Ala Phe Pro Leu Asp Val Glu Tyr Gly Gly Pro Asp Arg Arg
            500                 505                 510

Cys Pro Pro Pro Tyr Pro Lys His Leu Leu Arg Ser Lys Ser
            515                 520                 525

Glu Gln Tyr Asp Leu Asp Ser Leu Cys Ala Gly Met Glu Gln Ser Leu
            530                 535                 540

Arg Ala Gly Pro Asn Glu Pro Glu Gly Gly Asp Lys Ser Arg Lys Ser
545                 550                 555                 560

Ala Lys Gly Asp Lys Gly Gly Lys Asp Lys Lys Gln Ile Gln Thr Ser
                565                 570                 575

Pro Val Pro Val Arg Lys Asn Ser Arg Asp Glu Glu Lys Arg Glu Ser
            580                 585                 590

Arg Ile Lys Ser Tyr Ser Pro Tyr Ala Phe Lys Phe Phe Met Glu Gln
            595                 600                 605

His Val Glu Asn Val Ile Lys Thr Tyr Gln Gln Lys Val Asn Arg Arg
            610                 615                 620

Leu Gln Leu Glu Gln Glu Met Ala Lys Ala Gly Leu Cys Glu Ala Glu
625                 630                 635                 640

Gln Glu Gln Met Arg Lys Ile Leu Tyr Gln Lys Glu Ser Asn Tyr Asn
                645                 650                 655

Arg Leu Lys Arg Ala Lys Met Asp Lys Ser Met Phe Val Lys Ile Lys
            660                 665                 670

Thr Leu Gly Ile Gly Ala Phe Gly Glu Val Cys Leu Ala Cys Lys Val
            675                 680                 685

Asp Thr His Ala Leu Tyr Ala Met Lys Thr Leu Arg Lys Lys Asp Val
            690                 695                 700

Leu Asn Arg Asn Gln Val Ala His Val Lys Ala Glu Arg Asp Ile Leu
705                 710                 715                 720

Ala Glu Ala Asp Asn Glu Trp Val Val Lys Leu Tyr Tyr Ser Phe Gln
                725                 730                 735

Asp Lys Asp Ser Leu Tyr Phe Val Met Asp Tyr Ile Pro Gly Gly Asp
            740                 745                 750

Met Met Ser Leu Leu Ile Arg Met Glu Val Phe Pro Glu His Leu Ala
            755                 760                 765

Arg Phe Tyr Ile Ala Glu Leu Thr Leu Ala Ile Glu Ser Val His Lys
            770                 775                 780

Met Gly Phe Ile His Arg Asp Ile Lys Pro Asp Asn Ile Leu Ile Asp
785                 790                 795                 800

Leu Asp Gly His Ile Lys Leu Thr Asp Phe Gly Leu Cys Thr Gly Phe
                805                 810                 815

Arg Trp Thr His Asn Ser Lys Tyr Tyr Gln Lys Gly Ser His Val Arg
            820                 825                 830

Gln Asp Ser Met Glu Pro Ser Asp Leu Trp Asp Asp Val Ser Asn Cys
```

-continued

```
                        835                 840                 845
Arg Cys Gly Asp Arg Leu Lys Thr Leu Glu Gln Arg Ala Arg Lys Gln
850                 855                 860
His Gln Arg Cys Leu Ala His Ser Leu Val Gly Thr Pro Asn Tyr Ile
865                 870                 875                 880
Ala Pro Glu Val Leu Arg Lys Gly Tyr Thr Gln Leu Cys Asp Trp
                885                 890                 895
Trp Ser Val Gly Val Ile Leu Phe Glu Met Leu Val Gly Gln Pro Pro
                900                 905                 910
Phe Leu Ala Pro Thr Pro Thr Glu Thr Gln Leu Lys Val Ile Asn Trp
                915                 920                 925
Glu Asn Thr Leu His Ile Pro Ala Gln Val Lys Leu Ser Pro Glu Ala
                930                 935                 940
Arg Asp Leu Ile Thr Lys Leu Cys Cys Ser Ala Asp His Arg Leu Gly
945                 950                 955                 960
Arg Asn Gly Ala Asp Asp Leu Lys Ala His Pro Phe Phe Ser Ala Ile
                965                 970                 975
Asp Phe Ser Ser Asp Ile Arg Lys Gln Pro Ala Pro Tyr Val Pro Thr
                980                 985                 990
Ile Ser His Pro Met Asp Thr Ser Asn Phe Asp Pro Val Asp Glu Glu
                995                 1000                1005
Ser Pro Trp Asn Asp Ala Ser Glu Gly Ser Thr Lys Ala Trp Asp Thr
        1010                1015                1020
Leu Thr Ser Pro Asn Asn Lys His Pro Glu His Ala Phe Tyr Glu Phe
1025                1030                1035                1040
Thr Phe Arg Arg Phe Phe Asp Asp Asn Gly Tyr Pro Phe Arg Cys Pro
                1045                1050                1055
Lys Pro Ser Gly Ala Glu Ala Ser Gln Ala Glu Ser Ser Asp Leu Glu
                    1060                1065                1070
Ser Ser Asp Leu Val Asp Gln Thr Glu Gly Cys Gln Pro Val Tyr Val
            1075                1080                1085

<210> SEQ ID NO 5
<211> LENGTH: 23
<212> TYPE: DNA
<213> ORGANISM: HUMAN
<220> FEATURE:
<223> OTHER INFORMATION: The letter "y" stands for c or t.
      The letter "n" stands for a, c, g or t.
      The letter "r" stands for a or g.
      The letter "h" stands for a, c or t.

<400> SEQUENCE: 5
caygtnaara thacngaytt ygg                                          23

<210> SEQ ID NO 6
<211> LENGTH: 20
<212> TYPE: DNA
<213> ORGANISM: HUMAN
<220> FEATURE:
<223> OTHER INFORMATION: The letter "r" stands for a or g.
      The letter "d" stands for a, g or t.
      The letter "y" stands for c or t.

<400> SEQUENCE: 6
ggrtcdatca tccagcaytt                                              20

<210> SEQ ID NO 7
<211> LENGTH: 6
```

```
<212> TYPE: PRT
<213> ORGANISM: HUMAN

<400> SEQUENCE: 7

Lys Ile Thr Asp Phe Gly
  1               5

<210> SEQ ID NO 8
<211> LENGTH: 6
<212> TYPE: PRT
<213> ORGANISM: HUMAN

<400> SEQUENCE: 8

Lys Cys Trp Met Ile Asp
  1               5

<210> SEQ ID NO 9
<211> LENGTH: 27
<212> TYPE: DNA
<213> ORGANISM: HUMAN
<220> FEATURE:
<223> OTHER INFORMATION: The letter "r" stands for a or g.
      The letter "d" stands for a, g or t.
      The letter "n" stands for a, c, g or t.
      The letter "s" stands for c or g.
      The letter "w" stands for for a or t.

<400> SEQUENCE: 9
tccraacagd atnacnccna cnswcca                                             27

<210> SEQ ID NO 10
<211> LENGTH: 27
<212> TYPE: DNA
<213> ORGANISM: HUMAN
<220> FEATURE:
<223> OTHER INFORMATION: The letter "y" stands for c or t.
      The letter "n" stands for a, c, g or t.
      The letter "m" stands for a or c.

<400> SEQUENCE: 10
ttyggnytnt gyacnggntt ymgntgg                                             27

<210> SEQ ID NO 11
<211> LENGTH: 9
<212> TYPE: PRT
<213> ORGANISM: HUMAN

<400> SEQUENCE: 11

Phe Gly Leu Cys Thr Gly Phe Arg Trp
  1               5

<210> SEQ ID NO 12
<211> LENGTH: 9
<212> TYPE: PRT
<213> ORGANISM: HUMAN

<400> SEQUENCE: 12

Trp Ser Val Gly Val Ile Leu Phe Glu
  1               5

<210> SEQ ID NO 13
<211> LENGTH: 1088
<212> TYPE: PRT
<213> ORGANISM: HUMAN

<400> SEQUENCE: 13
```

-continued

```
Met His Pro Ala Gly Glu Lys Arg Gly Arg Pro Asn Asp Lys Tyr
  1               5                  10                 15

Thr Ala Glu Ala Leu Glu Ser Ile Lys Gln Asp Leu Thr Arg Phe Glu
                 20                  25                 30

Val Gln Asn Asn His Arg Asn Asn Gln Asn Tyr Thr Pro Leu Arg Tyr
             35                  40                 45

Thr Ala Thr Asn Gly Arg Asn Asp Ala Leu Thr Pro Asp Tyr His His
 50                      55                 60

Ala Lys Gln Pro Met Glu Pro Pro Ser Ala Ser Pro Ala Pro Asp
 65              70                  75                 80

Val Val Ile Pro Pro Pro Ala Ile Val Gly Gln Pro Gly Ala Gly
                 85                  90                 95

Ser Ile Ser Val Ser Gly Val Gly Val Val Gly Val Ala Asn
                 100                 105                110

Gly Arg Val Pro Lys Met Met Thr Ala Leu Met Pro Asn Lys Leu Ile
             115                 120                125

Arg Lys Pro Ser Ile Glu Arg Asp Thr Ala Ser Ser His Tyr Leu Arg
 130                     135                140

Cys Ser Pro Ala Leu Asp Ser Gly Ala Gly Ser Ser Arg Ser Asp Ser
145                 150                 155                160

Pro His Ser His His Thr His Gln Pro Ser Ser Arg Thr Val Gly Asn
                 165                 170                175

Pro Gly Gly Asn Gly Gly Phe Ser Pro Ser Pro Ser Gly Phe Ser Glu
             180                 185                 190

Val Ala Pro Pro Ala Pro Pro Arg Asn Pro Thr Ala Ser Ser Ala
                 195                 200                205

Ala Thr Pro Pro Pro Val Pro Pro Thr Ser Gln Ala Tyr Val Lys
 210                     215                 220

Arg Arg Ser Pro Ala Leu Asn Asn Arg Pro Pro Ala Ile Ala Pro Pro
225                 230                 235                240

Thr Gln Arg Gly Asn Ser Pro Val Ile Thr Gln Asn Gly Leu Lys Asn
                 245                 250                255

Pro Gln Gln Gln Leu Thr Gln Gln Leu Lys Ser Leu Asn Leu Tyr Pro
                 260                 265                270

Gly Gly Gly Ser Gly Ala Val Val Glu Pro Pro Pro Tyr Leu Ile
             275                 280                285

Gln Gly Gly Ala Gly Gly Ala Ala Pro Pro Pro Pro Pro Ser Tyr
 290                     295                 300

Thr Ala Ser Met Gln Ser Arg Gln Ser Pro Thr Gln Ser Gln Gln Ser
305                 310                 315                320

Asp Tyr Arg Lys Ser Pro Ser Ser Gly Ile Tyr Ser Ala Thr Ser Ala
                 325                 330                335

Gly Ser Pro Ser Pro Ile Thr Val Ser Leu Pro Pro Ala Pro Leu Ala
             340                 345                350

Lys Pro Gln Pro Arg Val Tyr Gln Ala Arg Ser Gln Gln Pro Ile Ile
                 355                 360                365

Met Gln Ser Val Lys Ser Thr Gln Val Gln Lys Pro Val Leu Gln Thr
 370                     375                 380

Ala Val Ala Pro Gln Ser Pro Ser Ser Ala Ser Ala Ser Asn Ser Pro
385                 390                 395                400

Val His Val Leu Ala Ala Pro Pro Ser Tyr Pro Gln Lys Ser Ala Ala
                 405                 410                415

Val Val Gln Gln Gln Gln Gln Ala Ala Ala Ala Ala His Gln Gln Gln
```

```
                420             425             430
His Gln His Gln Gln Ser Lys Pro Ala Thr Pro Thr Thr Pro Pro Leu
            435             440             445
Val Gly Leu Asn Ser Lys Pro Asn Cys Leu Glu Pro Pro Ser Tyr Ala
450             455             460
Lys Ser Met Gln Ala Lys Ala Ala Thr Val Val Gln Gln Gln Gln Gln
465             470             475             480
Gln Gln Gln Gln Gln Gln Val Gln Gln Gln Val Gln Gln Gln Gln
            485             490             495
Gln Gln Gln Gln Gln Gln Leu Gln Ala Leu Arg Val Leu Gln Ala Gln
            500             505             510
Ala Gln Arg Glu Arg Asp Gln Arg Glu Arg Asp Gln Gln Lys
            515             520             525
Leu Ala Asn Gly Asn Pro Gly Arg Gln Met Leu Pro Pro Pro Tyr
            530             535             540
Gln Ser Asn Asn Asn Asn Ser Glu Ile Lys Pro Pro Ser Cys Asn
545             550             555             560
Asn Asn Asn Ile Gln Ile Ser Asn Ser Asn Leu Ala Thr Thr Pro Pro
            565             570             575
Ile Pro Pro Ala Lys Tyr Asn Asn Asn Ser Ser Asn Thr Gly Ala Asn
            580             585             590
Ser Ser Gly Gly Ser Asn Gly Ser Thr Gly Thr Thr Ala Ser Ser Ser
            595             600             605
Thr Ser Cys Lys Lys Ile Lys His Ala Ser Pro Ile Pro Glu Arg Lys
            610             615             620
Lys Ile Ser Lys Glu Lys Glu Glu Arg Lys Glu Phe Arg Ile Arg
625             630             635             640
Trp Ala Arg Thr His Ser Pro Gln Ala Phe Lys Phe Met Glu Gln
            645             650             655
His Ile Glu Asn Val Ile Lys Ser Tyr Arg Gln Arg Thr Tyr Arg Lys
            660             665             670
Asn Gln Leu Glu Lys Glu Met His Lys Val Gly Leu Pro Asp Gln Thr
            675             680             685
Gln Ile Glu Met Arg Lys Met Leu Asn Gln Lys Glu Ser Asn Tyr Ile
            690             695             700
Arg Leu Lys Arg Ala Lys Met Asp Lys Ser Met Phe Val Lys Leu Lys
705             710             715             720
Pro Ile Gly Val Gly Ala Phe Gly Glu Val Thr Leu Val Ser Lys Ile
            725             730             735
Asp Thr Ser Asn His Leu Tyr Ala Met Lys Thr Leu Arg Lys Ala Asp
            740             745             750
Val Leu Lys Arg Asn Gln Val Ala His Val Lys Ala Glu Arg Asp Ile
            755             760             765
Leu Ala Glu Ala Asp Asn Asn Trp Val Val Lys Leu Tyr Tyr Ser Phe
770             775             780
Gln Asp Lys Asp Asn Leu Tyr Phe Val Met Asp Tyr Ile Pro Gly Gly
785             790             795             800
Asp Leu Met Ser Leu Leu Ile Lys Leu Gly Ile Phe Glu Glu Glu Leu
            805             810             815
Ala Arg Phe Tyr Ile Ala Glu Val Thr Cys Ala Val Asp Ser Val His
            820             825             830
Lys Met Gly Phe Ile His Arg Asp Ile Lys Pro Asp Asn Ile Leu Ile
            835             840             845
```

-continued

```
Asp Arg Asp Gly His Ile Lys Leu Thr Asp Phe Gly Leu Cys Thr Gly
        850                 855                 860

Phe Arg Trp Thr His Asn Ser Lys Tyr Tyr Gln Glu Asn Gly Asn His
865                 870                 875                 880

Ser Arg Gln Asp Ser Met Glu Pro Trp Glu Tyr Ser Glu Asn Gly
                885                 890                 895

Pro Lys Pro Thr Val Leu Glu Arg Arg Met Arg Asp His Gln Arg
                900                 905                 910

Val Leu Ala His Ser Leu Val Gly Thr Pro Asn Tyr Ile Ala Pro Glu
            915                 920                 925

Val Leu Glu Arg Ser Gly Tyr Thr Gln Leu Cys Asp Tyr Trp Ser Val
        930                 935                 940

Gly Val Ile Leu Tyr Glu Met Leu Val Gly Gln Pro Pro Phe Leu Ala
945                 950                 955                 960

Asn Ser Pro Leu Glu Thr Gln Gln Lys Val Ile Asn Trp Glu Lys Thr
                965                 970                 975

Leu His Ile Pro Pro Gln Ala Glu Leu Ser Arg Glu Ala Thr Asp Leu
            980                 985                 990

Ile Arg Arg Leu Cys Ala Ser Ala Asp Lys Arg Leu Gly Lys Ser Val
        995                 1000                1005

Asp Glu Val Lys Ser His Asp Phe Phe Lys Gly Ile Asp Phe Ala Asp
    1010                1015                1020

Met Arg Lys Gln Lys Ala Pro Tyr Ile Pro Glu Ile Lys His Pro Thr
1025                1030                1035                1040

Asp Thr Ser Asn Phe Asp Pro Val Asp Pro Glu Lys Leu Arg Ser Asn
                1045                1050                1055

Asp Ser Thr Met Ser Ser Gly Asp Asp Val Asp Gln Asn Asp Arg Thr
            1060                1065                1070

Phe His Gly Phe Phe Glu Phe Thr Phe Arg Arg Phe Asp Asp Lys
    1075                1080                1085

<210> SEQ ID NO 14
<211> LENGTH: 10
<212> TYPE: PRT
<213> ORGANISM: HUMAN

<400> SEQUENCE: 14

Tyr Pro Tyr Asp Val Pro Asp Tyr Ala Ser
1               5                   10

<210> SEQ ID NO 15
<211> LENGTH: 14
<212> TYPE: PRT
<213> ORGANISM: HUMAN

<400> SEQUENCE: 15

Ile Ser Lys Pro Ser Lys Glu Asp Gln Pro Ser Leu Pro Lys
1               5                   10

<210> SEQ ID NO 16
<211> LENGTH: 17
<212> TYPE: PRT
<213> ORGANISM: HUMAN

<400> SEQUENCE: 16

Asp Asp Gln Asn Thr Gly Ser Glu Ile Lys Asn Arg Asp Leu Val Tyr
1               5                   10                  15
```

-continued

Val

<210> SEQ ID NO 17
<211> LENGTH: 16
<212> TYPE: PRT
<213> ORGANISM: HUMAN

<400> SEQUENCE: 17

Pro Ser Gly Lys Asn Ser Arg Asp Glu Glu Lys Arg Glu Ser Arg Ile
1               5                   10                  15

<210> SEQ ID NO 18
<211> LENGTH: 15
<212> TYPE: PRT
<213> ORGANISM: HUMAN

<400> SEQUENCE: 18

Ser Asp Leu Val Asp Gln Thr Glu Gly Cys Gln Pro Val Tyr Val
1               5                   10                  15